US008106190B2

(12) United States Patent
Kuramochi et al.

(10) Patent No.: US 8,106,190 B2
(45) Date of Patent: Jan. 31, 2012

(54) 2-AMINOBENZAMIDE DERIVATIVES

(75) Inventors: Takahiro Kuramochi, Tokyo (JP); Ryoji Hirabayashi, Tokyo (JP); Yohei Koganemaru, Tokyo (JP); Ryosuke Munakata, Tokyo (JP); Koichi Yonezawa, Tokyo (JP); Tetsuo Kiso, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 685 days.

(21) Appl. No.: 12/094,298

(22) PCT Filed: Nov. 29, 2006

(86) PCT No.: PCT/JP2006/323863

§ 371 (c)(1),
(2), (4) Date: May 20, 2008

(87) PCT Pub. No.: WO2007/063925

PCT Pub. Date: Jun. 7, 2007

(65) Prior Publication Data

US 2009/0233900 A1 Sep. 17, 2009

(30) Foreign Application Priority Data

Nov. 30, 2005 (JP) ................................. 2005-345502

(51) Int. Cl.

| | |
|---|---|
| *C07D 265/30* | (2006.01) |
| *C07D 265/36* | (2006.01) |
| *C07D 405/04* | (2006.01) |
| *C07D 413/00* | (2006.01) |

(52) U.S. Cl. ......... 544/105; 544/106; 544/141; 544/374

(58) Field of Classification Search ........................ None
See application file for complete search history.

(56) References Cited

U.S. PATENT DOCUMENTS

| | | | | |
|---|---|---|---|---|
| 2002/0019414 A1 | | 2/2002 | Altmann et al. | |
| 2003/0134836 A1 | * | 7/2003 | Elbaum et al. | 514/210.2 |
| 2003/0225106 A1 | * | 12/2003 | Askew et al. | 514/256 |
| 2004/0039019 A1 | * | 2/2004 | Huth et al. | 514/314 |
| 2005/0165028 A1 | | 7/2005 | Norman et al. | |
| 2007/0167444 A1 | | 7/2007 | Kuramochi et al. | |

FOREIGN PATENT DOCUMENTS

| | | | | |
|---|---|---|---|---|
| EP | 1 280 799 | | | 2/2003 |
| EP | 1 632 477 | A1 | | 3/2006 |
| JP | 11 171848 | | | 6/1999 |
| JP | 3013989 | | | 12/1999 |
| WO | WO00/27819 | A2 | * | 5/2000 |
| WO | WO00/27820 | A1 | * | 5/2000 |
| WO | 01 85671 | | | 11/2001 |
| WO | WO 01/85719 | A1 | | 11/2001 |
| WO | WO02/090352 | A2 | * | 11/2002 |
| WO | 2004 005279 | | | 1/2004 |
| WO | 2004 007457 | | | 1/2004 |
| WO | 2004 007458 | | | 1/2004 |
| WO | 2004 039795 | | | 5/2004 |
| WO | 2004 056780 | | | 7/2004 |
| WO | 2004 069792 | | | 8/2004 |
| WO | 2004 072069 | | | 8/2004 |
| WO | 2004 108133 | | | 12/2004 |
| WO | 2004 110986 | | | 12/2004 |
| WO | 2005 072681 | | | 8/2005 |
| WO | WO 2006/002383 | A2 | | 1/2006 |
| WO | WO 2006/002383 | A3 | | 1/2006 |
| WO | 2006 038871 | | | 4/2006 |
| WO | 2006 048251 | | | 5/2006 |

OTHER PUBLICATIONS

Richard B. Silverman, The Organic Chemistry of Drug Design and Drug Action, Academic Press (1992).*
Extended Supplementary European Search Report dated Dec. 30, 2010 in corresponding European Application No. 06 83 3666.

* cited by examiner

*Primary Examiner* — Janet Andres
*Assistant Examiner* — Timothy R Rozof
(74) *Attorney, Agent, or Firm* — Oblon, Spivak, McClelland, Maier & Neustadt, L.L.P.

(57) ABSTRACT

To provide a novel and excellent agent for treating or preventing nociceptive pain, neuropathic pain, cancer pain, headache, bladder function disorder and the like, based on the inhibitory action on the capsaicin receptor VR1 activation. The present invention was accomplished by confirming that a benzamide derivative characterized by the possession of a benzene ring in which a single ring is condensed on the nitrogen atom of amido group and possession of a lower alkylamino or an amino group substituted with a ring group at the neighboring position of said amido group has a strong inhibitory action on VR1 activation and excellent pharmacological actions based on this and by finding that it can become an excellent agent for treating or preventing VR1-involved diseases such as nociceptive pain, neuropathic pain, cancer pain, headache, bladder function disorder and the like.

4 Claims, No Drawings

2-AMINOBENZAMIDE DERIVATIVES

TECHNICAL FIELD

The present invention relates to a pharmaceutical, particularly a novel 2-aminobenzamide derivative or a salt thereof useful as an inhibitor for the capsaicin receptor VR1 (Vanilloid Receptor 1) activation, and a pharmaceutical thereof.

BACKGROUND OF THE INVENTION

VR1 is a receptor which exists in the primary afferent sensory nerve (mainly C fiber) and involved in the pain at various pathological condition. The said receptor is activated by capsaicin which is the main component of red pepper, and pain is induced thereby. It is known that not only the pain by capsaicin disappears in a VR1 deletion mouse but also hyperalgesia at the time of inflammation is attenuated [Nature, 405: 183-187 (2000)].

Capsaicin induces a pain by activating VR1 as described in the above, but it is known that it shows, on the contrary, an analgesic action by desensitizing an afferent nerve through the persistent activation and inhibition of the activation thereafter [Pharmacol. Rev., 51: 159-211 (1999); Drugs Aging, 18: 561-573 (2001)]. In fact, a capsaicin cream is used for the treatment of neuropathic pains such as postherpetic neuralgia and diabetic neuropathic pain and nociceptive pains such as rheumatic joint pain which is classified into inflammatory pains. On the other hand, it is known that not only the VR1 agonist but also the VR1 antagonist also shows analgesic action by inhibiting activation of the VR1 receptor. For example, it has been reported that a conventionally known VR1 antagonist, capsazepin, shows efficacy for neuropathic pain and inflammatory pain in animal models [J. Pharmacol Exp. Ther., 304: 56-62 (2003)].

As the diseases for which an agonist or antagonist for VR1 receptor could show efficacy, for example, neuropathic pains such as postherpetic neuralgia [Clin. Ter., 15: 510-526 (1993)], diabetic neuropathy [Arch. Intern. Med., 151: 2225-2229 (1991)] and the like, nociceptive pains such as joint pain [Clin. Ther., 13: 383-395 (1991)], postoperative pain [J. Pharmacol. Exp. Ther., 314: 410-421 (2005)], back pain [Pain, 106: 59-64 (2003)] and the like, headaches such as migraine [Cephalalgia, 20: 597-602 (2000)], cluster headache [Clin. J. Pain, 5: 49-53 (1989)] and the like, or cancer pain [J. Neurosci., 25: 3126-3131 (2005)] and fibromyalgia [Semin. Arthritis Rheum., 3: 41-47 (1994)] can be cited. Inhibitors for VR1 receptor activation are useful for the treatment of the diseases described above.

In addition, it is known that bladder function disorders are alleviated by injecting capsaicin or its analogous substance resiniferatoxin (RTX) into the bladder of a spinal cord injury patient and the like [J. Urol., 162: 3-11 (1999)]. This is considered to be based on desensitization of afferent nerve similar to the case of analgesic action. Accordingly, in addition to the bladder function disorders such as overactive bladder, urinary incontinence, neurogenic bladder, nocturia and the like, an inhibitor for VR1 receptor activation is also useful for a bladder dysfunction which accompanies prostate hypertrophy [Drugs Aging, 18: 561-573 (2001)]. In addition, a therapeutic effect for painful bladder syndrome [J. Urol., 176: 797-801 (2006)], interstitial cystitis [Can. J. Urol., 6: 737-744 (1999)] and chronic non-bacterial prostatitis [Eur. Urol., 48: 162-167 (2005)] by inhibiting activation of VR1 receptor has been suggested.

In recent years, studies have been making progress on the compounds having inhibitory action on VR1 activation. For example, it has been reported that the derivative represented by the following general formula, as a VR1 regulating agent, is useful for the treatment of pain and the like (Patent Reference 1).

(II)

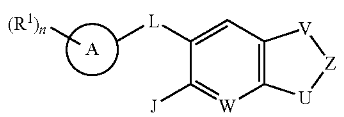

(In the formula, Z represents C═O or N, V and U are independently a group selected from the class consisting of O, S, C═O, —$CH_2$— and —$NR^2$— [wherein $R^2$ is H, $C_{1-4}$ alkyl or the like], W is C or N, J is hydrogen or the like, L is —NH—C(O)—$(CH_2)_q$—, —C(O)—NH—$(CH_2)_q$— or the like [wherein q is 0 to 2], A ring is $C_{3-7}$ cycloalkyl, phenyl or the like, $R^1$ is independently $C_{1-6}$ alkyl, $C_{1-6}$ alkoxy, -halo, —$CF_3$, —O—$CF_3$, —$NH_2$, —NH($C_{1-4}$ alkyl) or the like and n is 0 to 5, respectively. For details, see said official gazette.)

Also, it has been reported that the carboxamide derivative represented by the following general formula (III), as a VR1 regulating agent, is useful for the treatment of pain and the like (Patent Reference 2).

(III)

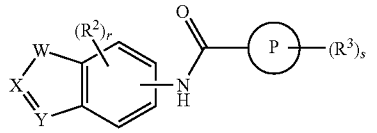

(In the formula, P is aryl, heteroaryl or the like, W, X and Y form a 5-membered nitrogen-containing hetero aromatic ring [wherein W, X and Y are selected from $CR^{1a}$, $NR^{1b}$, N, S and O], $CR^{1a}$ and $NR^{1b}$ are independently —H, alkyl or the like, $R^2$ is independently —H, alkyl or the like, $R^3$ is —H, halo, —$NR^4R^5$ or the like [$R^4$ and $R^5$ may be the same or different from each other and each represents —H or alkyl, or $R^4$ and $R^5$ may form a hetero ring together with the nitrogen atom to which they are bonded], r is 0, 1, 2 or 3, and s is 0, 1, 2, 3, 4, 5 or 6. For details, see said official gazette.)

Also, it has been reported that the derivative represented by the following general formula (IV), as a ligand for the VR1 receptor, is useful for the treatment of pain and the like (Patent References 3 and 4).

(IV)

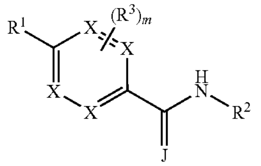

(In the formula, J is ═O or the like, X's are independently N or C, $R^1$ is $C_{2-6}$ alkyl, $C_{1-6}$ alkyl which may be substituted, or the like, $R^2$ is a saturated, partially saturated or unsaturated 9- or 10-membered bicyclic ring which contains 0, 1, 2 or 3 nitrogen atoms and 0, 1, 2 or 3 atoms selected from O and S [the total number of O and S atoms in the bicyclic ring does not exceed 2] and the bicyclic ring contains at least one N, O or S atom (the rest is omitted), and $R^3$ is $R^e$, $C_{1-4}$ halo-alkyl, halo, (the middle is omitted), —$NR^aR^a$, —$NR^aC_{2-6}alkylNR^aR^a$ or the like [$R^a$'s are independently H or $R^b$, and $R^b$'s are independently phenyl, benzyl or the like]. For details, see said official gazette.)

Though compounds having arylamide structure are disclosed in all of the Patent References 1 to 4 described in the above, there is no illustrative disclosure on a compound having a monoalkylamino group at the adjusting position of amido group on the aryl.

In addition, it has been reported that the quinoline derivative represented by the following general formula (V), as a regulatory agent of VR1 receptor, is useful for the treatment of pain and the like (Patent Reference 5).

(V)

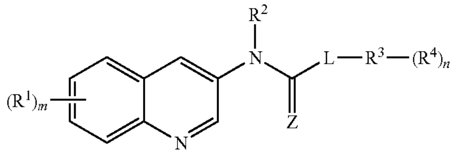

(In the formula, $R^1$ is hydrogen, hydroxy, halogen or the like, m is 0, 1 or 2, $R^2$ is hydrogen or $C_{1-8}$ alkanyl, L is a direct bond or the like, $R^3$ is pyrrolyl, pyridyl, phenyl or the like, $R^4$ is $C_{1-12}$ alkanyl, —$N(R^5)(R^6)$ [$R^5$ is hydrogen or the like and $R^6$ is $C_{4-16}$ alkyl, alkanylcarbonyl, or $C_{1-3}$ alkyl substituted with a group selected from the class consisting of pyrrolyl, pyridyl, furyl, thienyl and phenyl, or arylcarbonyl or the like] or the like, n is 1, 2 or 3 and Z is O or S, respectively. For details, see said official gazette.)

Also, a benzothiazole derivative characterized by its possession of VR1 receptor regulatory action and possession of hydroxymethyl group at the 2-position is disclosed in an international publication (Patent Reference 6) which was published after the application as the basis of the priority of the instant application.

In addition, a benzamide derivative characterized by its possession of VR1 receptor regulatory action and by substitution of a ring structure at the 4-position is disclosed in an international publication which was published by the applicant of the instant application, etc. (Patent Reference 7).

the nociceptin antagonist which comprises an amide derivative represented by the following general formula (VI) as the active ingredient has been reported (Patent Reference 8).

(VI)

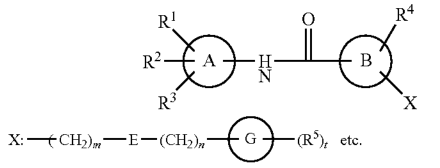

(In the formula, $R^1$ and $R^2$ may be the same or different from each other and each represents hydrogen atom, (lower alkyl group which may be substituted by hydroxyl group), amino group, lower alkylamino group or di(lower alkyl)amino group, $R^3$ and $R^4$ may be the same or different from each other and each represents hydrogen atom, halogen atom or lower alkyl group, ring A is aryl group or heterocyclic ring group, ring B is phenyl group or the like, E is single bond, —$NR^7$— or the like [$R^7$ is hydrogen atom or the like], ring G is aryl, heterocyclic ring group, cycloalkyl group or the like, $R^5$ is halogen atom, hydroxyl group, di(lower alkyl)amino group or the like, t is 0 or an integer of from 1 to 5, m is 0 or an integer of from 1 to 8, and n is 0 or an integer of from 1 to 4. For details, see said official gazette.)

Though use of the nociceptin antagonist of said official gazette is for pain, there is no disclosure or suggestion therein on VR1 receptor. Though compounds having arylamide structure are disclosed in said official gazette, there is no illustrative disclosure on a compound having a monoalkylamino group at the adjusting position of amido group on the aryl.

In addition, 2-aminobenzamide derivatives having a bicyclic hetero ring on the nitrogen atom of amide group have been reported (Patent References 9 to 12). However, though angiogenesis inhibitory action and the like based on VEGF inhibition are disclosed in all of the references, there is no description on VR1 receptor and description on the application to pain. In addition, there is no disclosure in any of the official gazettes on a compound in which a monocyclic ring is directly bonded to the 2-position amino group without mediating an alkylene chain.

Patent Reference 1: International Publication No. 2004/108133

Patent Reference 2: International Publication No. 2004/072069

Patent Reference 3: International Publication No. 2005/072681

Patent Reference 4: US Patent Application Publication No. 2005/0165028

Patent Reference 5: International Publication No. 2004/069792

Patent Reference 6: International Publication No. 2006/038871

Patent Reference 7: International Publication No. 2004/110986

Patent Reference 8: Japanese Patent No. 3013989

Patent Reference 9: International Publication No. 2004/005279

Patent Reference 10: International Publication No. 2004/007457

Patent Reference 11: International Publication No. 2004/007458

Patent Reference 12: International Publication No. 2001/085671

DISCLOSURE OF THE INVENTION

Problems that the Invention is to Solve

The problems for the present invention is to provide a novel and excellent agent for treating or preventing nociceptive pain, neuropathic pain, cancer pain, headache, bladder function disorder and the like, based on inhibitory action on the capsaicin receptor VR1 activation.

Means for Solving the Problems

As a result of intensive studies on compounds having inhibitory action on VR1 activation, the present inventors have found that a benzamide derivative having a benzene ring in which a monocyclic ring is condensed on the nitrogen atom of amido group and having a lower alkylamino or an amino group substituted with a ring group at the neighboring position of said amido group is possessed of a potent inhibitory action on VR1 activation and excellent pharmacological action based on this and can become an excellent agent for treating or preventing VR1-involved diseases such as nociceptive pain, neuropathic pain, cancer pain, headache, bladder function disorder and the like, thereby accomplishing the present invention.

The pharmacological action of the compound represented by a general formula (I) as the active ingredient of the present invention is analgesic action by regulating the function of the VR1 receptor. Accordingly, its action is different from that of the aforementioned compound of Patent Reference 8 which is a nociceptin antagonist. Also, the compound as the active ingredient of the present invention is also different from that of the illustrative compounds described in the aforementioned Patent Reference 8 in terms of structural characteristics. That is, there is no illustrative disclosure in the aforementioned Patent Reference 8 on a benzamide derivative having a lower alkylamino or an amino group substituted with a ring group at its neighboring position, and the characteristic of the substituent group substituted on the ring A is also different. In addition, pharmacological action of the compound as the active ingredient of the present invention is also different from the compounds of the aforementioned Patent References 9 to 12 having VEGF inhibitory action.

That is, the present invention relates to a VR1 activation inhibitor which comprises a 2-aminobenzamide derivative represented by the following general formula (I) or a salt thereof as an active ingredient (I)

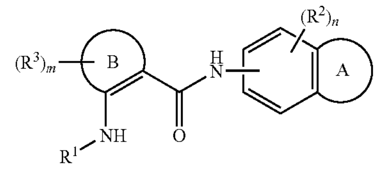

(symbols in the formula have the following meanings:

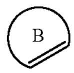:

benzene ring or pyridine ring, $R^3$: the same or different from each other and each represents H, halogen, halogeno-lower alkyl, cyano, nitro, lower alkyl, —$NR^4R^5$, -lower alkylene-$NR^4R^5$, -lower alkylene-$NR^6$—$CO_2$-lower alkyl, —O-lower alkyl, —O-halogeno-lower alkyl, phenyl or thienyl, m: 1, 2 or 3, $R^4$ and $R^5$: the same or different from each other and each represents H or lower alkyl, wherein $R^4$ and $R^5$ may be combined with the adjacent nitrogen atom to form a monocyclic nitrogen-containing saturated hetero ring which may be substituted with lower alkyl or lower alkylene-OH, $R^6$: H or lower alkyl,

:

monocyclic hetero ring, cycloalkene or benzene ring, wherein the ring represented by A may be substituted with 1 to 4 groups selected from —OH, -lower alkylene-OH, -lower alkylene-$NR^4R^5$, -lower alkylene-CO—$NR^4R^5$, halogen, halogeno-lower alkyl, lower alkyl and oxo, $R^1$: lower alkyl, -L-cycloalkyl, -L-cycloalkenyl, -L-monocyclic oxygen-containing saturated hetero ring, -L-monocyclic nitrogen-containing saturated hetero ring, -L-bridged-type nitrogen-containing saturated hetero ring, -L-phenyl or -L-pyridyl, with the proviso that, as the type of the ring A when $R^1$ is lower alkyl, it means a ring which forms indoline, tetrahydroquinoline or 3,4-dihydro-2H-1,4-benzoxazine together with the benzene ring to which it condenses, wherein the lower alkyl of $R^1$ may be substituted with 1 to 3 groups selected from the groups shown in the following group G, and the cycloalkyl, cycloalkenyl, monocyclic oxygen-containing saturated hetero ring, monocyclic nitrogen-containing saturated hetero ring, phenyl and pyridyl of $R^1$ may be substituted with 1 to 5 groups selected from the groups shown in the following group G and lower alkyl which may be substituted with a group shown in group G, Group G: —O-lower alkyl, —OH, oxo, —$S(O)_p$-lower alkyl, —$NR^4R^5$, —$NR^6$—$CO_2$-lower alkyl, —$NR^6$—$SO_2$-lower alkyl, —$N^+$(lower alkyl)$_3$, —$CO_2$-lower alkyl, —CO—$NR^4R^5$, halogen, phenyl, cycloalkyl, —O-lower alkylene-phenyl, —$NR^6$-cycloalkyl and monocyclic oxygen-containing saturated hetero ring, p: 0, 1 or 2, L: bond or lower alkylene, $R^2$: the same or different from each other and each represents H, lower alkyl, halogen, halogeno-lower alkyl or —OH, and n: 1 or 2. The symbols to be used in the description of Production Examples which are described later represent the same meanings).

In addition, the present invention also relates to a novel 2-aminobenzamide derivative represented by the following general formula (I') or a salt thereof, which has inhibitory action on VR1 activation and is useful as an agent for treating or preventing diseases in which VR1 receptor is involved, such as nociceptive pain, neuropathic pain, cancer pain, headache, bladder function disorder and the like.

Though some of said compounds are generally included in the present inventions of the aforementioned Patent References 1 to 4, there are no illustrative disclosure in said Patent References on the a benzamide derivative having a lower alkylamino or an amino group substituted with a ring group at the neighboring position of the amido group, which is a characteristic of the compound of the present invention, and also there is no description showing that the substituent group at the neighboring position of the amido group is important. In addition, structure of the compound of the present invention is different from that of the compound of the aforementioned Patent Reference 5 in which a hetero ring is directly bonded on the nitrogen atom, in terms that a monocyclic ring-condensed benzene ring is substituted on said amido nitrogen atom. A compound having lower alkylamino group at the 2-position of benzamide is disclosed in the aforementioned Patent Reference 6 which was laid open to public inspection after an application as the basis of the priority of the instant application, but said compound is different from the compound of the present invention in terms of the condensed ring structure on the amido nitrogen atom. In addition, structure of the compound of the aforementioned Patent Reference 7 is different from the compound of the present invention in terms of the essential groups: a ring structure at the 4-position of benzamide for Patent Reference 7, whereas 2-amino group for the present invention.

That is, the present invention relates to a novel 2-aminobenzamide derivative represented by the following general formula (I').

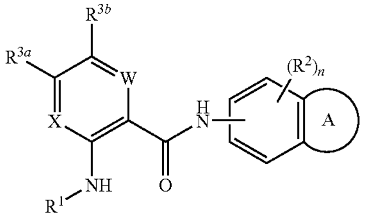

(I')

(symbols in the formula have the following meanings:
X and W: one is N and the other is CH, or both are CH,
$R^{3a}$ and $R^{3b}$: the same or different from each other and each represents H, halogen, halogeno-lower alkyl, cyano, nitro, lower alkyl, —$NR^4R^5$, -lower alkylene-$NR^4R^5$, -lower alkylene-$NR^6$—$CO_2$-lower alkyl, —O-lower alkyl, —O-halogeno-lower alkyl, phenyl or thienyl,
$R^4$ and $R^5$: the same or different from each other and each represents H or lower alkyl, wherein $R^4$ and $R^5$ may be combined with the adjacent nitrogen atom to form a monocyclic nitrogen-containing saturated hetero ring which may be substituted with lower alkyl or lower alkylene-OH,
$R^6$: H or lower alkyl,

:

monocyclic hetero ring, cycloalkene or benzene ring, wherein the ring represented by A may be substituted with 1 to 4 groups selected from —OH, -lower alkylene-OH, -lower alkylene-$NR^4R^5$, -lower alkylene-CO—$NR^4R^5$, halogen, halogeno-lower alkyl, lower alkyl and oxo,
$R^1$: lower alkyl, cycloalkyl, cycloalkenyl, monocyclic oxygen-containing saturated hetero ring, monocyclic nitrogen-containing saturated hetero ring, phenyl or pyridyl, with the proviso that, as the type of the ring A when $R^1$ is lower alkyl, it means a ring which forms indoline, tetrahydroquinoline or 3,4-dihydro-2H-1,4-benzoxazine together with the benzene ring to which it condenses,
wherein the lower alkyl of $R^1$ may be substituted with 1 to 3 groups selected from the groups shown in the following group G, and the cycloalkyl, cycloalkenyl, monocyclic oxygen-containing saturated hetero ring, monocyclic nitrogen-containing saturated hetero ring, phenyl and pyridyl of $R^1$ may be substituted with 1 to 5 groups selected from the groups shown in the following group G and lower alkyl which may be substituted with a group shown in group G,
Group G: —O-lower alkyl, —OH, oxo, —$S(O)_p$-lower alkyl, —$NR^4R^5$, —$NR^6$—$CO_2$-lower alkyl, —$NR^6$—$SO_2$-lower alkyl, —$N^+$(lower alkyl)$_3$, —$CO_2$-lower alkyl, —CO—$NR^4R^5$, halogen, phenyl, cycloalkyl, —O-lower alkylene-phenyl, —$NR^6$-cycloalkyl and monocyclic oxygen-containing saturated hetero ring,
p: 0, 1 or 2,
$R^2$: the same or different from each other and each represents H, lower alkyl, halogen, halogeno-lower alkyl or —OH, and
n: 1 or 2).

Also, the present invention relates to a pharmaceutical composition, which comprises a 2-aminobenzamide derivative represented by the aforementioned general formula (I') or a salt thereof and a pharmaceutically acceptable carrier. Preferably, the aforementioned pharmaceutical composition which is a VR1 activation inhibitor, more preferably the aforementioned pharmaceutical composition which is an agent for treating or preventing nociceptive pain, neuropathic pain, cancer pain, headache and bladder function disorder.

In addition, other embodiments of the present invention are use of a 2-aminobenzamide derivative represented by the aforementioned general formula (I') or a salt thereof, and a method for preventing or treating nociceptive pain, neuropathic pain, cancer pain, headache and bladder function disorder, which comprises administering an effective amount of the 2-aminobenzamide derivative or a salt thereof to a mammal.

EFFECT OF THE INVENTION

The compound as the active ingredient of the pharmaceutical preparations of the present invention has the advantage of having strong inhibitory action on the capsaicin receptor VR1 activation and good pharmacological action based thereon. The pharmaceutical composition of the present invention is useful for the treatment or prevention of diseases in which VR1 is involved, particularly for the treatment or prevention of nociceptive pain, neuropathic pain, cancer pain, headache and bladder function disorder.

BEST MODE FOR CARRYING OUT THE INVENTION

The following describes the present invention in detail.

In this description, the “VR1 activation inhibitor” is a compound which binds to the VR1 receptor, and is a general term for a compound which inhibits activation of VR1 by competing with an intrinsic ligand (VR1 antagonist) and a compound which desensitizes the nerve where said receptor is present by the persistent activation of the VR1 receptor and inhibits the activation thereafter (VR1 agonist). Preferred as the “VR1 activation inhibitor” is a VR1 antagonist.

Regarding the definition of the formulae in the description, the term “lower” means a straight or branched carbon chain having from 1 to 6 carbon atoms (to be referred to as $C_{1-6}$ hereinafter) unless otherwise noted. Thus, the “lower alkyl” is a $C_{1-6}$ alkyl, preferably straight chain alkyl such as methyl, ethyl, n-propyl, n-butyl group or the like or branched alkyl such as isopropyl, isobutyl, tert-butyl, neopentyl group or the like. A $C_{1-4}$alkyl is more preferable, and methyl, ethyl, n-propyl, isopropyl and tert-butyl group are particularly preferable. The “lower alkylene” is a $C_{1-6}$ alkylene, preferably straight chain alkylene such as methylene, ethylene, trimethylene, tetramethylene group or the like or branched alkylene such as propylene, ethylethylene, 1,2-dimethylethylene, 1,1,2,2-tetramethylethylene group or the like. A $C_{1-4}$ alkylene is more preferable.

The “halogen” means F, Cl, Br and I. Particularly, F and Cl are preferable. The “halogeno-lower alkyl” means a $C_{1-6}$ alkyl substituted with 1 or more halogen, which is preferably a $C_{1-6}$ alkyl substituted with 1 or more F, and more preferably trifluoromethyl group.

The “cycloalkyl” is a $C_{3-10}$ saturated hydrocarbon ring group which may have a bridge. Preferred is a $C_{3-8}$ cycloalkyl, more preferred are cyclopropyl, cyclobutyl, cyclopentyl, cyclohexyl, cycloheptyl, cyclooctyl and adamantyl groups, particularly preferred are cyclopentyl, cyclohexyl and cycloheptyl groups.

The “cycloalkenyl” is a ring group having a double bond in a part of the ring of the aforementioned “cycloalkyl”, preferably a $C_{3-8}$ cycloalkenyl, more preferably cyclopentenyl and cyclohexenyl.

The "monocyclic nitrogen-containing saturated hetero ring" means a 5- to 8-membered saturated or partially unsaturated monocyclic hetero ring group which contains one N atom and may further contain one of hetero atoms consisting of N, S and O. Preferred are pyrrolidinyl, piperidyl, piperazinyl, azepanyl, diazepanyl, azocanyl, morpholinyl, thiomorpholinyl and tetrahydropyridinyl groups. Particularly preferred are pyrrolidinyl, piperidyl and morpholinyl groups.

The "bridged-type nitrogen-containing hetero ring" is a bridged ring group in which optional two carbon atoms at un-adjacent positions in the aforementioned "monocyclic nitrogen-containing saturated hetero ring" are bonded via an alkylene chain, which may contain a double bond in the ring. Preferred are quinuclidinyl, 8-azabicyclo[3.2.1]octenyl and 7-azabicyclo[2.2.1]heptanyl.

In the aforementioned "monocyclic nitrogen-containing saturated hetero ring", the ring atom S may be oxidized to form oxide or dioxide or N may be oxidized to form oxide.

The "monocyclic oxygen-containing saturated hetero ring" is a 5- to 7-membered saturated monocyclic hetero ring group containing 1 or 2 O atoms, preferably tetrahydrofuranyl, tetrahydropyranyl and 1,4-dioxanyl.

The "monocyclic hetero ring" of ring A is a 5- or 6-membered unsaturated or partially unsaturated monocyclic hetero ring group containing 1 or 2 hetero atoms consisting of N, S and O, which is a ring having a double bond at a position where said ring is condensed with benzene ring. Preferred are 2,3-dihydro-1H-pyrrole, 2,5-dihydro-1H-pyrrole, 1,2,3,4-tetrahydropyridine, 1,2,3,6-tetrahydropyridine, 2,3-dihydro-1,4-dioxine, 3,4-dihydro-2H-1,4-oxazine, 3,4-dihydro-2H-1,4-thiazine, 1,2-dihydropyridine, pyrrole, pyran, pyrazole, thiophene, oxazole, thiazole, pyridine, 1,3-dioxole and 6,7-dihydro-5H-1,4-dioxepine ring, and are ring groups wherein said ring groups are condensed with benzene ring to form indoline, isoindoline, tetrahydroquinoline, tetrahydroisoquinoline, 2,3-dihydro-1,4-benzodioxine, 3,4-dihydro-2H-1,4-benzoxazine, 3,4-dihydro-2H-1,4-benzothiazine, 1,2-dihydroquinoline, 2,3-dihydroisoquinoline, indole, benzopyran, indazole, benzothiophene, benzoxazole, benzothiazole, quinoline, isoquinoline, 1,3-benzodioxole and 3,4-dihydro-2H-1,5-benzodioxepine ring.

The "monocyclic nitrogen-containing hetero ring" of ring A is a ring group containing at least one nitrogen atom as the ring atom among the aforementioned "monocyclic hetero ring", and preferred of which are 2,3-dihydro-1H-pyrrole, 1,2,3,4-tetrahydropyridine, 3,4-dihydro-2H-1,4-oxazine and 1,2-dihydropyridine ring, and particularly preferred are 2,3-dihydro-1H-pyrrole, 1,2,3,4-tetrahydropyridine and 3,4-dihydro-2H-1,4-oxazine ring.

The "cycloalkene" of ring A is a $C_{5-8}$ hydrocarbon ring, which is a ring that has a double bond at a position where said ring is condensed with benzene ring. It may have another double bond in the other ring. Preferred are cyclopentene, cyclopentadiene, cyclohexene and cycloheptene rings, and more preferred is cyclohexene ring.

Preferred as the group represented by $R^3$ are H, halogen, halogeno-lower alkyl and nitro, and more preferred are halogen and halogeno-lower alkyl. The substitution position is preferably the 4-position or 5-position, more preferably the 4-position.

When a compound have two or more groups of other than H as the group represented by $R^3$, said substituent groups may be the same or different from one another.

Preferred as the group represented by $R^1$ are -L-cycloalkyl, -L-monocyclic oxygen-containing saturated hetero ring and -L-monocyclic nitrogen-containing saturated hetero ring, and more preferred are -L-cycloalkyl and -L-monocyclic oxygen-containing saturated hetero ring. A bond is desirable as L. Said ring group may be substituted with 1 to 5 groups selected from lower alkyl, the groups shown by group G and lower alkyl substituted with the groups shown by group G.

Preferred as the substituent group shown by group G is $—NR^4R^5$ or cycloalkyl, more preferred is $—NR^4R^5$ and further preferred is a group which is a monocyclic nitrogen-containing saturated hetero ring in which $R^4$ and $R^5$ is combined together with the adjacent nitrogen atom.

The $R^4$, $R^5$ and $R^6$ contained in the groups shown in the group G and the $R^4$, $R^5$ and $R^6$ contained in the group represented by $R^3$ are each independent and may be different from one another.

When the group represented by $R^1$ is -L-cycloalkyl, wherein said ring group is substituted with lower alkyl and $—NR^4R^5$ on the same carbon atom, said lower alkyl and $R^4$ may be bonded to form a ring.

A preferred embodiment of the 2-aminobenzamide derivative represented by the general formula (I) as the active ingredient of the present invention is the derivatives of the following (A1) to (A3) and the derivatives represented by the aforementioned general formula (I').

(A1) A derivative in which A is a monocyclic nitrogen-containing hetero ring wherein said ring group has oxo group or hydroxyl group as the substituent group and may be further substituted with 1 or 2 groups selected from -lower alkylene-OH, -lower alkylene-$NR^4R^5$, -lower alkylene-CO—$NR^4R^5$, halogen, halogeno-lower alkyl and lower alkyl.

(A2) More preferred is a derivative described in the aforementioned (A1), wherein type of the ring A is one which forms indoline, tetrahydroquinoline, 3,4-dihydro-2H-1,4-benzoxazine or 1,2-dihydroquinoline together with the benzene ring to which it is condensed.

(A3) More preferred is a derivative described in the aforementioned (A1), wherein type of the ring A is one which forms indoline, tetrahydroquinoline or 3,4-dihydro-2H-1,4-benzoxazine together with the benzene ring to which it is condensed.

A preferred embodiments of the 2-aminobenzamide derivative as the compound of the present invention represented by the general formula (I') is the following derivatives.

(B1) A derivative in which X is N or CH, W is CH and A is a monocyclic nitrogen-containing hetero ring, wherein said ring group has oxo group or hydroxyl group as the substituent group and may be further substituted with 1 or 2 groups selected from -lower alkylene-OH, -lower alkylene-$NR^4R^5$, -lower alkylene-CO—$NR^4R^5$, halogen, halogeno-lower alkyl and lower alkyl.

(B2) More preferred is a derivative described in the aforementioned (B1), wherein type of the ring A is one which forms indoline, tetrahydroquinoline, 3,4-dihydro-2H-1,4-benzoxazine or 1,2-dihydroquinoline together with the benzene ring to which it is condensed.

(B3) More preferred is a derivative described in the aforementioned (B2), wherein type of the ring A is one which forms indoline, tetrahydroquinoline or 3,4-dihydro-2H-1,4-benzoxazine together with the benzene ring to which it is condensed.

(B4) More preferred is a derivative described in the aforementioned (B3), which is a ring group wherein $R^1$ is selected from cycloalkyl, cycloalkenyl, monocyclic oxygen-containing saturated hetero ring and monocyclic nitrogen-containing saturated hetero ring, that may be substituted with 1 to 5 groups selected from the groups shown by group G and lower alkyl which may be substituted with the groups shown by group G.

(B5) More preferred is a derivative described in the aforementioned (B4), which is a ring group wherein $R^1$ is selected from cycloalkyl, dioxolanyl and piperidyl, that may be substituted with lower alkyl, —$NR^4R^5$ or cycloalkyl.

Another preferred embodiment of the 2-aminobenzamide derivative represented by the compound of the present invention (I') is the following derivatives.

(C1) More preferred is a derivative described in the aforementioned (B1), which is a ring group wherein $R^1$ is selected from cycloalkyl, cycloalkenyl, monocyclic oxygen-containing saturated hetero ring, monocyclic nitrogen-containing saturated hetero ring, phenyl and pyridyl, that may be substituted with 1 to 5 groups selected from the groups shown by group G and lower alkyl which may be substituted with the groups shown by group G.

(C2) More preferred is a derivative described in the aforementioned (C1), which is a ring group wherein $R^1$ is selected from cycloalkyl and piperidyl, that may be substituted with lower alkyl, —$NR^4R^5$ or cycloalkyl.

Particularly preferred among the 2-aminobenzamide derivatives represented by the compound of the present invention (I') are derivatives selected from the group consisting of 4-chloro-N-(1-methyl-2-oxo-1,2,3,4-tetrahydroquinolin-7-yl)-2-{[(1S,2S)-2-pyrrolidin-1-ylcyclohexyl]amino}benzamide, 2-(cyclohexylamino)-N-(2-methyl-3-oxo-3,4-dihydro-2H-1,4-benzoxazin-6-yl)-4-(trifluoromethyl)benzamide, 4-chloro-N-[(2R)-2-methyl-3-oxo-3,4-dihydro-2H-1,4-benzoxazin-6-yl]-2-{[(1R,2S)-2-pyrrolidin-1-ylcyclohexyl]amino}benzamide, N-[2-oxo-4-(trifluoromethyl)2,3-dihydro-1H-indol-6-yl]-2-{[(1S,2S)-2-pyrrolidin-1-ylcyclohexyl]amino}-4-(trifluoromethyl)benzamide, N-(1-methyl-2-oxo-1,2,3,4-tetrahydroquinolin-7-yl)-2-(pyridin-4-ylamino)-4-(trifluoromethyl)benzamide, N-(3,3-dimethyl-2-oxo-2,3-dihydro-1H-indol-6-yl)-2-{[(1S,2S)-2-pyrrolidin-1-ylcyclohexyl]amino}-4-(trifluoromethyl)benzamide, N-(3,3-dimethyl-2-oxo-2,3-dihydro-1H-indol-6-yl)-2-{[(1R,2R)-2-pyrrolidin-1-ylcyclohexyl]amino}-4-(trifluoromethyl)benzamide, 2-{[(1R,2R)-2-(dimethylamino)cyclohexyl]amino}-N-[(2R)-2-methyl-3-oxo-3,4-dihydro-2H-1,4-benzoxazin-6-yl]-4-(trifluoromethyl)benzamide, 2-{[(1S,2S)-2-(dimethylamino)cyclohexyl]amino}-N-(3,3-dimethyl-2-oxo-2,3-dihydro-1H-indol-6-yl)-4-(trifluoromethyl)benzamide, N-(3,3-dimethyl-2-oxo-2,3-dihydro-1H-indol-6-yl)-2-[(1-isobutylpiperidin-4-yl)amino]-4-(trifluoromethyl)benzamide, N-(3,3-dimethyl-2-oxo-2,3-dihydro-1H-indol-6-yl)-2-{[(3S)-1-pentylpyrrolidin-3-yl]amino}-4-(trifluoromethyl)benzamide, N-(2-oxo-1,2-dihydroquinolin-7-yl)-2-{[(1R,2R)-2-pyrrolidin-1-ylcyclohexyl]amino}-4-(trifluoromethyl)benzamide, N-(3,3-dimethyl-2-oxo-2,3-dihydro-1H-indol-6-yl)-2-{[(3S)-1-pentylpyrrolidin-3-yl]amino}-4-(trifluoromethyl)benzamide, 2-[(1-butylpiperidin-4-yl)amino]-N-(3,3-dimethyl-2-oxo-2,3-dihydro-1-H-indol-6-yl)-4-(trifluoromethyl)benzamide, N-(3,3-dimethyl-2-oxo-2,3-dihydro-1H-indol-6-yl)-2-{[(1S,2R)-2-pyrrolidin-1-ylcyclohexyl]amino}-4-(trifluoromethyl)benzamide, 2-{[(1S,2R)-2-pyrrolidin-1-ylcyclohexyl]amino}-N-quinolin-7-yl-4-(trifluoromethyl)benzamide, 2-{[(1S,2S)-2-pyrrolidin-1-ylcyclohexyl]amino}-N-quinolin-7-yl-4-(trifluoromethyl)benzamide, and N-[2-oxo-4-(trifluoromethyl)-2,3-dihydro-1H-indol-6-yl]-2-{[(1S,2R)-2-pyrrolidin-1-ylcyclohexyl]amino}-6-(trifluoromethyl)nicotinamide.

Also, depending on the kind of substituent groups, stereoisomers, tautomers, optical isomers and the like are sometimes present in the compound represented by the general formula (I) which is the active ingredient of the present invention (to be referred to as compound (I) hereinafter), and mixtures and isolated forms of these isomers are included in the present invention.

In addition, "pharmaceutically acceptable prodrugs" regarding the compound (I) are also included in the present invention. The "pharmaceutically acceptable prodrug" is a compound which can produce the compound (I) by being converted into the group such as $CO_2H$, $NH_2$, OH or the like by solvolysis or under a physiological condition. As the groups which form prodrugs, the groups described in *Prog. Med.,* 5, 2157-2161 (1985) and "Iyakuhin no Kaihatsu (Development of Medicines)" (Hirokawa Shoten, 1990) Vol. 7 Bunshi Sekkei (Molecular Design) 163-198 can be cited.

As salts of the compound (I), they are pharmaceutically acceptable salts, and illustratively, acid addition salts with inorganic acids (e.g., hydrochloric acid, hydrobromic acid, hydroiodic acid, sulfuric acid, nitric acid, phosphoric acid and the like), with organic acids (e.g., formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, aspartic acid, glutamic acid and the like), and the like may be exemplified. In addition, there are cases of forming salts with bases depending on the kind of substituent groups, and for example, salts with inorganic bases including metals (e.g., sodium, potassium, magnesium, calcium, aluminum, lithium and the like), with organic bases (e.g., methylamine, ethylamine, ethanolamine, lysine, ornithine and the like), ammonium salts and the like may be cited.

Further, various hydrates and solvates and polymorphic crystals are included in the compound (I) and salts thereof.

(Production Methods)

The compound (I) as the active ingredient of the present invention can be produced by applying various conventionally known synthetic methods making use of its basal backbone or the characteristics based on the kind of substituent groups. In that case, depending on the kind of a functional group, there is a case in which protection of said functional group by an appropriate protecting group or replacement of a group which can be easily converted into said functional group, at a stage of the materials to intermediates, is effective in view of the production techniques. As such a functional group, it includes amino group, hydroxyl group, carboxyl group and the like, as their protecting groups, the protecting groups described for example in "Protective Groups in Organic Synthesis", edited by T. W. Greene and P. G. M. Wuts, 3rd edition, 1999, can be cited, and these may be optionally selected and used in response to the reaction conditions. By such a method, a desired compound can be obtained by carrying out the reaction by introducing said protecting group and then removing the protecting group as occasion demands or converting it into a desired group.

In addition, a prodrug of the compound (I) or a salt thereof can be produced by introducing a specific group at a stage of the materials to intermediates similar to the case of the aforementioned protecting group or by carrying out the reaction using the obtained compound (I). The reaction can be carried out by employing the general methods which are known by those skilled in the art, such as esterification, amidation, acylation and the like.

(First Production Method)

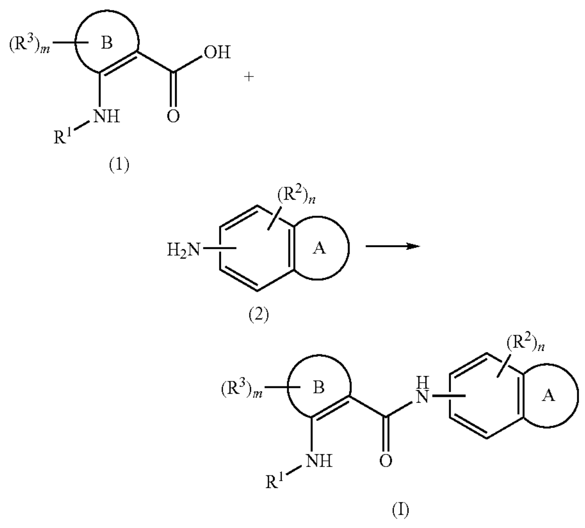

(1)

(2)

(I)

The first production method is a method in which the compound (I) of the present invention is produced by an amido condensation reaction using a compound (1) and a compound (2).

This reaction is carried out by using the compound (1) and compound (2) in equivalent amounts, or one of them in an excess amount, and allowing them to undergo the reaction under ice-cooling to under heating for generally from 0.1 hour to 5 days in a reaction inert solvent in the presence of a condensing agent. As the condensing agent, condensing agents described in "Jikken Kakagu Koza (Experimentation Chemistry Course)", edited by The Chemical Society of Japan, 4th edition, Maruzen, 1992, vol. 22, ibid., 5th edition, Maruzen, 2005, vol. 16, and "Comprehensive Organic Synthesis", (England), edited by B. M. Trost and I. Fleming, Pergamon Press, 1991, vol. 6, N,N-dicyclohexylcarbodiimide (DCC), 1-ethyl-3-[3-(N,N-dimethylamino)propyl]carbodiimide, O-benzotriazol-1-yl-N,N,N',N'-tetramethyluronium hexafluorophosphate (HBTU), N-[(dimethylamino)(3H-1,2,3)triazolo[4,5-b]pyridin-3-yloxy]methylene]-N-methylmethanammonium hexafluorophosphate (HATU), carbonyldiimidazole, diphenylphosphoryl azide (DPPA) and the like, may be suitably used. These condensing agents are used in an equivalent amount or excess amount based on the carboxylic acid. The solvent is not particularly limited and, for example, aromatic hydrocarbons (e.g., benzene, toluene, xylene and the like), ethers (e.g., diethyl ether, tetrahydrofuran (THF), 1,4-dioxane, 1,2-dimethoxyethane, 1,2-diethoxyethane and the like), halogenated hydrocarbons (e.g., dichloromethane, 1,2-dichloroethane, chloroform and the like), alcohols (e.g., methanol, ethanol, 2-propanol, butanol and the like), N,N-dimethylformamide (DMF), N-methylpyrrolidone (NMP), dimethyl sulfoxide (DMSO), water or mixed solvents thereof, and the like, may be cited. In this connection, the reaction smoothly progresses in some cases when the reaction is carried out in the presence of a base such as N-methylmorpholine, triethylamine, trimethylamine, pyridine, 4-dimethylaminopyridine or the like, or using these bases in a solvent volume.

In addition, the compound (I) can also be produced by a method in which the carboxylic acid compound (1) is converted into an active derivative and then condensed with the amine compound (2). Also in this case, the reaction can be carried out under the same conditions of the aforementioned reaction in which the compound (1) is allowed to undergo the reaction directly using equivalent amounts of the compound (1) and compound (2), or using one of them in an excess amount. In this case, as the active derivative of carboxylic acid, an active ester obtained by allowing to react with a phenol system compound (p-nitrophenol or the like) or an N-hydroxyamine system compound (1-hydroxysuccinimide, 1-hydroxybenzotriazole or the like), a mixed acid anhydride obtained by reacting with an organic acid, a phosphoric acid system acid anhydride obtained by allowing to react with diphenylphosphoryl chloride and N-methylmorpholine, an acid azide obtained by allowing the ester to react with hydrazine and an alkyl nitrite in succession, an acid halide (e.g., acid chloride, acid bromide or the like), a symmetric acid anhydride and the like may be exemplified. The activation reagents and reaction conditions for converting the aforementioned active derivatives from the carboxylic acid compound (1) are described for example in "Jikken Kakagu Koza (Experimentation Chemistry Course)", edited by The Chemical Society of Japan, 4th edition, Maruzen, 1992, vol. 22, ibid., 5th edition, Maruzen, 2005, vol. 16, "Compendium of Organic Synthetic Methods", (USA), edited by I. T. Harrison and S. Harrison, Wily Interscience, 1971, vol. 1, and ibid., 1974, vol. 2, "Compendium of Organic Synthetic Methods", (USA), edited by L. S. Hegedus and L. G. Wade, Wily Interscience, 1977, vol. and the like, and it can be carried out with reference to said methods.

(Second Production Method)

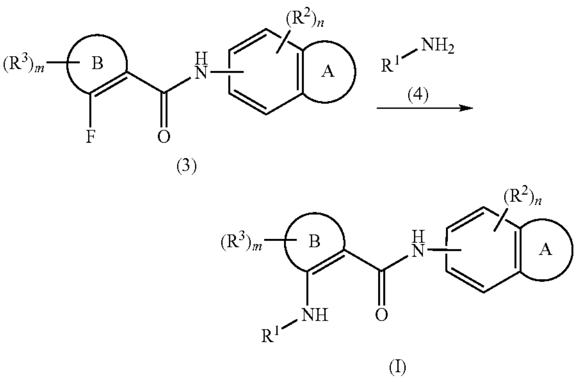

(4)

(3)

(I)

The second production method is a method in which the compound (I) of the present invention is produced by substituting a compound (4) with a compound (3). This reaction is carried out by using the compound (3) and compound (4) in equivalent amounts, or one of them in an excess amount, and allowing them to undergo the reaction under ice-cooling to under heating for generally from 0.1 hour to 5 days in a reaction inert solvent in the presence of a base. As the base, organic bases such as pyridine, diisopropylethylamine, triethylamine, 2,6-lutidine and the like may be used, as well as the other bases such as potassium carbonate, sodium bicarbonate, cesium carbonate, sodium hydride, potassium tert-butoxide and the like. The reaction can be carried out for example by optionally selecting the reaction conditions and the like described in J. Am. Chem. Soc., 1949, 71, 740-741, J. Org. Chem., 1994, 59(21), 6194-6199, J. Med. Chem., 2004, 47(19), 4642-4644 and Chem. Pharm. Bull., 1996, 47(1), 28-36.

(Third Production Method)

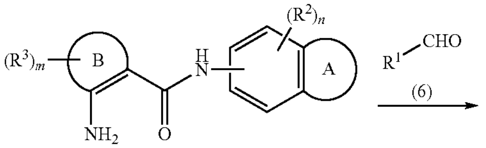

(5)

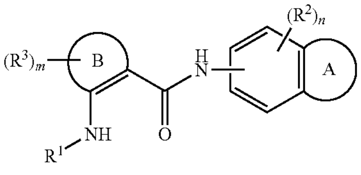

(I)

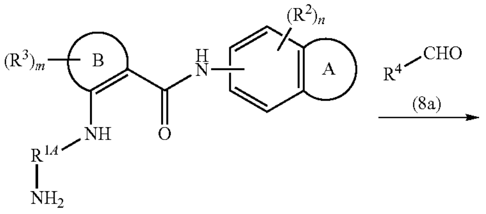

(7)

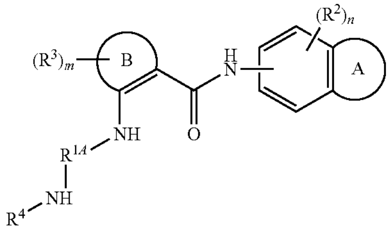

(Ia)

(Ia)

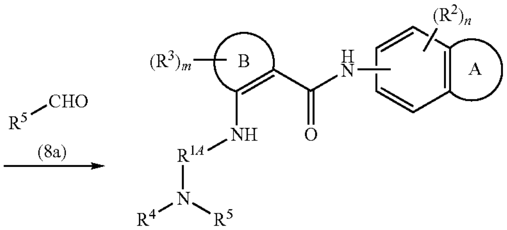

(Ib)

(In the formulae, $R^{1A}$ represents a divalent group formed by removing hydrogen atom from a group selected from lower alkyl, -L-cycloalkyl, -L-cycloalkenyl, -L-monocyclic oxygen-containing saturated hetero ring, -L-monocyclic nitrogen-containing saturated hetero ring and -L-phenyl. Also, $R^{4a}$ and $R^{5a}$ may be the same or different from each other and each represents lower alkyl, or together lower alkylene, group. The same shall apply hereinafter.)

The third production method is a method in which the compound (I) or (Ia) of the present invention is produced by a reductive alkylation reaction of a compound (5) with a compound (6) or a compound (7) with a compound (8a). This reaction is carried out by using the compound (5) and compound (6) or the compound (7) and compound (8a) in equivalent amounts, or one of them in an excess amount, and allowing them to undergo the reaction under ice-cooling to under heating for generally from 0.1 hour to 5 days in a reaction inert solvent in the presence of a reducing agent and a Lewis acid. As the reducing agent, a catalytic reduction condition may be used, as well as the stoichiometry-type reducing agents such as sodium triacetoxyborohydride, sodium borohydride, diborane, lithium aluminum hydride (LAH), and the like.

The compound (Ib) of the present invention can be produced by further allowing the compound (Ia) produced by this method to react with a compound (8b).

For the reductive alkylation reaction, for example, the reaction conditions described in "Jikken Kakagu Koza (Experimentation Chemistry Course)", edited by The Chemical Society of Japan, 4$^{th}$ edition, Maruzen, 1992, vol. 22, ibid., 5$^{th}$ edition, Maruzen, 2005, vol. 16, may be optionally selected and used.

(Fourth Production Method)

The compounds as the active ingredients of the pharmaceutical preparations of the present invention having various functional groups can also be produced by employing the methods obvious to those skilled in the art, conventionally known production methods or modified methods thereof. For example, desired compounds can be produced by further subjecting the compounds obtained by the aforementioned production methods to substituent group modification reactions. Typical reactions are shown in the following.

(1) Amidation and Esterification

Among the compounds (I), a compound having amido group or a compound having ester group can be produced by using a compound having amino group or hydroxyl group as the material and allowing it to react with a carboxylic acid or reactive derivative thereof. The reaction can be carried out by making reference to the methods described for example in "Jikken Kakagu Koza (Experimentation Chemistry Course)", edited by The Chemical Society of Japan, 4$^{th}$ edition, Maruzen, 1992, vol. 22, ibid., 5$^{th}$ edition, Maruzen, 2005, vol. 16, or the aforementioned "Compendium of Organic Synthetic Methods", vol. 1 to vol. 3 or the like.

(2) Oxidation

Among the compounds (I), a compound having sulfonyl group or sulfenyl group can be produced by an oxidation reaction of a compound having sulfide group. The reaction can be carried out by making reference to the methods described for example in "Jikken Kakagu Koza (Experimentation Chemistry Course)", edited by The Chemical Society of Japan, 4$^{th}$ edition, Maruzen, 1992, vol. 23, ibid., 5$^{th}$ edition, Maruzen, 2005, vol. 17, or the aforementioned "Compendium of Organic Synthetic Methods", vol. 1 to vol. 3 or the like.

(3) Alkylation

Among the compounds (I), a compound having a lower alkoxy group or a lower alkylamino group can be produced by subjecting a compound having hydroxyl group or amino group to an alkylation reaction. The reaction can be carried out by making reference to the methods described for example in "Jikken Kakagu Koza (Experimentation Chemistry Course)", edited by The Chemical Society of Japan, 4$^{th}$ edition, Maruzen, 1992, vol. 20, ibid., 5$^{th}$ edition, Maruzen, 2005, vol. 14, or the aforementioned "Compendium of Organic Synthetic Methods", vol. 1 to vol. 3 or the like.

(4) Amination and Alkoxylation Reactions by Substitution Reaction

Among the compounds (I), a compound having a lower alkoxy group or a lower alkylamino group can also be produced by substituting an alcohol or amine compound corresponding to a compound having halogen under a basic condition. The reaction can be carried out by optionally selecting and using the reaction conditions described for example in "Jikken Kakagu Koza (Experimentation Chemistry Course)"edited by The Chemical Society of Japan, 4$^{th}$ edition, Maruzen, 1992, vol. 20, and ibid., 5$^{th}$ edition, Maruzen, 2005, vol. 14.

(Production Methods of Material Compounds)

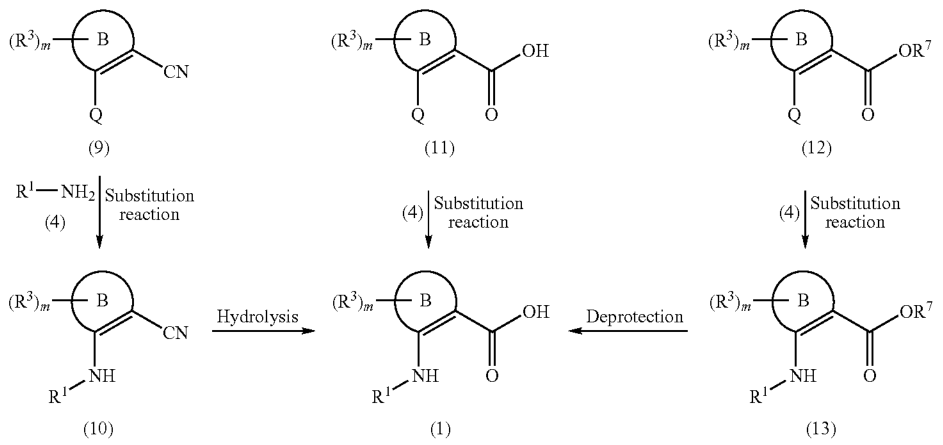

(In the formulae, Q represents F or Cl, and $R^7$ a carboxyl group-protecting group of lower alkyl, benzyl or the like, respectively. The same shall apply hereinafter.)

The material compound (1) in the aforementioned first production method can be produced by the reaction pathway described in the above.

In the reaction pathway described in the above, the substitution reaction can be carried out by making reference to the method described in "Jikken Kakagu Koza (Experimentation Chemistry Course)", edited by The Chemical Society of Japan, 4$^{th}$ edition, Maruzen, 1992, vol. 23 and the like, and the hydrolysis to the method described in "Jikken Kakagu Koza (Experimentation Chemistry Course)", edited by The Chemical Society of Japan, 4$^{th}$ edition, Maruzen, 1992, vol. 22 and the like, and the deprotection to the method described in "Protective Groups in Organic Synthesis", 3$^{rd}$ edition, 1999.

Regarding the material compound (1), a compound in which $R^3$ is halogen can be produced by allowing a halogenation agent such as N-chlorosuccinimide, N-bromosuccinimide, chlorine, iodine or the like to react with each intermediate in the reaction pathway described in the above wherein $R^3$ is hydrogen atom.

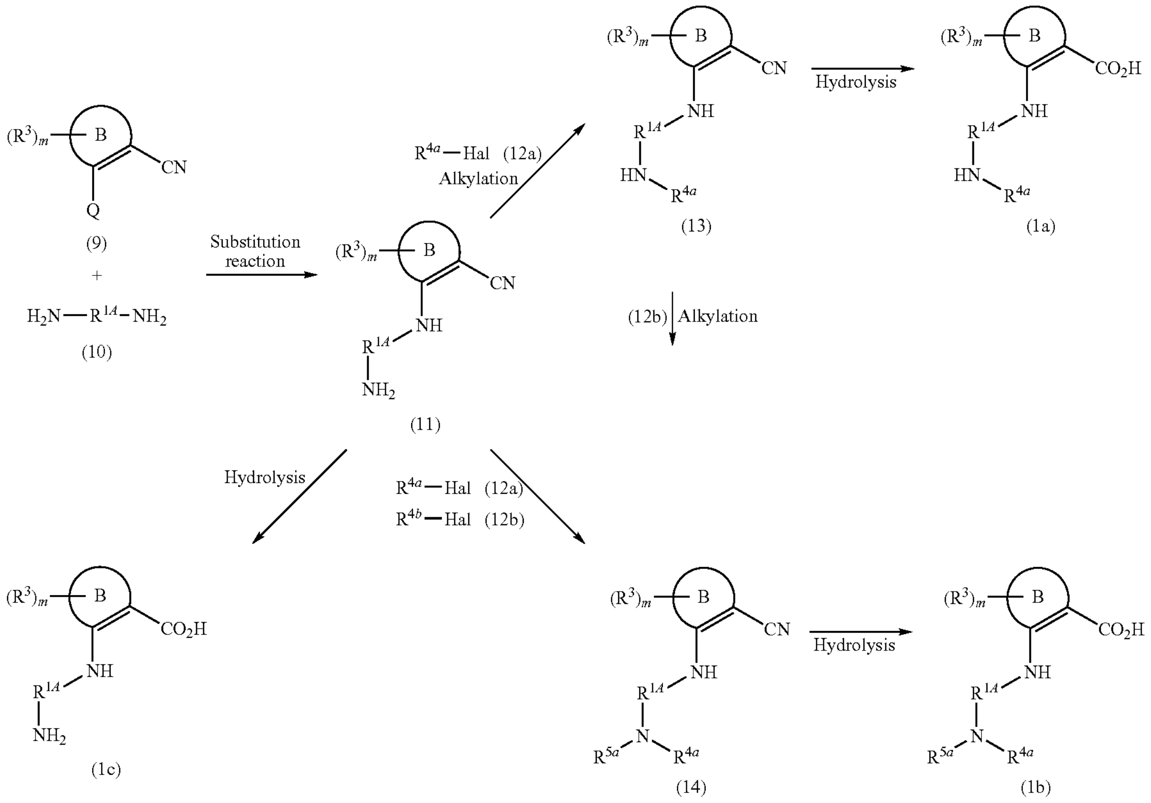

(In the Formulae, Hal Represents Halogen. The Same Shall Apply Hereinafter.)

The reaction pathway described in the above shows production methods of the material compounds (1), particularly those which have certain alkylamino group as $R^1$ on the terminus, namely a compound (1a) which has a group represented by $—R^{1A}—NHR^{4a}$, a compound (1b) which has a group represented by $—R^{1A}—NR^{4a}R^{5a}$ and a compound (1c) which has a group represented by $—R^{1A}—NH_2$.

In the reaction pathway described in the above, the substitution reaction can be carried out by making reference to the method described in "Jikken Kakagu Koza (Experimentation Chemistry Course)", edited by The Chemical Society of Japan, $4^{th}$ edition, Maruzen, 1992, vol. 23 and the like. Also, the alkylation can be carried out by making reference to the method described in "Jikken Kakagu Koza (Experimentation Chemistry Course)", edited by The Chemical Society of Japan, $4^{th}$ edition, Maruzen, 1992, vol. 20 and the like. The hydrolysis can be carried out by making reference to the method described in the aforementioned "Protective Groups in Organic Synthesis ($3^{rd}$ edition, 1999)".

Regarding the step for converting the compound (11) into compound (14) by alkylation in the reaction pathway described in the above, it is desirable to allow the compound (11) to react with the alkylating agents (12a) and (12b) through two steps, and in that case, it is desirable to allow the compound (11) to react with the alkylating agent (9) after once protecting its amino group with a protecting group and then to obtain the first step intermediate (13) by removing the protecting group. In addition, when $R^{4a}$ and $R^{5a}$ in the compound (14) form a monocyclic nitrogen-containing saturated hetero ring, as a pair together with the adjacent nitrogen atom, it is desirable to obtain the compound (14) by one step through the treatment of the compound (11) using an alkylating agent in which the alkylating agents (12a) and (12b) are formed into one body.

When the (1a) and (1c) produced by the production method described in the above are used as the materials of the first production method, it is desirable to protect the terminal amino group. It is desirable in some cases to carry out said protection at the stage of an intermediate in the production process described in the above.

The compound (I) produced in this manner is isolated and purified directly as its free form or as its salt by applying a salt formation treatment by a usual method. The isolation and purification are carried out by employing general chemical operations such as extraction, concentration, evaporation, crystallization, filtration, recrystallization, various types of chromatography, and the like.

Various types of isomers can be isolated by a general method making use of the difference in the physicochemical properties between isomers. For example, optical isomers can be respectively separated and purified by a general method in which a racemic compound is converted into diastereomer salts with an optically active organic acid (tartaric acid or the like) and then subjected to fractional crystallization, or a chiral filler-aided chromatography or the like. In addition, an optically active compound can also be produced using an appropriate optically active compound as the material. In this connection, a diastereomer mixture can also be separated by the fractional crystallization, chromatography or the like.

EXAMPLES

The following describes production methods of novel compounds which are included in the compound (I) as the active ingredient of the present invention, as examples. Also, production methods of novel compounds among the compounds used as materials are described as reference examples. In this connection, the production method of the compound (I) is not limited to the production methods of illustrative examples shown in the following, and thy can be also be produced by a combination of these production method or conventionally production methods.

In addition, the following abbreviations are used in the reference examples and Examples and the tables which are described later.

Ex: Example number, REx: reference example number, No: compound number, Dat: physicochemical data (F: FAB-MS $(M+H)^+$, FN: FAB-MS $(M-H)^-$, ES: ESI-MS $(M+H)^+$, ESN; ESI-MS $(M-H)^-$, AP: API-MS $(M+H)^+$, EI: EI-MS $(M)^+$, APCI: APCI-MS $(M+H)^+$, AN: APCI-MS $(M-H)^-$, NMR: δ (ppm) of characteristic peaks by $^1H$ NMR in DMSO-$d_6$, NMRC: δ (ppm) of characteristic peaks by $^1H$ NMR in $CDCl_3$), EA: elemental analysis (Calcd: calculated value, Found: measured value), Str: structural formula, RSn: reference example production method (the numeral indicates reference example number in which respective production method was used as reference), Syn: Example production method (the numeral indicates Example number in which respective production method was used as reference), Sal: salt (compound with no description indicates its free form), Fum: fumaric acid, Me: methyl, Et: ethyl, iPr: isopropyl, cPr: cyclopropyl, iBu: isobutyl, tBu: tert-butyl, cPen: cyclopentyl, cHex: cyclohexyl, cHep: cycloheptyl, Ph: phenyl, Boc: tert-butoxycarbonyl, Bn: benzyl, and TBS: tert-butyldimethylsilyl.

In the following reference examples, there is a case in which a treating operation after completion of a reaction until purification is described by abridging as "the reaction liquid was post-treated". Said treatment is a generally used method in organic synthetic chemistry and means a series of steps in which separation of layers is carried out after adding water to a reaction liquid, extraction is carried out with an appropriate solvent, the organic layers are combined and dried and then the solvent is evaporated and, as occasion demands, purification is carried out by a usual method such as silica gel column chromatography or the like.

Reference Example 1

Cyclopentylamine and potassium carbonate were added to a DMF solution of 4-chloro-2-fluorobenzonitrile, followed by stirring at 100° C. for 12 hours. By post-treating the reaction liquid, 4-chloro-2-(cyclopentylamino)benzonitrile was obtained.

Reference Example 2

Cyclopentylamine and potassium carbonate were added to a DMF solution of 4-bromo-2-fluorobenzonitrile, followed by stirring at 60° C. By post-treating the reaction liquid, 4-bromo-2-(cyclohexylamino)benzonitrile was obtained. By making reference to the method described in J. Am. Chem. Soc.; 1996; 118; 7215-7216, this was allowed to react with piperidine to obtain 2-(cyclohexylamino)-4-piperidin-1-yl-benzonitrile.

Reference Example 3

Sodium carbonate and 1,4-dibromobutane were added to an acetonitrile solution of 2-{[(1S*,2S*)-2-aminocyclohexyl]amino}-4-chlorobenzonitrile, followed by heating under reflux for 2 days. By post-treating the reaction liquid, 4-chloro-2-{[(1S*,2S*)-2-pyrrolidin-1-ylcyclohexyl]amino}benzonitrile was obtained.

Reference Example 4

4-Chloro-2-[(2,2,6,6-tetramethylpiperidin-4-yl)amino]benzonitrile was dissolved in N-methyl-2-pyrrolidinone, potassium carbonate and iodoethane were added, followed by stirring at 90° C. By post-treating the reaction liquid, 4-chloro-2-[(1-ethyl-2,2,6,6-tetramethylpiperidin-4-yl)amino]benzonitrile was obtained.

Reference Example 5

Cyclohexanone and sodium triacetoxyborohydride were added to a 1,2-dichloroethane-acetic acid solution of methyl 2-amino-5-chlorobenzoate, followed by stirring at room temperature. By post-treating the reaction liquid, methyl 5-chloro-2-(cyclohexylamino)benzoate was obtained.

Reference Example 6

Methyl 5-(bromomethyl)-2-nitrobenzoate was added to a DMF suspension of potassium carbonate and piperidine, followed by stirring at room temperature to obtain methyl 2-nitro-5-(piperidin-1-ylmethyl)benzoate (Dat, ES: 279). This compound was dissolved in acetic acid, iron powder was added thereto, followed by stirring at 60° C. to obtain methyl 2-amino-5-(piperidin-1-ylmethyl)benzoate (Dat, F: 249). Cyclohexanone and sodium triacetoxyborohydride were added to an acetic acid solution of this compound, followed by stirring at room temperature. By post-treating the reaction liquid, methyl 2-(cyclohexylamino)-5-(piperidin-1-ylmethyl)benzoate was obtained.

Reference Example 7

4-Chloro-2-(cyclopentylamino)benzonitrile and concentrated sulfuric acid were added to water, followed by stirring while heating under reflux. The reaction liquid was neutralized by adding sodium hydroxide to the reaction liquid, and the organic layer was extracted with chloroform to obtain 4-chloro-2-(cyclopentylamino)benzoic acid.

Reference Example 8

Ethylene glycol and sodium hydroxide were added to 4-chloro-2-{[(1S*,2S*)-2-pyrrolidin-1-ylcyclohexyl]amino}benzonitrile, followed by stirring at 190° C. for 5 hours. After neutralizing the reaction liquid by adding hydrochloric acid, the organic layer was extracted with chloroform and the solvent was evaporated to obtain 4-chloro-2-{[(1S*,2S*)-2-pyrrolidin-1-ylcyclohexyl]amino}benzoic acid.

Reference Example 9

Methyl 5-chloro-2-(cyclohexylamino)benzoate was dissolved in ethanol, a 1 M sodium hydroxide aqueous solution was added, followed by stirring at 70° C. By post-treating the reaction liquid, 5-chloro-2-(cyclohexylamino)benzoic acid was obtained.

Reference Examples 10 to 132

In the same manner as the methods of Reference Examples 1 to 9, compounds of Reference Examples 10 to 132 shown in Tables 1 to 7 which are described later were produced using respectively corresponding materials.

Structures and physicochemical data of the compounds of Reference Examples 10 to 132 are shown in the Tables 1 to 7.

Reference Example 133

N-Bromosuccinimide and AIBN were added to a carbon tetrachloride solution of 2-fluoro-4-methylbenzonitrile, followed by heating under reflux to obtain 4-(bromomethyl)-2-fluorobenzonitrile. By allowing this to react with morpholine in DMF in the presence of potassium carbonate, 2-fluoro-4-(morpholin-4-ylmethyl)benzonitrile was obtained. In DMF and in the presence of potassium carbonate, this was allowed to react with cyclohexanamine at 160° C. for 30 minutes while carrying out microwave irradiation. By post-treating the reaction liquid, 2-(cyclohexylamino)-4-(morpholin-4-ylmethyl)benzonitrile was obtained.

Reference Example 134

1-Chloro-2,5-pyrrolidinedione (NCS) was added at room temperature to a DMF solution of tert-butyl {(1R,2R)-2-[(5-chloro-2-cyanophenyl)amino]cyclohexyl}carbamate, followed by stirring at 80° C. for 5 hours. By post-treating the reaction liquid, tert-butyl {(1R,2R)-2-[(4,5-dichloro-2-cyanophenyl)amino]cyclohexyl}carbamate was obtained.

Reference Example 135

Potassium carbonate and 2,2,6,6-tetramethylpiperidine-4-amine were added to a DMF solution of 2-fluoro-4-(trifluoromethyl)benzonitrile. After stirring at 60° C. for 12 hours, methyl iodide and potassium carbonate were added thereto, followed by stirring at room temperature for 1 day. By post-treating the reaction liquid, 2-[(1,2,2,6,6-pentamethylpiperidin-4-yl)amino]-4-(trifluoromethyl)benzonitrile was obtained.

Reference Example 136

Di-tert-butyl dicarbonate was added to a THF solution of 2-{[(1S,2S)-2-aminocyclohexyl]amino}-4-chlorobenzonitrile and triethylamine, followed by stirring at room temperature for 12 hours. By pot-treating the reaction liquid, tert-butyl {(1S,2S)-2-[(5-chloro-2-cyanophenyl)amino]cyclohexyl}carbamate was obtained.

Reference Example 137

N-Bromosuccinimide (NBS) was added to a dichloromethane solution of {(1S,2S)-2-[(5-chloro-2-cyanophenyl)amino]cyclohexyl}carbamate, followed by stirring at room temperature for 7 hours. By post-treating the reaction liquid, tert-butyl {(1S,2S)-2-[(4-bromo-5-chloro-2-cyanophenyl)amino]cyclohexyl}carbamate was obtained.

Reference Example 138 tert-Butyl {(1S,2S)-2-[(4-bromo-5-chloro-2-cyanophenyl)amino]cyclohexyl}carbamate, trimethyl boroxine and potassium carbonate were suspended in a mixed solvent of 1,4-dioxane (16 ml) and water (4 ml), tetrakis(triphenylphosphine)palladium was added thereto, followed by stirring at 110° C. for 1 day. By post-treating the reaction liquid, tert-butyl {(1S,2S)-2-[(5-chloro-2-cyano-4-methylphenyl) amino]cyclohexyl}carbamate was obtained.

Reference Example 139

4 M Hydrogen chloride/ethyl acetate (20 ml) was added to an ethanol solution of {(1S,2S)-2-[(5-chloro-2-cyano-4-methylphenyl)amino]cyclohexyl}carbamate, followed by stirring at room temperature for 12 hours. By concentrating the reaction liquid under a reduced pressure, 2-{[(1S,2S)-2-aminocyclohexyl]amino}-4-chloro-5-methylbenzonitrile was obtained.

Reference Example 140

By the methods described in U.S. Pat. No. 4,801,604 and HETEROCYCLES, vol. 31, no. 10, 1990, 1837-1846, (1R,2S)-2-pyrrolidin-1-yl cyclohexanamine was produced. This and 4-chloro-2-fluorobenzonitrile and potassium carbonate were stirred at 100° C. for 1 hour in acetonitrile under microwave irradiation and then stirred at 120° C. for 100 minutes. By post-treating the reaction liquid, 4-chloro-2-{[(1R,2S)-2-pyrrolidin-1-ylcyclohexyl]amino}benzonitrile was obtained.

Reference Example 141 tert-Butoxy potassium was added to a mixture of 2-fluoro-4-(trifluoromethyl)benzonitrile, 3-pyridine amine and THF, followed by stirring at room temperature for 7 hours. After neutralizing the reaction liquid by adding 1 M hydrochloric acid thereto and subsequent extraction with chloroform, the solvent was evaporated under a reduced pressure. The residue was purified by column chromatography to obtain 2-(pyridine-3-ylamino)-4-(trifluoromethyl)benzonitrile.

Reference Example 142

1-(Dimethylamin-1-ylcarbonyl)cyclohexanamine hydrochloride was added to a THF suspension of lithium aluminum hydride (LAH) under ice-cooling, followed by heating under reflux for 3 hours. Sodium hydroxide aqueous solution and sodium sulfate were added to the reaction liquid and filtered. The filtrate was concentrated under a reduced pressure, 4-chloro-2-fluorobenzonitrile and potassium carbonate were added to the resulting residue, and this was stirred at 180° C. for 1 hour to effect the reaction while irradiating microwave. By post-treating the reaction liquid, 4-chloro-2-({1-[(dimethylamino)methyl]cyclohexyl}amino)benzonitrile.

Reference Example 143

Under ice-cooling, sodium borohydride was slowly added in small portions to an acetic acid solution of 2-{[(1R,2R)-2-aminocyclohexyl]amino}-4-(trifluoromethyl)benzonitrile, followed by stirring with heating at 60° C. for 6 hours. By post-treating the reaction liquid, 2-{[(1R,2R)-2-(diethylamino)cyclohexyl]amino}-4-(trifluoromethyl)benzonitrile was obtained.

Reference Example 144

Under ice-cooling, sodium borohydride was slowly added in small portions to an acetic acid solution of 2-{[(1R,2R)-2-aminocyclohexyl]amino}-4-(trifluoromethyl)benzonitrile, followed by heating at 60° C. for 6 hours. By post-treating the reaction liquid, 2-{[(1R,2R)-2-(ethylamino)cyclohexyl]amino}-4-(trifluoromethyl)benzonitrile was obtained. A formalin aqueous solution and sodium triacetoxyborohydride were added to a THF solution of this, followed by stirring. By post-treating the reaction liquid, 2-({(1R,2R)-2-[ethyl(methyl)amino]cyclohexyl}amino)-4-(trifluoromethyl)benzonitrile was obtained.

Reference Example 145

Methanol and thionyl chloride were added to 2-{[(1S,2S)-2-aminocyclohexyl]amino}-4-(trifluoromethyl)benzonitrile, followed by stirring with heating at 60° C. After neutralizing the reaction liquid by adding sodium bicarbonate aqueous solution thereto, the reaction liquid was post-treated to obtain methyl 2-{[(1S,2S)-2-aminocyclohexyl]amino}-4-(trifluoromethyl)benzoate.

Reference Example 146

In DMF and in the presence of sodium hydride, methyl 2-({(1S,2S)-2-[(tert-butoxycarbonyl)amino]cyclohexyl}amino)-4-(trifluoromethyl)benzoate was allowed to react with methyl iodide at 70° C. for 1 hour. By post-treating the reaction liquid, methyl 2-({(1S,2S)-2-[(tert-butoxycarbonyl)(methyl)amino]cyclohexyl}amino)-4-(trifluoromethyl)benzoate was obtained.

Reference Example 147

Under an atmosphere of hydrogen (1 atm) and in ethanol, catalytic hydrogenation of ethyl 4-nitro-2-{[(1S,2S)-2-pyrrolidin-1-ylcyclohexyl]amino}benzoate was carried out at room temperature in the presence of 10% palladium-carbon to obtain ethyl 4-amino-2-{[(1S,2S)-2-pyrrolidin-1-ylcyclohexyl]amino}benzoate.

Reference Example 148

Ethyl 4-amino-2-{[(1S,2S)-2-pyrrolidin-1-ylcyclohexyl]amino}benzoate was allowed to react with sodium nitrite ($NaNO_2$) and trifluoroborane-hydrogen fluoride complex ($BF_3$.HF) in water at 10° C. for 10 minutes. By post-treating the reaction liquid, ethyl 4-fluoro-2-{[(1S,2S)-2-pyrrolidin-1-ylcyclohexyl]amino}benzoate was obtained.

Reference Example 149

Under ice-cooling, formaldehyde aqueous solution (36%) and sodium triacetoxyborohydride were added to a THF solution of 2-{[(1R,2R)-2-aminocyclohexyl]amino}-4-(trifluoromethyl)benzonitrile, followed by stirring at room temperature for 30 minutes. By post-treating the reaction liquid, 2-{[(1R,2R)-2-(dimethylamino)cyclohexyl]amino}-4-(trifluoromethyl)benzonitrile was obtained. Ethylene glycol and sodium hydroxide were added to this. This was stirred at 170° C. for 6 hours and then spontaneously cooled. This was neutralized with 1 M hydrochloric acid and then stirred while spontaneously cooling it. By collecting the thus precipitated solid by filtration, 2-{[(1R,2R)-2-(dimethylamino)cyclohexyl]amino}-4-(trifluoromethyl)benzoic acid.

Reference Example 150

Potassium hydroxide aqueous solution was added to an ethanol-water mixed solution of 2-{[(1S,2S)-2-(benzyloxy)cyclohexyl]amino}-4-(trifluoromethyl)benzonitrile. This was stirred at 100° C. for 5 hours and then spontaneously cooled. After neutralizing with 1 M hydrochloric acid, the organic layer was extracted with chloroform. By concentrating the organic layer under a reduced pressure, 2-{[(1S,2S)-2-(benzyloxy)cyclohexyl]amino}-4-(trifluoromethyl)benzoic acid was obtained.

Reference Example 151

1-Chloro-2,5-pyrrolidinedione was added at room temperature to a 1,2-dichloroethane and DMF solution of 2-[(cyclopropylmethyl)amino]nicotinic acid, followed by stirring for 1 day. By post-treating the reaction liquid, 5-chloro-2-[(cyclopropylmethyl)amino]nicotinic acid was obtained.

Reference Example 152

A mixture of 2-fluoronicotinic acid and 2,2,2-trifluoroethenamine was stirred at 180° C. for 30 minutes with microwave irradiation and then spontaneously cooled. Water and 6 ml of 1 N sodium hydroxide aqueous solution and chloroform were added to the mixture, and the water layer was extracted with chloroform. By concentrating the organic layer under a reduced pressure, 2-[(2,2,2-trifluoroethyl)amino]nicotinic acid was obtained.

Reference Example 153

Diisopropylethylamine and (1S,2S)-1,2-cyclohexandiamine were added to 2-chloro-6-(trifluoromethyl)nicotinic acid, followed by stirring at 100° C. for 30 minutes and at 140° C. for 10 minutes using a microwave reaction device. The reaction liquid was dissolved in acetonitrile, potassium carbonate and 1,4-dibromobutane were added, followed by stirring at 50° C. for 8 hours. By dissolving the residue extracted with chloroform in methanol and THF, adding 1 M sodium hydroxide aqueous solution thereto and carrying out the reaction at 50° C., 2-{[(1S,2S)-2-pyrrolidin-1-ylcyclohexyl]amino}-6-(trifluoromethyl)nicotinic acid was obtained.

Reference Example 154

A mixture of exo-2-aminonorbornane and 2-chloronicotinic acid was stirred at 160° C. for 1 day and then spontaneously cooled. The reaction liquid was diluted with 1 M sodium hydroxide aqueous solution and then washed with diethyl ether. The water layer was neutralized with 1 M hydrochloric acid and then the precipitated crystals were collected by filtration to obtain rel-2-[(1R,2R,4S)-bicyclo[2.2.1]hept-2-ylamino]nicotinic acid.

Reference Example 155

By allowing ethyl 2,6-dichloronicotinate and cyclohexanamine to undergo the reaction at 50° C. for 1 hour in DMF in the presence of potassium carbonate, ethyl 6-chloro-2-(cyclohexylamino)nicotinate was obtained. By carrying out hydrolysis of an ethanol solution of this at 70° C. for 18 hours in the presence of 1 M sodium hydroxide, 6-chloro-2-(cyclohexylamino)nicotinic acid was obtained.

Reference Example 156

In methylene chloride, ethyl 2,6-difluoronicotinate and cyclohexanamine were stirred at 0° C. for 0.5 hour to obtain ethyl 2-(cyclohexylamino)-6-fluoronicotinate (ES: 267). This was stirred in ethanol by adding sodium hydroxide. By concentrating the reaction liquid under a reduced pressure and purifying the resulting residue by silica gel column chromatography, 2-(cyclohexylamino)-6-fluoronicotinic acid was obtained.

Reference Example 157

By treating ethyl 2-(cyclohexylamino)-6-fluoronicotinate with sodium methoxide at room temperature in methanol, methyl 2-(cyclohexylamino)-6-methoxy nicotinate was obtained (F: 265). Ethanol and 1 M sodium hydroxide were added to this, followed by stirring at 75° C. The reaction liquid was neutralized with 1 M hydrochloric acid and concentrated under a reduced pressure to obtain 2-(cyclohexylamino)-6-methoxynicotinic acid.

Reference Example 158

2-Fluoro-4-(trifluoromethyl)benzoyl chloride was added to a pyridine solution of 7-amino-1-methyl-3,4-dihydroquinolin-2(1H)-one, followed by stirring at room temperature for 12 hours. Water was added to the reaction liquid, followed by stirring for 30 minutes and then the precipitated crystals were collected by filtration to obtain 2-fluoro-N-(1-methyl-2-oxo-1,2,3,4-tetrahydroquinolin-7-yl)-4-(trifluoromethyl)benzamide.

Reference Example 159

In DMF, 6-amino-4-(trifluoromethyl)-1,3-dihydro-2H-indol-2-one and ethyl 1,3-dioxo-1,3-dihydro-2H-isoindol-2-carboxylate were allowed to undergo the reaction at 60° C. for 18 hours in the presence of triethylamine. Water was added to the reaction liquid and the resulting precipitate was collected by filtration to obtain 2-[2-oxo-4-(trifluoromethyl)-2,3-dihydro-1H-indol-6-yl]-1H-isoindol-1,3-(2H)-dione.

Reference Example 160

In DMF, 2-[2-oxo-4-(trifluoromethyl)-2,3-dihydro-1H-indol-6-yl]-1H-isoindol-1,3-(2H)-dione was allowed to react with methyl iodide at room temperature for 3 hours in the presence of sodium hydride. By post-treating the reaction liquid, 2-[3,3-dimethyl-2-oxo-4-(trifluoromethyl)-2,3-dihydro-1H-indol-6-yl]-1H-isoindol-1,3-(2H)-dione was obtained.

Reference Example 161

By adding a hydrazine aqueous solution to a methanol-chloroform solution of 2-[3,3-dimethyl-2-oxo-4-(trifluoromethyl)-2,3-dihydro-1H-indol-6-yl]-1H-isoindol-1,3-(2H)-dione and carrying out the reaction at room temperature for 10 hours, 6-amino-3,3-dimethyl-4-(trifluoromethyl)-1,3-dihydro-2H-indol-2-one was obtained.

Reference Example 162

HATU was added to a dichloroethane solution of 2-(cyclohexylamino)-6-fluoronicotinic acid and triethylamine. After 30 minutes of stirring at room temperature, 7-amino-1-methyl-3,4-dihydroquinolin-2(1H)-one was added thereto. The reaction liquid was stirred overnight at room temperature and then hearted under reflux for 3 hours. By post-treating the reaction liquid, 2-(cyclohexylamino)-6-fluoro-N-(1-methyl-2-oxo-1,2,3,4-tetrahydroquinolin-7-yl)nicotinamide was obtained.

Reference Example 163

Sulfuric acid was added to an ethanol solution of 2,6-dichloronicotinic acid and heated under reflux for 24 hours. After adding saturated sodium bicarbonate aqueous solution thereto, ethanol was evaporated under a reduced pressure. The residue was extracted with ethyl acetate and the organic layer was concentrated under a reduced pressure. Potassium carbonate was added to a DMF solution of the obtained ethyl 2,6-dichloronicotinate, and cyclopentylamine was added thereto, followed by stirring at 0° C. for 1 hour and at room temperature for 6 hours. By post-treating the reaction liquid, ethyl 6-chloro-2-[(cyclopropylmethyl)amino]nicotinate was obtained.

Reference Example 164

Sodium hydride was added at room temperature to a DMF solution of ethyl 6-chloro-2-[(cyclopropylmethyl)amino] nicotinate and 2,2,2-trifluoroethanol, followed by stirring at 80° C. for 20 hours. By post-treating the reaction liquid, ethyl 2-[(cyclopropylmethyl)amino]-6-(2,2,2-trifluoroethoxy) nicotinate was obtained.

Reference Example 165

1-[(tert-Butoxycarbonyl)amino]cyclohexancarboxylate, pyrrolidine, 1-ethyl-3-[3-(N,N-dimethylamino)propyl]carbodiimide hydrochloride and 1-hydroxybenzotriazole were allowed to undergo the reaction at room temperature in methylene chloride. By post-treating the reaction liquid, tert-butyl [1-(pyrrolidin-1-ylcarbonyl)cyclohexyl]carbamate was obtained.

Reference Example 166

1-(Pyrrolidin-1-ylcarbonyl)cyclohexanamine hydrochloride was added under ice-cooling to a THF solution of LAH, followed by heating under reflux for 3 hours. Sodium hydroxide aqueous solution and sodium sulfate were added to the reaction liquid, followed by filtering. By concentrating the filtrate under a reduced pressure, 1-(pyrrolidin-1-ylmethyl) cyclohexanamine was obtained.

Reference Example 167

In dichloromethane, a mixture of 4-chloro-2-[(2-hydroxyethyl)amino]benzoic acid and 7-amino-1-methyl-3,4-dihydroquinolin-2(1H)-one was treated with 1-ethyl-3-[3-(N,N-dimethylamino)propyl]carbodiimide hydrochloride at room temperature to obtain 4-chloro-2-[(2-hydroxyethyl)amino]-N-(1-methyl-2-oxo-1,2,3,4-tetrahydroquinolin-7-yl)benzamide.

Reference Example 168

4-Chloro-2-[(2-hydroxyethyl)amino]-N-(1-methyl-2-oxo-1,2,3,4-tetrahydroquinolin-7-yl)benzamide was dissolved in tetrahydrofuran, diisopropylethylamine and methanesulfonyl chloride were added, followed by stirring at room temperature for 3 hours. By post-treating the reaction liquid, 2-({5-chloro-2-[(1-methyl-2-oxo-1,2,3,4-tetrahydroquinolin-7-yl)carbamoyl]phenyl}amino)ethyl methanesulfonate was obtained.

Reference Example 169

Palladium-carbon and ammonium formate were added to a methanol solution of 2-[(1-benzylpiperidin-4-yl)amino]-N-(1-methyl-2-oxo-1,2,3,4-tetrahydroquinolin-7-yl)-4-(trifluoromethyl)benzamide, followed by heating under reflux for 2 hours. After spontaneous cooling, Celite filtration was carried out and then the filtrate was concentrated under a reduced pressure. By purifying the residue by silica gel column chromatography, N-(1-methyl-2-oxo-1,2,3,4-tetrahydroquinolin-7-yl)-2-(piperidin-4-ylamino)-4-(trifluoromethyl)benzamide was obtained.

Reference Example 170

Under ice-cooling, 1-chloroethyl chloroformate was added to a 1,2-dichloroethane solution of 2-[(1-benzylpiperidin-4-yl)amino]-4-chloro-N-(1-methyl-2-oxo-1,2,3,4-tetrahydroquinolin-7-yl)benzamide. This was stirred for 1 hour under heat reflux and then concentrated under a reduced pressure. After dissolving in methanol, this was stirred for 2 hours under heat reflux. After concentration of the reaction liquid under a reduced pressure, the residue was purified by silica gel column chromatography to obtain 4-chloro-N-(1-methyl-2-oxo-1,2,3,4-tetrahydroquinolin-7-yl)-2-(piperidin-4-ylamino)benzamide.

Reference Example 171

2-Chloro-6-(trifluoromethyl)nicotinic acid, (1S,2S)-1,2-cyclohexandiamine and diisopropylethylamine were mixed, followed by stirring at 150° C. for 30 minutes under microwave irradiation. After spontaneous cooling, the reaction liquid was concentrated under a reduced pressure, the residue was dissolved in methanol and sulfuric acid was added thereto. After 6 days of stirring under heat reflux, this was spontaneously cooled and concentrated under a reduced pressure. This was neutralized with saturated sodium bicarbonate aqueous solution and then extracted with chloroform. After concentration of the organic layer under a reduced pressure, the resulting residue was dissolved in THF, and sodium triacetoxyborohydride and a formaldehyde aqueous solution (36%) were added thereto in that order. By post-treating the reaction liquid, methyl 2-{[(1S,2S)-2-(dimethylamino)cyclohexyl]amino}-6-(trifluoromethyl)nicotinate was obtained.

Reference Example 172

An ethanol solution of 1-(2-{[tert-butyl(dimethyl)silyl] oxy}ethyl)-7-nitro-3,4-dihydroquinoline-2(1H)-one and 10% palladium-carbon was stirred at room temperature for 3 hours under an atmosphere of hydrogen (1 atm), the reaction liquid was filtered, and then the filtrate was concentrated under a reduced pressure. By purifying the residue by silica gel column chromatography, 7-amino-1-(2-{[tert-butyl(dimethyl)silyl]oxy}ethyl)-3,4-dihydroquinolin-2(1H)-one was obtained.

Reference Example 173

7-Nitro-3,4-dihydroquinolin-2(1H)-one, (2-bromoethoxy)(tert-butyl)dimethylsilane, potassium carbonate, potassium iodide and water were added to DMF, followed by stirring at room temperature for 2 days and then stirred at 40° C. for 3 days. By post-treating the reaction liquid, 1-(2-{[tert-butyl(dimethyl)silyl]oxy}ethyl)-7-nitro-3,4-dihydroquinolin-2(1H)-one was obtained.

Reference Example 174

A methylene chloride solution of 7-amino-1-(2-{[tert-butyl(dimethyl)silyl]oxy}ethyl)-3,4-dihydroquinolin-2(1H)- one, 2-(cyclohexylamino)-4-(trifluoromethyl)benzoic acid, 1-ethyl-3-[3-(N,N-dimethylamino)propyl]carbodiimide hydrochloride, dimethylaminopyridine and triethylamine was allowed to undergo the reaction at room temperature. By post-treating the reaction liquid, N-[1-(2-{[tert-butyl(dimethyl)silyl]oxy}ethyl)-2-oxo-1,2,3,4-tetrahydroquinolin-7-yl]-2-(cyclohexylamino)-4-(trifluoromethyl)benzamide was obtained.

Reference Example 175

Aluminum chloride and tert-butyl chloride were added under ice-cooling to 2-fluorophenol and stirred at room temperature. By adding water to the reaction liquid, concentrating the organic layer under a reduced pressure and crystallizing from hexane, 4-tert-butyl-2-fluorophenol was obtained.

Reference Example 176

A chloroform solution of 4-tert-butyl-2-fluorophenol, 2-dimethylaminopyridine and 2,6-lutidine, cooled to −78° C., was treated with trifluoromethanesulfonic acid anhydride to obtain 4-tert-butyl-2-fluorophenyl trifluoromethanesulfonate. Under an atmosphere of carbon monoxide, a DMSO solution of the resulting sulfonate, methanol, triethylamine, palladium acetate and diphenylphosphinopropane was allowed to undergo the reaction at 60° C. By post-treating the reaction liquid, methyl 4-tert-butyl-2-fluorobenzoate was obtained.

Reference Example 177

Oxalyl chloride was added to a THF solution of 4-tert-butyl-2-fluorobenzoic acid and stirred for 1 hour, and aqueous ammonia was added to this. By post-treating the reaction liquid, 4-tert-butyl-2-fluorobenzamide was obtained.

Reference Example 178

Pyridine and trifluoroacetic anhydride were added to a dioxane solution of 4-tert-butyl-2-fluorobenzamide and stirred at room temperature for 3 hours. By post-treating the reaction liquid, 4-tert-butyl-2-fluorobenzonitrile was obtained.

Reference Example 179

Under an atmosphere of hydrogen and in ethanol, catalytic hydrogenation reaction of 2-(cyclohexylamino)-3-(trifluoromethyl)benzonitrile was carried out in the presence of Raney nickel to obtain 2-(aminomethyl)-N-cyclohexyl-6-(trifluoromethyl)aniline.

Reference Examples 180 to 358

In the same manner as the methods of Reference Examples 1 to 9 and Reference Examples 133 to 179, the compounds of Reference Examples 180 to 358 shown in Tables 8 to 18 which are described later were produced using respectively corresponding materials.

Reference Example 359

Sodium hydride was added under ice-cooling to a DMF solution of malonic acid dimethyl ester, and then 1,2-dichloro-3,5-dinitrobenzene was added thereto and allowed to undergo the reaction at room temperature overnight. By post-treating the reaction liquid, dimethyl (2-chloro-4,6-dinitrophenyl)malonate (Dat, FN: 332) was obtained. This was dissolved in DMSO, lithium chloride and water were added, followed by stirring at 100° C. for 2 hours. By post-treating the reaction liquid, methyl (2-chloro-4,6-dinitrophenyl)acetate was obtained.

Reference Example 360

A mixture of methyl (2-chloro-4,6-dinitrophenyl)acetate, ammonium chloride, iron powder, ethanol and water was stirred at 120° C. for 3 hours. The reaction liquid was filtered, trifluoroacetic acid was added to the filtrate, followed by stirring overnight at room temperature. The reaction liquid was concentrated under a reduced pressure, 1 M sodium hydroxide was added to the residue, and this was post-treated to obtain 6-amino-4-chloro-1,3-dihydro-2H-indol-2-one.

In this connection, the amine compounds used as the materials in the amidation reaction described in the aforementioned Reference Examples 158 and 167 can be produced by the method described in WO 2004/110986.

Structures and physicochemical data of the compounds of Reference Examples 133 to 360 are shown in Tables 8 to 18.

Example 1

Hydrochloride of 1-ethyl-3-[3-(N,N-dimethylamino)propyl]carbodiimide (250 mg) was added to a chloroform (15 mL) solution of 4-chloro-2-(cyclopentylamino)benzoic acid (250 mg) and 7-amino-1-methyl-3,4-dihydroquinolin-2(1H)-one (184 mg), followed by stirring at room temperature for 26 hours. The reaction liquid was concentrated under a reduced pressure. By purifying the residue by silica gel column chromatography (chloroform:methanol, 1:0 to 9:1), 4-chloro-2-(cyclopentylamino)-N-(1-methyl-2-oxo-1,2,3,4-tetrahydroquinolin-7-yl)benzamide was obtained. By treating this with 4 M hydrogen chloride/ethyl acetate solution, 4-chloro-2-(cyclopentylamino)-N-(1-methyl-2-oxo-1,2,3,4-tetrahydroquinolin-7-yl)benzamide hydrochloride (97 mg) was obtained as a solid.

Example 2

Hydrochloride of 1-ethyl-3-[3-(N,N-dimethylamino)propyl]carbodiimide (174 mg) and dimethylaminopyridine (21 mg) were added to a methylene chloride (5 mL) solution of 4-chloro-2-{[(1S*,2S*)-2-pyrrolidin-1-ylcyclohexyl]amino}benzoic acid (220 mg) and 7-amino-1-methyl-3,4-dihydroquinolin-2(1H)-one (100 mg). After stirring the reaction liquid overnight at room temperature, the reaction liquid was concentrated under a reduced pressure. By purifying the residue by silica gel column chromatography (hexane:ethyl acetate, 1:0 to 1:1), 4-chloro-N-(1-methyl-2-oxo-1,2,3,4-tetrahydroquinolin-7-yl)-2-{[(1S*,2S*)-2-pyrrolidin-1-ylcyclohexyl]amino}benzamide was obtained as a pale yellow amorphous. By treating this with 4 M hydrogen chloride/ethyl acetate solution, 4-chloro-N-(1-methyl-2-oxo-1,2,3,4-tetrahydroquinolin-7-yl)-2-{[(1S*,2S*)-2-pyrrolidin-1-ylcyclohexyl]amino}benzamide hydrochloride (212 mg) was obtained as an amorphous.

Example 3 m-Chloroperbenzoic acid (mCPBA; 235 mg) was added under ice-cooling to a methylene chloride solution of 4-chloro-N-(1-methyl-2-oxo-1,2,3,4-tetrahydroquinolin-7-yl)-2-{[(methyl sulfanil)ethyl]amino}benzamide (250 mg), followed by stirring at room temperature for 2 hours. A saturated sodium bicarbonate aqueous solution was added to the reaction liquid, followed by extraction with chloroform. The organic layer was dried with sodium sulfate, and then the solution was concentrated under a reduced pressure. By purifying the resulting residue by silica gel column chromatography (hexane:ethyl acetate, 1:0 to 1:1), 4-chloro-N-(1-methyl-2-oxo-1,2,3,4-tetrahydroquinolin-7-yl)-2-{[(methyl sulfonyl)ethyl]amino}benzamide (150 mg) was obtained as a solid.

Example 4

4 M hydrogen chloride/ethyl acetate solution (5 mL) was added to an ethanol (5 mL) solution of tert-butyl 2-{[(5-chloro-2-{[(1-methyl-2-oxo-1,2,3,4-tetrahydroquinolin-7-yl)amino]carbonyl}phenyl)amino]methyl}piperidin-1-carboxylate (540 mg), followed by stirring at room temperature for 2 hours. By collecting the resulting precipitate by filtration, 4-chloro-N-(1-methyl-2-oxo-1,2,3,4-tetrahydroquinolin-7-yl)-2-[(piperidin-2-ylmethyl)amino]benzamide hydrochloride (470 mg) was obtained as a solid.

Example 5

4-Chloro-N-(1-methyl-2-oxo-1,2,3,4-tetrahydroquinolin-7-yl)-2-[(piperidin-2-ylmethyl)amino]benzamide hydrochloride (100 mg) was dissolved in a mixed solution of acetic acid (3 mL) and methanol (2 mL), and 1 ml of formaldehyde aqueous solution (36%) was added thereto. Sodium triacetoxyborohydride (252 mg) was added to this solution at 0° C., followed by stirring at room temperature for 30 minutes. After concentration under a reduced pressure, this was made basic by adding a saturated sodium bicarbonate aqueous solution, followed by extraction with chloroform. After drying the organic layer with magnesium sulfate, the solvent was evaporated under a reduced pressure. By purifying the residue by silica gel column chromatography (chloroform:methanol, 10:1) and treating the resulting free base with 4 M hydrogen chloride/ethyl acetate solution, 4-chloro-N-(1-methyl-2-oxo-1,2,3,4-tetrahydroquinolin-7-yl)-2-{[(1-methylpiperidin-2-yl)methyl]amino}benzamide hydrochloride (45 mg) was obtained as a solid.

Examples 6 to 94

In the same manner as the methods of Examples 1 to 5, the compounds of Examples 6 to 94 shown in Tables 19 to 25 which are described later were produced using respectively corresponding materials.

Structures and physicochemical data of the compounds of Examples 1 to 94 are shown in Tables 19 to 25.

Example 95

3-Fluoropyridine hydrochloride (240 mg) and sodium carbonate (250 mg) were added to a dimethylformamide solution of 2-({5-chloro-2-[(1-methyl-2-oxo-1,2,3,4-tetrahydroquinolin-7-yl)carbamoyl]phenyl}amino)ethyl methanesulfonate (595 mg), followed by stirring at 40° C. for 15 hours. Water was added to the reaction liquid, followed by extraction with chloroform. The organic layer was dried with magnesium sulfate and then the solution was concentrated under a reduced pressure. The resulting residue was purified by silica gel column chromatography (basic silica gel, chloroform:methanol, 1:0 to 95:5). By treating the resulting free base with 4 M hydrogen chloride/ethyl acetate solution, 4-chloro-2-{[2-(3-fluoropyrrolidin-1-yl)ethyl]amino}-N-(1-methyl-2-oxo-1,2,3,4-tetrahydroquinolin-7-yl)benzamide hydrochloride (156 mg) was obtained as a solid.

Example 96

At room temperature, 1 M hydrochloric acid (0.38 mL) was added to an ethanol (20 mL) solution of 2-{[(1S,2S)-2-(benzyloxy)cyclohexyl]amino}-N-(1-methyl-2-oxo-1,2,3,4-tetrahydroquinolin-7-yl)-4-(trifluoromethyl)benzamide (140 mg), 10% palladium-carbon (240 mg) was added, followed by stirring for 1 day under an atmosphere of hydrogen. After neutralizing with a saturated sodium bicarbonate aqueous solution extracting with chloroform, the organic layer was concentrated under a reduced pressure. By purifying the residue by silica gel column chromatography (hexane:ethyl acetate, 1:0 to 1:1), 2-{[(1S,2S)-2-hydroxycyclohexyl]amino}-N-(1-methyl-2-oxo-1,2,3,4-tetrahydroquinolin-7-yl)-4-(trifluoromethyl)benzamide (66 mg) was obtained as an amorphous.

Example 97

2-Fluoro-N-(1-methyl-2-oxo-1,2,3,4-tetrahydroquinolin-7-yl)-4-(trifluoromethyl)benzamide (250 mg), N-methylpiperidone (0.5 mL) and (2S)-2-aminopropan-1-ol (800 mg) were mixed, followed by stirring at 180° C. for 40 minutes under microwave irradiation. After spontaneous cooling and subsequent purification by silica gel column chromatography (chloroform:methanol, 99:1 to 95:5), 2-{[(1S)-2-hydroxy-1-methylethyl]amino}-N-(1-methyl-2-oxo-1,2,3,4-tetrahydroquinolin-7-yl)-4-(trifluoromethyl)benzamide (188 mg) was obtained as a solid.

Example 98

HATU (220 mg) and triethylamine (0.08 mL) were added to a dichloroethane (10 mL) solution of 4-tert-butyl-2-{[(1S,2S)-2-pyrrolidin-1-ylcyclohexyl]amino}benzoic acid (200 mg) and 7-amino-1-methyl-3,4-dihydroquinolin-2(1H)-one (102 mg), followed by stirring at room temperature for 12 hours. A 1 M sodium hydroxide aqueous solution was added to the reaction liquid, followed by extraction with chloroform. After drying of the organic layer, the solution was concentrated under a reduced pressure and the resulting residue was purified by silica gel column chromatography (chloroform:methanol, 95:5). By adding fumaric acid (22 mg) to an ethyl acetate solution of the resulting free base, 4-tert-butyl-N-(1-methyl-2-oxo-1,2,3,4-tetrahydroquinolin-7-yl)-2-{[(1S,2S)-2-pyrrolidin-1-ylcyclohexyl]amino}benzamide fumarate (190 mg) was obtained as a solid.

Example 99

HATU (406 mg) was added to a DMF solution of 4-chloro-2-{[(1R,2R)-2-piperidin-1-ylcyclohexyl]amino}benzoic acid (300 mg) and 7-amino-1-methyl-3,4-dihydroquinolin-2(1H)-one (173 mg), followed by stirring at room temperature for 24 hours. After adding water to the reaction liquid and extracting with ethyl acetate, the organic layer was dried with sodium sulfate, and then the solution was concentrated under a reduced pressure and the resulting residue was purified by silica gel column chromatography (hexane:ethyl acetate, 2:1). By treating the resulting free base with 4 M hydrogen chloride/ethyl acetate, 4-chloro-N-(1-methyl-2-oxo-1,2,3,4- tetrahydroquinolin-7-yl)-2-{[(1R,2R)-2-piperidin-1-ylcyclohexyl]amino}benzamide hydrochloride (270 mg) was obtained as an amorphous.

Example 100

After dissolving N-(1-methyl-2-oxo-1,2,3,4-tetrahydroquinolin-7-yl)-2-(piperidin-4-ylamino)-4-(trifluoromethyl) benzamide (200 mg), cyclopropanecarbaldehyde (0.10 mL) and acetic acid (0.026 ml) in 1,2-dichloroethane (4 ml), sodium triacetoxyborohydride (285 mg) was added thereto. After stirring at room temperature for 2 hours, 1 M sodium hydroxide aqueous solution was added thereto, followed by extraction with chloroform. After drying the organic layer with sodium sulfate, the solution was concentrated under a reduced pressure and the resulting residue was purified by silica gel column chromatography (chloroform:methanol: aqueous ammonia, 1:0:0 to 90:9:1). By treating the resulting free base with 4 M hydrogen chloride/ethyl acetate, 2-{[1-(cyclopropylmethyl)piperidin-4-yl]amino}-N-(1-methyl-2-oxo-1,2,3,4-tetrahydroquinolin-7-yl)-4-(trifluoromethyl) benzamide hydrochloride (199 mg) was obtained as an amorphous.

Example 101

Triethylamine (0.16 mL) and ethyl iodide (0.068 mL) were added to a DMF solution of N-(1-methyl-2-oxo-1,2,3,4-tetrahydroquinolin-7-yl)-2-(piperidin-1-ylamino)-4-(trifluoromethyl)benzamide (250 mg). After 12 hours of stirring at room temperature and subsequent concentration under a reduced pressure, the resulting residue was purified by silica gel column chromatography (chloroform:methanol:aqueous ammonia, 1:0:0 to 90:9:1). By treating the resulting free base with 4 M hydrogen chloride/ethyl acetate, 2-[(1-ethylpiperidin-4-yl)amino]-N-(1-methyl-2-oxo-1,2,3,4-tetrahydroquinolin-7-yl)-4-(trifluoromethyl)benzamide hydrochloride (266 mg) was obtained as an amorphous.

Example 102

4-Cyano-2-(cyclohexylamino)-N-(1-methyl-2-oxo-1,2,3,4-tetrahydroquinolin-7-yl)benzamide (500 mg), di-tert-butyl dicarbonate ($Boc_2O$, 406 mg) and 10% palladium-carbon (200 mg) were added to a mixed solution of tert-butanol (40 mL) and DMF (20 mL) and stirred at room temperature for 15 hours under an atmosphere of hydrogen (1 atm). The reaction liquid was filtered and the filtrate was concentrated under a reduced pressure. By purifying the residue by silica gel column chromatography (hexane:ethyl acetate, 8:1 to 4:6), tert-butyl {3-(cyclohexylamino)-4-[(1-methyl-2-oxo-1,2,3,4-tetrahydroquinolin-7-yl)carbamoyl]benzyl}carbamate (453 mg) was obtained as a solid.

Example 103

10% Palladium-carbon (50 mg) was added to an ethanol (20 mL) solution of 4-chloro-N-(1-methyl-2-oxo-1,2,3,4-tetrahydroquinolin-7-yl)-2-{[1-(pyrrolidin-1-ylmethyl)cyclohexyl]amino}benzamide (500 mg), followed by stirring at room temperature for 21 days under an atmosphere of hydrogen. The reaction liquid was filtered and the filtrate was concentrated under a reduced pressure. The residue was purified by silica gel column chromatography (basic silica gel, hexane:ethyl acetate, 7:3 to 1:1). By treating the resulting free base with hydrobromic acid aqueous solution, N-(1-methyl-2-oxo-1,2,3,4-tetrahydroquinolin-7-yl)-2-{[1-(pyrrolidin-1-ylmethyl)cyclohexyl]amino}benzamide dihydrobromide (452 mg) was obtained as a solid.

Example 104

4 M Hydrogen chloride/ethyl acetate solution (3 mL) was added to tert-butyl methyl[(1S,2S)-2-({2-[(1-methyl-2-oxo-1,2,3,4-tetrahydroquinolin-7-yl)carbamoyl]-5-(trifluoromethyl)phenyl}amino)cyclohexyl]carbamate (1.17 g), followed by stirring at room temperature for 24 hours to obtain 2-{[(1S,2S)-2-(methylamino)cyclohexyl]amino}-N-(1-methyl-2-oxo-1,2,3,4-tetrahydroquinolin-7-yl)-4-(trifluoromethyl)phenyl}benzamide hydrochloride (1.04 g) as an amorphous.

Example 105

1 M Hydrochloric acid (0.37 mL) was added to an ethanol solution (1.5 mL) of N-[1-(2-{[tert-butyl(dimethyl)silyl] oxy}ethyl)-2-oxo-1,2,3,4-tetrahydroquinolin-7-yl]-2-(cyclohexylamino)-4-(trifluoromethyl)benzamide (220 mg), followed by stirring at room temperature for 5 hours. The reaction liquid was concentrated under a reduced pressure, and a sodium bicarbonate aqueous solution was added to the residue, followed by extraction with ethyl acetate. After drying the organic layer with sodium sulfate, the solution was concentrated under a reduced pressure. By purifying the residue by silica gel column chromatography (hexane:ethyl acetate, 2:1 to 2:3), 2-(cyclohexylamino)-N-[1-(2-hydroxyethyl)-2-oxo-1,2,3,4-tetrahydroquinolin-7-yl]-4-(trifluoromethyl)benzamide (148 mg) was obtained as a solid.

Example 106

HATU (176 mg) was added to a dichloroethane (5 mL) solution of 4-chloro-2-{[(1R,2S)-2-pyrrolidin-1-ylcyclohexyl]amino}benzoic acid (150 mg) and triethylamine (94 mg). After 30 minutes of stirring at room temperature, (2R)-6-amino-2-methyl-2H-1,4-benzoxazin-3(4H)-one (91 mg) was added thereto. After overnight stirring at room temperature, this was stirred for 3 hours under heating reflux. The reaction liquid was concentrated under a reduced pressure, a 1 M sodium hydroxide aqueous solution was added, followed by extraction with chloroform. The organic layer was concentrated under a reduced pressure and the residue was purified by silica gel column chromatography (chloroform: methanol, 1:0 to 85:15). By treating the resulting free base with 4 M hydrogen chloride/ethyl acetate, 4-chloro-N-[(2R)-2-methyl-3-oxo-3,4-dihydro-2H-benzoxazin-6-yl]-2-{[(1R, 2S)-2-pyrrolidin-1-ylcyclohexyl]amino}benzamide hydrochloride (100 mg) was obtained as an amorphous.

Example 107

HATU (343 mg) was added to a DMF (5 mL) solution of 2-{[(1S,2S)-2-pyrrolidin-1-ylcyclohexyl]amino}-4-(trifluoromethyl)benzoic acid (322 mg). After stirring at room temperature for 30 minutes, 6-amino-4-(trifluoromethyl)-1,3-dihydro-2H-indol-2-one (150 mg) was added thereto. After further stirring at 60° C. for 12 hours, the reaction liquid was concentrated under a reduced pressure, and the residue was purified by silica gel column chromatography (chloroform: methanol:aqueous ammonia, 1:0:0 to 90:9:1) and then again purified by silica gel column chromatography (basic silica gel, hexane:ethyl acetate, 1:0 to 7:3). By treating the resulting free base with 4 M hydrogen chloride/ethyl acetate solution, N-[2-oxo-4-(trifluoromethyl)-2,3-dihydro-1H-indol-6-yl]-

2-{[(1S,2S)-2-pyrrolidin-1-ylcyclohexyl]amino}-4-(trifluoromethyl)benzamide hydrochloride (179 mg) was obtained as an amorphous.

Example 108

Formaldehyde aqueous solution (36%, 0.12 mL) and sodium triacetoxyborohydride (236 mg) were added to a THF solution (4 ml) of 2-{[(1S,2S)-2-aminocyclohexyl]amino}-N-(2-methyl-1,3-benzothiazol-5-yl)-4-(trifluoromethyl) benzamide (200 mg). After stirring at room temperature for 30 minutes, the reaction liquid was concentrated under a reduced pressure. The residue was purified by silica gel column chromatography (chloroform:methanol:aqueous ammonia, 1:0:0 to 90:9:1). By treating the resulting free base with 4 M hydrogen chloride/ethyl acetate solution, 2-{[(1S,2S)-2-(dimethylamino)cyclohexyl]amino}-N-(2-methyl-1,3-benzothiazol-5-yl)-4-(trifluoromethyl)benzamide hydrochloride (214 mg) was obtained as an amorphous.

Example 109

Sodium triacetoxyborohydride (138 mg) was added to a dichloroethane (20 mL) solution of 2-{[(1S,2S)-2-aminocyclohexyl]amino}-N-(3,3-dimethyl-2-oxo-2,3-dihydro-1H-indol-6-yl)-4-(trifluoromethyl)benzamide (200 mg), cyclopentanone (40 mg) and acetic acid (29 mg), followed by stirring at room temperature for 1 day. Acetic acid (260 mg), cyclopentanone (140 mg) and sodium triacetoxyborohydride (140 mg) were added to the reaction liquid, followed by stirring for 1 day. A 1 M sodium hydroxide aqueous solution was added to the reaction liquid, followed by extraction with chloroform. The organic layer was concentrated under a reduced pressure. The residue was purified by silica gel column chromatography (chloroform:methanol, 1:0 to 85:15). By treating the resulting free base with 4 M hydrogen chloride/ethyl acetate, 2-{[(1S,2S)-2-(cyclopentylamino)cyclohexyl]amino}-N-(3,3-dimethyl-2-oxo-2,3-dihydro-1H-indol-6-yl)-4-(trifluoromethyl)benzamide hydrochloride (53 mg) was obtained as a white solid.

Example 110

Cyclohexanone (65 mg) was added to an ethanol (20 mL) solution of 2-{[(1S,2S)-2-aminocyclohexyl]amino}-N-(3,3-dimethyl-2-oxo-2,3-dihydro-1H-indol-6-yl)-4-(trifluoromethyl)benzamide (255 mg), followed by stirring at room temperature for 7 hours. The reaction liquid, sodium borohydride (25 mg) was added, followed by stirring for 1 day, and then sodium borohydride (41 mg) was added, followed by stirring for 2 hours. Water was added to the reaction liquid, followed by extraction with chloroform. The organic layer was concentrated under a reduced pressure. The resulting residue was purified by silica gel column chromatography (chloroform: methanol, 1:0 to 85:15). By treating the resulting free base with 4 M hydrogen chloride/ethyl acetate (1.0 ml), 2-{[(1S, 2S)-2-(cyclohexylamino)cyclohexyl]amino}-N-(3,3-dimethyl-2-oxo-2,3-dihydro-1H-indol-6-yl)-4-(trifluoromethyl) benzamide hydrochloride (51 mg) was obtained as a white solid.

Example 111

A mixture of 2-{[(1S,2S)-2-aminocyclohexyl]amino}-N-(3,3-dimethyl-2-oxo-2,3-dihydro-1H-indol-6-yl)-4-(trifluoromethyl)benzamide (207 mg), 2-iodopropane (114 mg), sodium carbonate (71 mg) and acetonitrile (2 mL) was, under microwave irradiation, stirred at 120° C. for 30 minutes and further stirred at 150° C. for 30 minutes. Water was added to the reaction liquid, followed by extraction with chloroform. The organic layer was concentrated under a reduced pressure. The residue was purified by silica gel column chromatography (chloroform:methanol, 1:0 to 85:15). By treating the resulting free base with 4 M hydrogen chloride/ethyl acetate (1.0 ml), N-(3,3-dimethyl-2-oxo-2,3-dihydro-1H-indol-6-yl)-2-{[(1S,2S)-2-(isopropyl)cyclohexyl]amino}-4-(trifluoromethyl)benzamide hydrochloride (140 mg) was obtained as a white solid.

Example 112

2-{[(1R,2S)-2-Pyrrolidin-1-ylcyclohexyl]amino}-4-(trifluoromethyl)benzoic acid (150 mg), quinolin-7-amine (67 mg), hydrochloride of 1-ethyl-3-[3-(N,N-dimethylamino) propyl]carbodiimide (121 mg) and 1-hydroxybenzotriazole (57 mg) were stirred at 110° C. for 15 minutes in N-methylpyrrolidone under microwave irradiation. A potassium carbonate aqueous solution was added to the reaction liquid, followed by extraction with ethyl acetate. The organic layer was concentrated under a reduced pressure, and the residue was purified by silica gel column chromatography (basic silica gel, hexane:ethyl acetate, 7:3 to 1:1). By treating the resulting free base with 4 M hydrogen chloride/ethyl acetate, 2-{[(1R,2S)-2-pyrrolidin-1-ylcyclohexyl]amino}-N-quinolin-7-yl-4-(trifluoromethyl)benzamide dihydrochloride (66 mg) was obtained as an amorphous.

Example 113

A mixture of 2-(cyclohexylamino)-6-fluoro-N-(1-methyl-2-oxo-1,2,3,4-tetrahydroquinolin-7-yl)nicotinamide (150 mg), piperidine (64 mg), potassium carbonate (63 mg) and DMF was stirred at 60° C. for 18 hours. Then, water was added, followed by extraction with ethyl acetate. After drying the organic layer with magnesium sulfate, the solution was concentrated under a reduced pressure, and the residue was purified by silica gel column chromatography (basic silica gel, hexane:ethyl acetate, 2:1 to 1:1) to obtain 2-(cyclohexylamino)-N-(1-methyl-2-oxo-1,2,3,4-tetrahydroquinolin-7-yl)-6-piperidin-1-ylnicotinamide (138 mg) as a solid.

Example 114

A mixture of [7-{[2-(cyclohexylamino)-4-(trifluoromethyl)benzoyl]amino}-2-oxo-3,4-dihydroquinolin-1(2H)-yl] acetic acid (70 mg), N,N'-carbonyldiimidazole (70 mg), methylamine aqueous solution (1 mL) and THF was stirred at room temperature for 3 hours, mixed with methanol and stirred for 20 minutes. A 0.5 M hydrochloric acid was added to the reaction liquid, followed by extraction with ethyl acetate. The organic layer was concentrated under a reduced pressure, and the residue was purified by silica gel column chromatography (chloroform:methanol, 20:1 to 10:1) to obtain 2-(cyclohexylamino)-N-{1-[2-(methylamino)-2-oxoethyl]-2-oxo-1,2,3,4-tetrahydroquinolin-7-yl}-4-(trifluoromethyl)benzamide (12 mg) as a solid.

Examples 115 to 430

In the same manner as the methods of Examples 1 to 5 and 95 to 114, the compounds of Examples 115 to 430 shown in Tables 26 to 51 which are described later were produced using respectively corresponding materials.

Structures and physicochemical data of the compounds of Examples 95 to 430 are shown in Tables 26 to 51.

In this connection, among the material amine compounds used in the amidation reaction described in the aforementioned Examples 1, 2, 98, 99, 106, 107 and 112 and in the production methods of the Example compounds in the following tables carried out by referring to their production methods, particularly those which are not described in the aforementioned Reference Examples are commercially available or can be easily produced by the method described in WO 2004/110986 and the like. In addition, 6-amino-3,3-dimethyl-1,3-dihydro-2H-indol-2-one was produced by the method described in Eur. Pat. Appl., 161632, 21 Nov., 1985.

Also, structures of other compounds of the present invention are shown in Tables 52 to 54. These can be easily synthesized by the aforementioned production methods and the methods described in the Examples and the methods which are obvious to those skilled in the art, or modified methods thereof.

In the following, those in which a symbol * was attached to the asymmetric carbon atom in the structures of the compounds of the Tables mean that said carbon atom has a single absolute configuration.

In the column "Syn" regarding the production methods in the following tables, compounds having different salt forming steps, namely salt forms, but produced by the same kind of reactions were named the same Example number. Interconversion between a free compound and its salt is a technical common sense of those skilled in the art.

TABLE 1

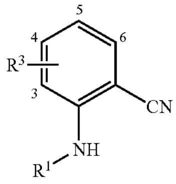

| REx | RSn | $R^3$ | $R^1$ | Dat |
|---|---|---|---|---|
| 1 | 1 | 4-Cl | cPen | ES: 221 |
| 2 | 2 | 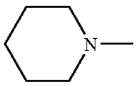 | cHex | F: 284 |
| 3 | 3 | 4-Cl | 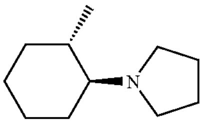 | F: 304 |
| 4 | 4 | 4-Cl | 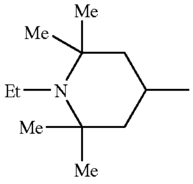 | F: 320 |
| 10 | 1 | 4-Cl | cHex | ES: 235 |
| 11 | 1 | 4-$CF_3$ | cPen | EI: 254 |
| 12 | 1 | 4-$CF_3$ | cHex | FN: 267 |
| 13 | 1 | 5-$CF_3$ | cHex | EI: 268 |
| 14 | 1 | H | cHex | F: 201 |

TABLE 1-continued

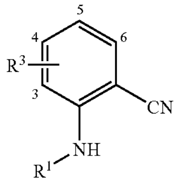

| REx | RSn | $R^3$ | $R^1$ | Dat |
|---|---|---|---|---|
| 15 | 1 | 4-Cl | 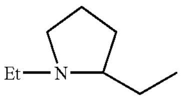 | F: 264 |
| 16 | 1 | 4-Cl | 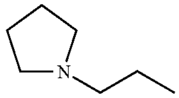 | F: 250 |
| 17 | 1 | 4-Cl | 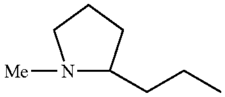 | F: 264 |
| 18 | 1 | 4-Cl | MeO—$C_2H_4$— | EI: 210 |
| 19 | 1 | 4-Cl | 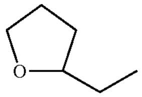 | F: 237 |
| 20 | 1 | 4-Cl | $Et_2CH$— | EI: 222 |
| 21 | 1 | 4-Cl | $Me_2CH$—$CH_2$— | EI: 208 |
| 22 | 1 | 4-Cl | 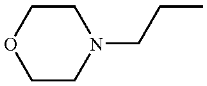 | F: 266 |
| 23 | 1 | 4-Cl | 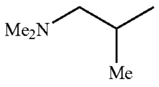 | F: 238 |
| 24 | 1 | 4-Cl | 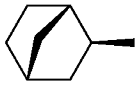 | F: 247 |
| 25 | 1 | 4-Cl | 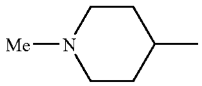 | F: 250 |
| 26 | 1 | 4-Ph | cHex | F: 277 |
| 27 | 1 | 4-Cl | 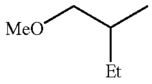 | F: 239 |

TABLE 1-continued
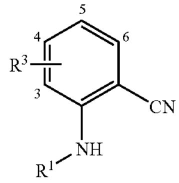
| REx | RSn | $R^3$ | $R^1$ | Dat |
|---|---|---|---|---|
| 28 | 1 | 4-Cl | EtO—$C_2H_4$— | EI: 224 |
| 29 | 1 | 4-Cl | MeO—$C_3H_6$— | F: 225 |
| 30 | 1 | 4-Cl | 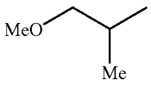 | EI: 224 |
| 31 | 1 | 4-Cl | 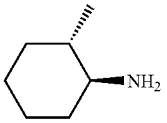 | F: 250 |
| 32 | 1 | 4-Cl | 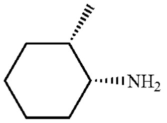 | F: 250 |
| 33 | 1 | 4-Cl | cPr | EI: 192 |
| 34 | 1 | 4-Cl | 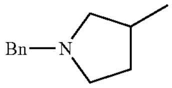 | F: 312 |
| 35 | 1 | 4-Cl | 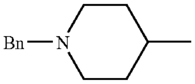 | F: 326 |
| 36 | 1 | 4-Cl | $iPr_2N$—$C_2H_4$— | F: 280 |
| 37 | 1 | 4-$CF_3$ | MeO—$C_2H_4$— | EI: 244 |
TABLE 2
| | | | | |
|---|---|---|---|---|
| 38 | 1 | 4-Cl | 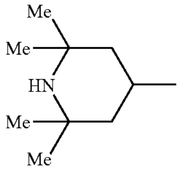 | F: 292 |
| 39 | 1 | 4-Cl | 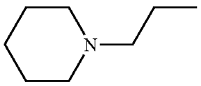 | F: 264 |
| 40 | 1 | 4-Cl | $Et_2N$—$C_2H_4$— | F: 252 |
| 41 | 1 | 4-Cl | MeS—$C_2H_4$— | EI: 226 |
| 42 | 1 | 4-$CF_3$ | 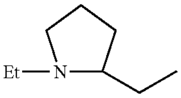 | F: 298 |
TABLE 2-continued
| | | | | |
|---|---|---|---|---|
| 43 | 1 | 4-$CF_3$ | 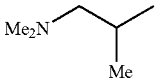 | F: 272 |
| 44 | 1 | 4-Cl | 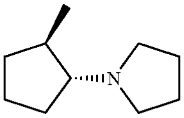 | F: 290 |
| 45 | 1 | 4-Cl | 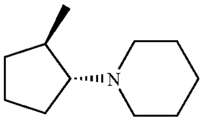 | F: 304 |
| 46 | 1 | 4-Cl | 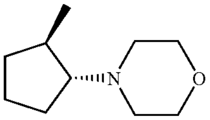 | F: 306 |
| 47 | 1 | 4-Cl | 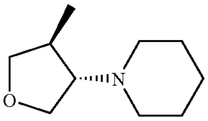 | F: 306 |
| 48 | 1 | 4-Cl | 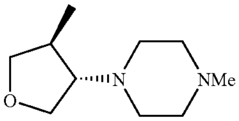 | F: 321 |
| 49 | 1 | 4-Cl | 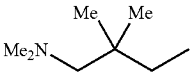 | F: 266 |
| 50 | 1 | 4-Cl | 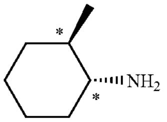 | F: 250 |
| 51 | 1 | 4-Cl | 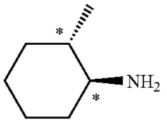 | F: 250 |
| 52 | 1 | 4-Cl | 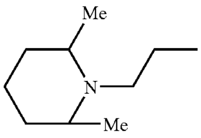 | F: 292 |
| 53 | 1 | 4-Cl | 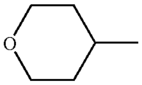 | ES: 237 |
| 54 | 1 | 4-Cl | 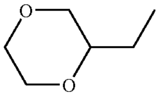 | F: 253 |
| 55 | 1 | 4-Cl | 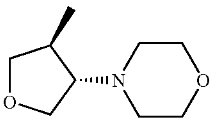 | ES: 308 |

TABLE 2-continued
| | | | | |
|---|---|---|---|---|
| 56 | 1 | 4-Cl | $Et_2N—C_3H_6—$ | F: 266 |
| 57 | 1 | 4-Cl | 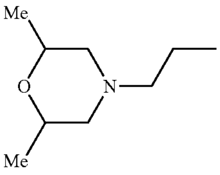 | EI: 293 |
| 58 | 1 | 4-Cl | 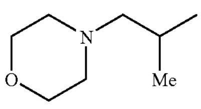 | EI: 279 |
| 59 | 1 | $4-CF_3$ | 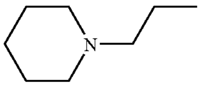 | F: 298 |
| 60 | 1 | $4-CF_3$ | $Et_2N—C_2H_4—$ | F: 286 |
| 61 | 1 | 4-Cl | $Et_2N—C_4H_8—$ | ES: 280 |
| 62 | 1 | 4-Cl | 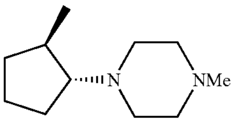 | F: 319 |
TABLE 2-continued
| | | | | |
|---|---|---|---|---|
| 63 | 1 | 4-Cl | 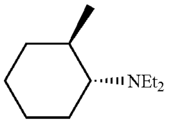 | F: 306 |
| 64 | 1 | 4-Cl | cHep | F: 249 |
| 65 | 1 | 4-Cl | 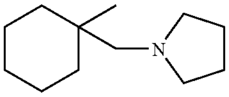 | F: 318 |
| 66 | 3 | 4-Cl | 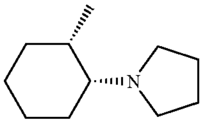 | F: 304 |
| 67 | 3 | 4-Cl | 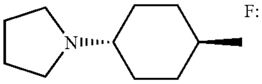 | F: 304 |
| 68 | 3 | 4-Cl | 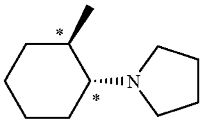 | F: 304 |
| 69 | 3 | 4-Cl | 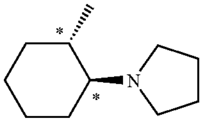 | F: 304 |
TABLE 3
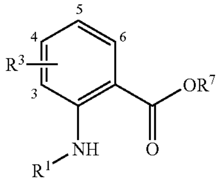
| REx | RSn | $R^3$ | $R^1$ | $R^7$ | Dat |
|---|---|---|---|---|---|
| 5 | 5 | 5-Cl | cHex | Me | F: 234 |
| 6 | 6 | 5- 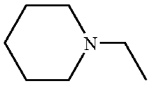 | cHex | Me | F: 317 |
| 70 | 5 | 5-Me | cHex | H | F: 234 |
| 71 | 5 | 6-Cl | cHex | H | F: 254 |
| 72 | 5 | 4-Cl | 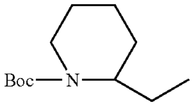 | H | F: 369 |

TABLE 4
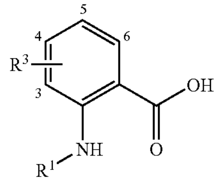
| REx | RSn | $R^3$ | $R^1$ | Dat |
|---|---|---|---|---|
| 7 | 7 | 4-Cl | cPen | ES: 240 |
| 8 | 8 | 4-Cl | 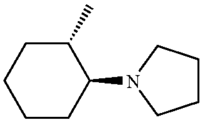 | F: 323 |
| 9 | 9 | 5-Cl | cHex | F: 254 |
| 73 | 7 | 4-Cl | cHex | ES: 254 |
| 74 | 7 | $4\text{-}CF_3$ | cPen | F: 274 |
| 75 | 7 | $4\text{-}CF_3$ | cHex | F: 288 |
| 76 | 7 | $5\text{-}CF_3$ | cHex | F: 288 |
| 77 | 7 | 4- 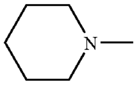 | cHex | ES: 303 |
| 78 | 7 | H | cHex | F: 220 |
| 79 | 7 | 4-Cl | 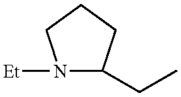 | F: 283 |
| 80 | 7 | 4-Cl | 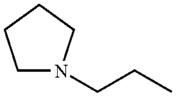 | F: 269 |
| 81 | 7 | 4-Cl | 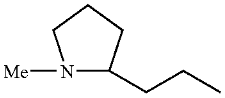 | F: 283 |
| 82 | 8 | 4-Cl | 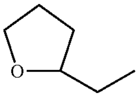 | F: 256 |
| 83 | 8 | 4-Cl | $Et_2CH$— | F: 242 |
| 84 | 8 | 4-Cl | $Me_2CH$—$CH_2$— | F: 228 |
| 85 | 8 | 4-Cl | 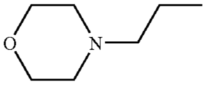 | F: 285 |
| 86 | 8 | 4-Cl | 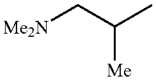 | F: 257 |
| 87 | 8 | 4-Cl | 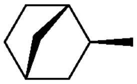 | F: 266 |
TABLE 5
| | | | | |
|---|---|---|---|---|
| 88 | 8 | 4-Cl | 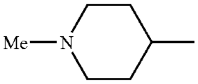 | F: 269 |
| 89 | 8 | 4-Ph | cHex | F: 296 |
| 90 | 8 | 4-Cl | 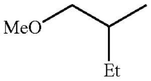 | F: 258 |
| 91 | 8 | 4-Cl | EtO—$C_2H_4$— | F: 244 |
| 92 | 8 | 4-Cl | MeO—$C_3H_6$— | F: 244 |
| 93 | 8 | 4-Cl | 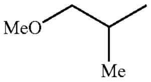 | F: 244 |
| 94 | 8 | 4-Cl | MeO—$C_2H_4$— | F: 230 |
| 95 | 8 | 4-Cl | 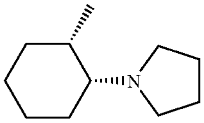 | F: 323 |
| 96 | 8 | 4-Cl | cPr | F: 212 |
| 97 | 8 | 4-Cl | 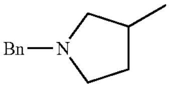 | F: 331 |
| 98 | 8 | 4-Cl | 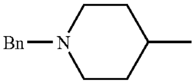 | F: 345 |
| 99 | 8 | 4-Cl | $iPr_2N$—$C_2H_4$— | F: 299 |
| 100 | 8 | $4\text{-}CF_3$ | MeO—$C_2H_4$— | F: 264 |
| 101 | 8 | 4-Cl | 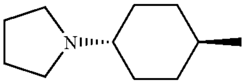 | FS: 323 |
| 102 | 8 | 4-Cl | 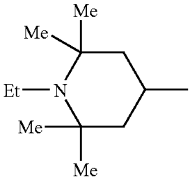 | F: 339 |
| 103 | 8 | 4-Cl | 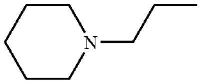 | F: 283 |
| 104 | 8 | 4-Cl | $Et_2N$—$C_2H_4$— | F: 271 |
| 105 | 8 | 4-Cl | MeS—$C_2H_4$— | FN: 244 |
| 106 | 8 | $4\text{-}CF_3$ | 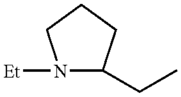 | F: 317 |
| 107 | 8 | $4\text{-}CF_3$ | 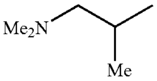 | F: 291 |

TABLE 5-continued
| | | | | |
|---|---|---|---|---|
| 108 | 8 | 4-Cl | 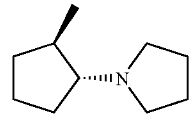 | F: 309 |
| 109 | 8 | 4-Cl | 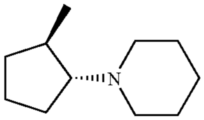 | F: 323 |
| 110 | 8 | 4-Cl | 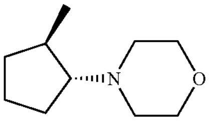 | F: 325 |
| 111 | 8 | 4-Cl | 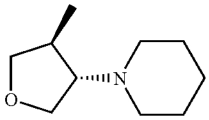 | F: 325 |
| 112 | 8 | 4-Cl | 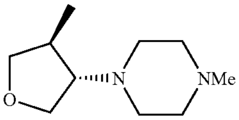 | F: 340 |
| 113 | 8 | 4-Cl | 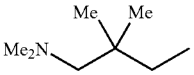 | F: 285 |
| 114 | 8 | 4-Cl | 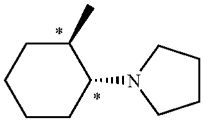 | F: 323 |
| 115 | 8 | 4-Cl | 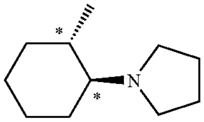 | F: 323 |
| 116 | 8 | 4-Cl | 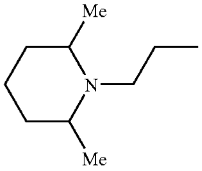 | ES: 311 |
| 117 | 8 | 4-Cl | 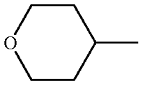 | F: 256 |
| 118 | 8 | 4-Cl | 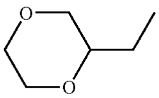 | F: 272 |
| 119 | 8 | 4-Cl | 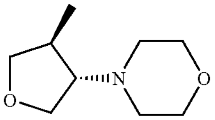 | ES: 327 |
TABLE 6
| | | | | |
|---|---|---|---|---|
| 120 | 8 | 4-Cl | $Et_2N—C_3H_6—$ | F: 285 |
| 121 | 8 | 4-Cl | 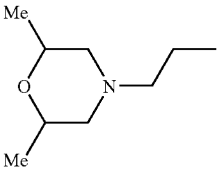 | F: 313 |
| 122 | 8 | 4-Cl | 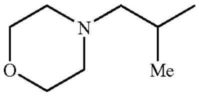 | F: 299 |
| 123 | 8 | 4-$CF_3$ | 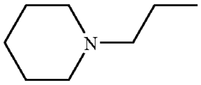 | F: 317 |
| 124 | 8 | 4-$CF_3$ | $Et_2N—C_2H_4—$ | F: 305 |
| 125 | 8 | 4-Cl | $Et_2N—C_4H_8—$ | F: 299 |
| 126 | 8 | 4-Cl | 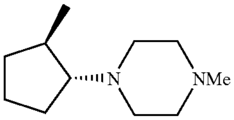 | F: 338 |
| 127 | 8 | 4-Cl | 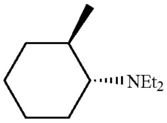 | F: 325 |
| 128 | 8 | 4-Cl | cHep | F: 268 |
| 129 | 8 | 4-Cl | 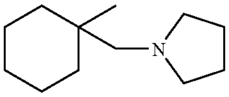 | F: 337 |
| 130 | 9 | 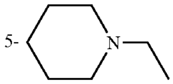 | cHex | F: 317 |
TABLE 7
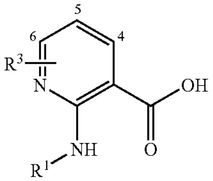
| REx | RSn | $R^3$ | $R^1$ | Dat |
|---|---|---|---|---|
| 131 | 1 | H | cHex | F: 221 |
| 132 | 1 | 6-$CF_3$ | cHex | F: 289 |

TABLE 8
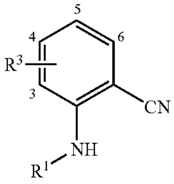
| REx | RSn | $R^3$ | $R^1$ | Dat |
|---|---|---|---|---|
| 133 | 133 | 4- 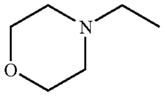 | cHex | ES: 300 |
| 134 | 134 | 4-Cl, 5-Cl | 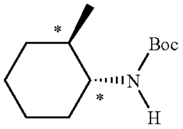 | F: 384 |
| 135 | 135 | 4-Cl | 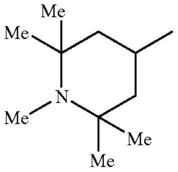 | F: 306 |
| 136 | 136 | 4-Cl, | 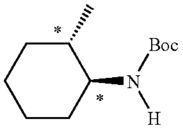 | F: 350 |
| 137 | 137 | 4-Cl, 5-Bl | 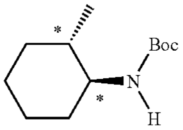 | F: 429 |
| 138 | 138 | 4-Cl, 5-Me | 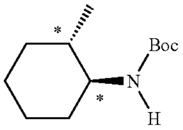 | F: 364 |
| 139 | 139 | 4-Cl, 5-Me | 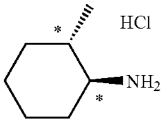 | ES: 264 |
| 140 | 140 | 4-Cl | 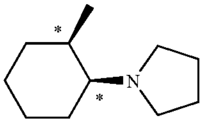 | F: 304 |
| 141 | 141 | $4\text{-}CF_3$ | 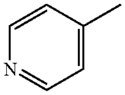 | APCI: 264 |
| 142 | 142 | 4-Cl | 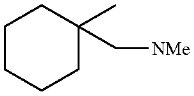 | F: 292 |
TABLE 8-continued
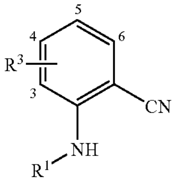
| REx | RSn | $R^3$ | $R^1$ | Dat |
|---|---|---|---|---|
| 143 | 143 | $4\text{-}CF_3$ | 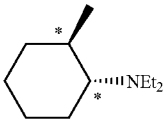 | ES: 340 |
| 144 | 144 | $4\text{-}CF_3$ | 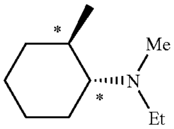 | ES: 326 |
| 180 | 1 | $4\text{-}CF_3$ | 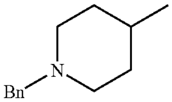 | F: 360 |
| 181 | 1 | 4-Cl | 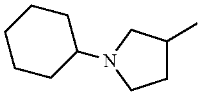 | ES: 304 |
| 182 | 1 | $4\text{-}CF_3$ | 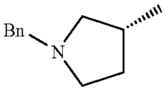 | F: 346 |
| 183 | 1 | 4-Cl | 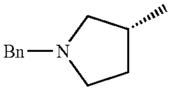 | F: 312 |
| 184 | 1 | $4\text{-}CF_3$ | 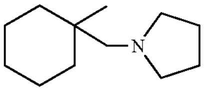 | F: 352 |
| 185 | 1 | 4-Cl | 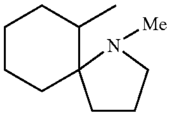 | F: 304 |
| 186 | 1 | $4\text{-}CF_3$ | 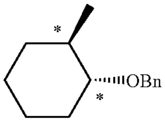 | ESN: 373 |
| 187 | 1 | 4-Cl | 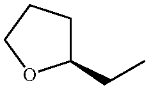 | F: 237 |
| 188 | 1 | 4-Cl | 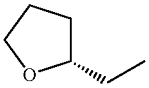 | F: 237 |
| 189 | 1 | 4-Cl | 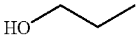 | EI: 196 |

TABLE 8-continued
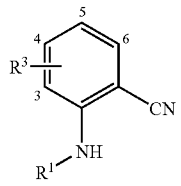
| REx | RSn | $R^3$ | $R^1$ | Dat |
|---|---|---|---|---|
| 190 | 1 | 4-$CF_3$ | 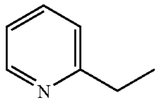 | APCI: 278 |
| 191 | 1 | 4-Cl | 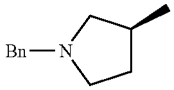 | F: 312 |
TABLE 9
| | | | | |
|---|---|---|---|---|
| 192 | 1 | 4-$CF_3$ | 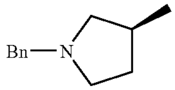 | F: 346 |
| 193 | 1 | 4-$CF_3$ | 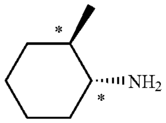 | F: 284 |
| 194 | 1 | 4-$CF_3$ | 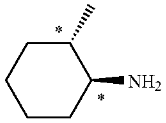 | F: 284 |
| 195 | 1 | 4-$CF_3$ | 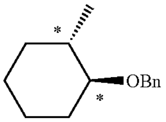 | APCI: 375 |
| 196 | 1 | 4-Cl | 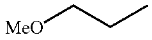 | EI: 210 |
| 197 | 1 | 4-OMe | 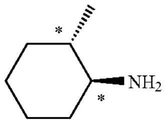 | F: 284 |
| 198 | 1 | 4-Br | 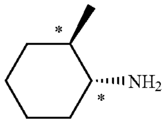 | ES: 294 |
| 199 | 1 | 4-Me | 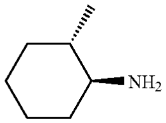 | F: 230 |
TABLE 9-continued
| | | | | |
|---|---|---|---|---|
| 200 | 1 | 4-tBu | 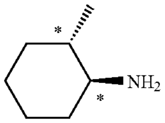 | F: 272 |
| 201 | 1 | 4-$CF_3$ | cHex | F: 268 |
| 202 | 1 | 4-Cl | 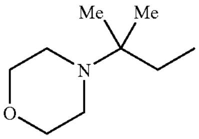 | ES: 294 |
| 203 | 1 | 4-$CF_3$ | 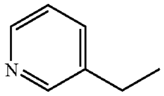 | APCI: 278 |
| 204 | 1 | 4-Cl | 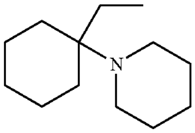 | F: 332 |
| 205 | 1 | 4-Br | 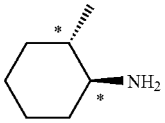 | ES: 294 |
| 206 | 1 | 3-$CF_3$ | cHex | F: 269 |
| 207 | 3 | 4-$CF_3$ | 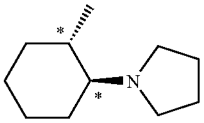 | F: 338 |
| 208 | 3 | 4-tBu | 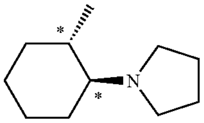 | F: 326 |
| 209 | 3 | 4-Br | 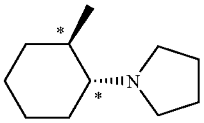 | F: 348 |
| 210 | 3 | 4-Cl, 5-Br | 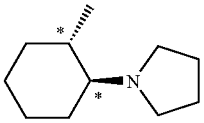 | APCI: 382 |
| 211 | 3 | 4-$CF_3$ | 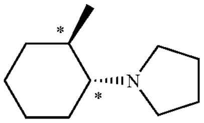 | F: 338 |
| 212 | 3 | 4-Cl, 5-Me | 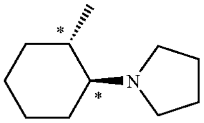 | F: 318 |

TABLE 9-continued
| | | | | |
|---|---|---|---|---|
| 213 | 3 | 4-Cl, 5-Me | 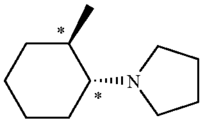 | F: 318 |
| 214 | 3 | 4-Cl, 5-Cl | 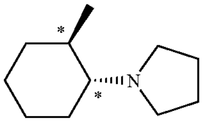 | F: 338 |
| 215 | 3 | 4-$CF_3$ | 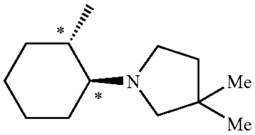 | F: 336 |
| 216 | 3 | 4-Me | 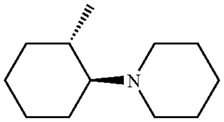 | F: 338 |
| 217 | 3 | 4-Cl | 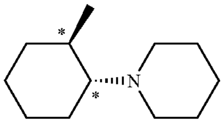 | F: 318 |
| 218 | 3 | 4-Cl, 5-Cl | 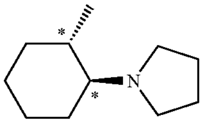 | ES: 286 |
| 219 | 3 | 4-OMe | 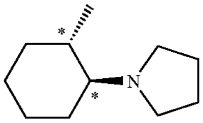 | ES: 300 |
| 220 | 3 | 4-Cl | 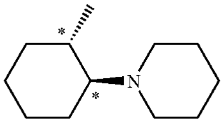 | F: 318 |
| 221 | 3 | 4-$CF_3$ | 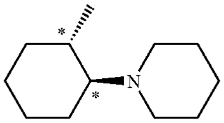 | F: 352 |
TABLE 10
| | | | | |
|---|---|---|---|---|
| 222 | 3 | 4-Br | 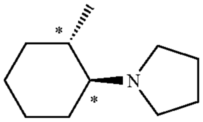 | F: 348 |
| 223 | 3 | 5-Cl | 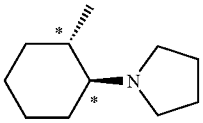 | F: 304 |
TABLE 10-continued
| | | | | |
|---|---|---|---|---|
| 224 | 134 | 4-Cl, 5-Cl | 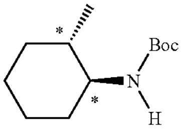 | F: 384 |
| 225 | 135 | 4-$CF_3$ | 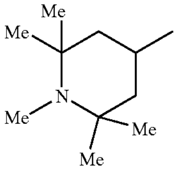 | F: 340 |
| 226 | 139 | 4-Cl, 5-Br | 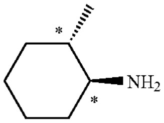 | ES: 330 |
| 227 | 139 | 4-Cl, 5-Cl | 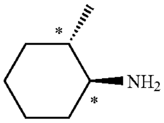 | F: 284 |
| 228 | 139 | 4-Cl, 5-Me | 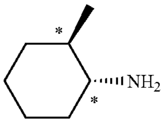 | APCI: 264 |
| 229 | 140 | 4-$CF_3$ | 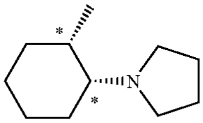 | ES: 338 |
| 230 | 140 | 4-Cl | tBu | EI: 208 |
| 231 | 140 | 4-$CF_3$ | 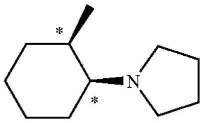 | F: 338 |
| 232 | 140 | 4-Cl | 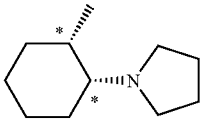 | F: 304 |
| 233 | 140 | 4-Cl | 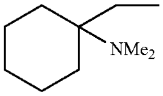 | F: 292 |
| 234 | 140 | 4-Cl | 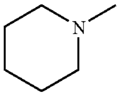 | EI: 235 |
| 235 | 141 | 4-$CF_3$ | 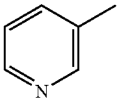 | APCI: 264 |

TABLE 10-continued
| | | | | |
|---|---|---|---|---|
| 236 | 143 | $4-CF_3$ | 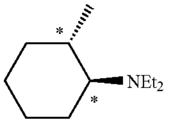 | ES: 340 |
| 237 | 143 | 4-Cl | 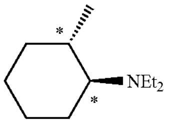 | APCI: 306 |
TABLE 11
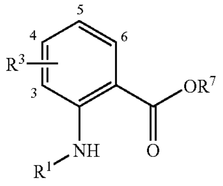
| REx | RSn | $R^3$ | $R^1$ | $R^7$ | Dat |
|---|---|---|---|---|---|
| 145 | 145 | $4-CF_3$ | 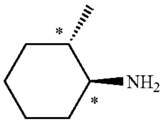 | Me | F: 317 |
| 146 | 146 | $4-CF_3$ | 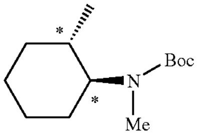 | Me | F: 431 |
| 147 | 147 | $4-NH_2$ | 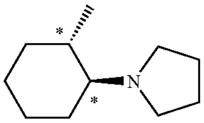 | Et | F: 332 |
| 148 | 148 | 4-F | 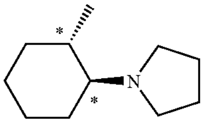 | Et | F: 335 |
| 238 | 1 | 4-CN | 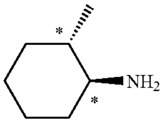 | Me | F: 274 |
| 239 | 1 | 5-Br | 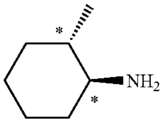 | Et | F: 341 |
| 240 | 1 | $4-NO_2$ | 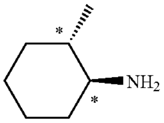 | Et | F: 308 |
TABLE 11-continued
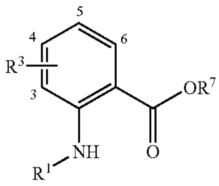
| REx | RSn | $R^3$ | $R^1$ | $R^7$ | Dat |
|---|---|---|---|---|---|
| 241 | 1 | 4-Cl, 5-F | 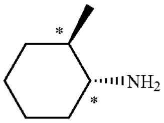 | Et | F: 315 |
| 242 | 1 | 4-Cl, 5-F | 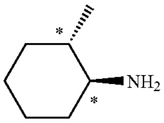 | Et | F: 315 |
| 243 | 1 | $4-NO_2$ | 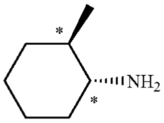 | Et | F: 308 |
| 244 | 3 | $4-NO_2$ | 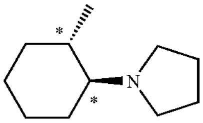 | Et | F: 362 |
| 245 | 3 | 4-CN | 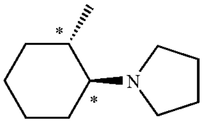 | Me | F: 328 |
| 246 | 3 | 5-Br | 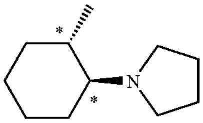 | Et | F: 395 |
| 247 | 3 | 4-Cl, 5-F | 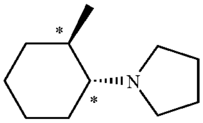 | Et | ES: 369 |
| 248 | 3 | 4-Cl, 5-F | 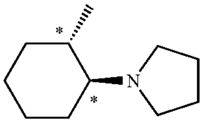 | Et | ES: 369 |
| 249 | 3 | $4-NO_2$ | 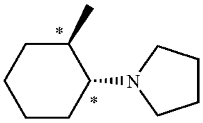 | Et | F: 362 |
| 250 | 136 | $4-CF_3$ | 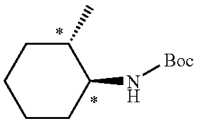 | Me | F: 417 |

TABLE 12
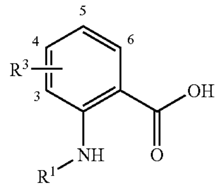
| REx | RSn | $R^3$ | $R^1$ | Dat |
|---|---|---|---|---|
| 149 | 149 | 4-$CF_3$ | 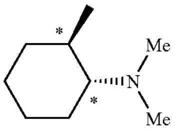 | F: 331 |
| 150 | 150 | 4-$CF_3$ | 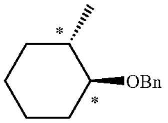 | ES: 394 |
| 251 | 5 | 4-Cl | cHex | F: 254 |
| 252 | 5 | 5-F | cHex | F: 238 |
| 253 | 5 | 4-F | cHex | F: 238 |
| 254 | 8 | 4-Cl | 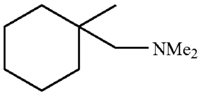 | F: 311 |
| 255 | 8 | 4-$CF_3$ | 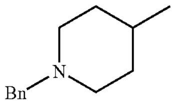 | F: 379 |
| 256 | 8 | 4-$CF_3$ | 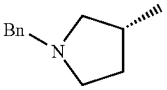 | F: 365 |
| 257 | 8 | 4-Cl | 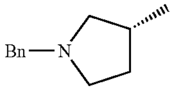 | ES: 331 |
| 258 | 8 | 4-Cl | 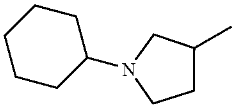 | ES: 323 |
| 259 | 8 | 4-Cl | 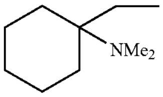 | ES: 311 |
| 260 | 8 | 4-Cl | 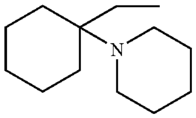 | F: 351 |
| 261 | 8 | 4-Cl | 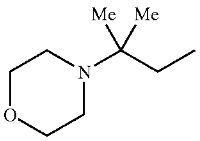 | ES: 313 |
TABLE 12-continued
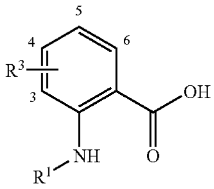
| REx | RSn | $R^3$ | $R^1$ | Dat |
|---|---|---|---|---|
| 262 | 8 | 4-Cl | 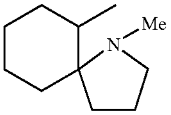 | F: 323 |
| 263 | 8 | 4-Cl | 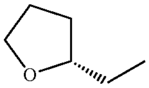 | F: 256 |
| 264 | 8 | 4-Me | 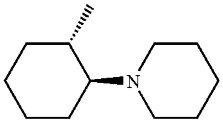 | F: 317 |
| 265 | 8 | 4-$CF_3$ | 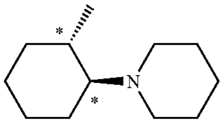 | F: 371 |
| 266 | 8 | 4-Cl | tBu | F: 228 |
| 267 | 8 | 4-$CF_3$ | 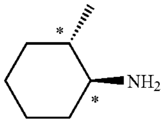 | F: 303 |
| 268 | 8 | 4-$CF_3$ | cHex | F: 288 |
| 269 | 8 | 4-Cl | 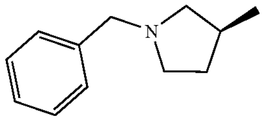 | ES: 331 |
| 270 | 8 | 4-$CF_3$ | 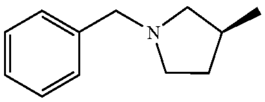 | F: 365 |
| 271 | 8 | 4-Cl, 5-Cl | 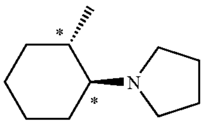 | F: 357 |
| 272 | 8 | 4-Cl, 5-Cl | 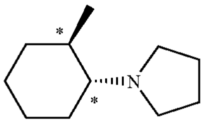 | F: 357 |
| 273 | 8 | 4-Br | 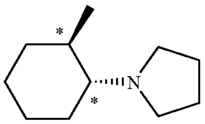 | F: 367 |

TABLE 12-continued
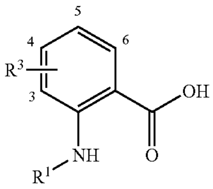
| REx | RSn | $R^3$ | $R^1$ | Dat |
|---|---|---|---|---|
| 274 | 8 | 4-$CF_3$ | 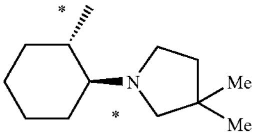 | F: 385 |
TABLE 13
| | | | | |
|---|---|---|---|---|
| 275 | 8 | 4-Cl, 5-Me | 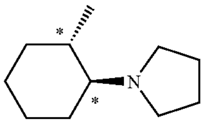 | F: 337 |
| 276 | 8 | 4-Cl, 5-Me | 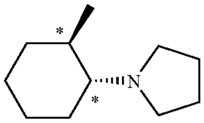 | F: 337 |
| 277 | 8 | 4-Cl | 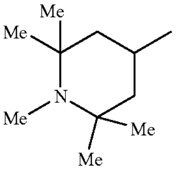 | ES: 325 |
| 278 | 8 | 5-Cl | cHex | F: 303 |
| 279 | 8 | 4- 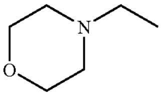 | 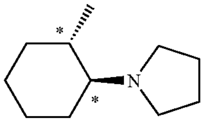 | F: 323 |
| 280 | 8 | 4-Cl | 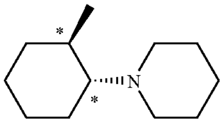 | F: 337 |
| 281 | 8 | 4-Cl | 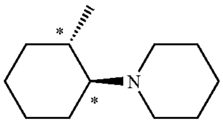 | ES: 337 |
| 282 | 8 | 4-Cl | 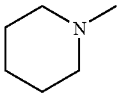 | F: 255 |
TABLE 13-continued
| | | | | |
|---|---|---|---|---|
| 283 | 8 | 4-$CF_3$ | 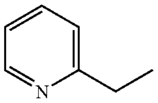 | ES: 297 |
| 284 | 8 | 4-$CF_3$ | 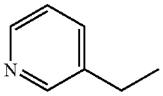 | APCI: 297 |
| 285 | 8 | 4-$CF_3$ | 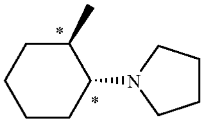 | F: 357 |
| 286 | 8 | 4-Cl | 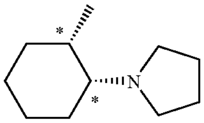 | F: 323 |
| 287 | 8 | 4-Cl | 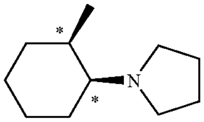 | F: 323 |
| 288 | 8 | 4-$CF_3$ | 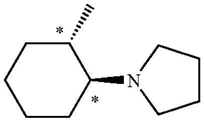 | F: 357 |
| 289 | 8 | 4-Cl | 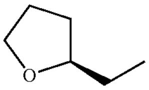 | F: 256 |
| 290 | 8 | 4-$CF_3$ | 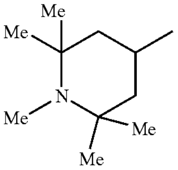 | F: 359 |
| 291 | 8 | 3- 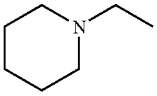 | cHex | ES: 317 |
| 292 | 8 | 4-tBu | 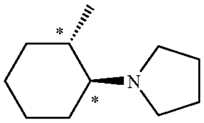 | F: 345 |
| 293 | 8 | 4-Br | 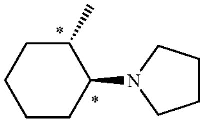 | ES: 367 |
| 294 | 8 | 4-Cl, 5-Br | 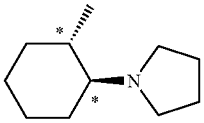 | APCI: 403 |

TABLE 13-continued
| | | | | |
|---|---|---|---|---|
| 295 | 8 | 4-Cl | 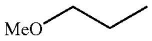 | F: 230 |
| 296 | 8 | $4\text{-}CF_3$ | 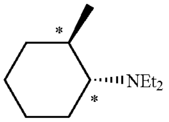 | ES: 359 |
| 297 | 8 | $4\text{-}CF_3$ | 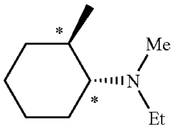 | ESN: 343 |
| 298 | 8 | $4\text{-}CF_3$ | 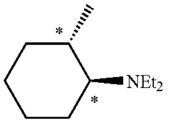 | ES: 359 |
| 299 | 8 | 4-Cl | 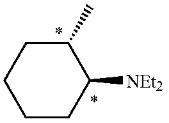 | ES: 359 |
| 300 | 8 | 4-Cl | 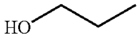 | F: 216 |
TABLE 14
| | | | | |
|---|---|---|---|---|
| 301 | 8 | $4\text{-}CF_3$ | 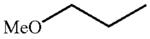 | F: 264 |
| 302 | 9 | 4-Cl, 5-F | 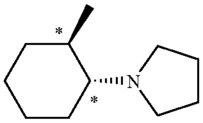 | F: 341 |
| 303 | 9 | 4-Cl, 5-F | 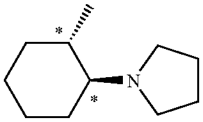 | F: 341 |
| 304 | 9 | $4\text{-}NO_2$ | 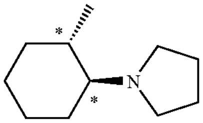 | ES: 334 |
| 305 | 9 | $4\text{-}NO_2$ | 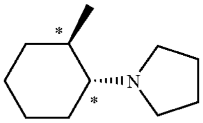 | ES: 334 |
| 306 | 9 | 4-F | 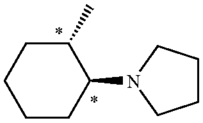 | ES: 307 |
| 307 | 9 | 5-Br | 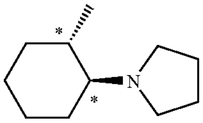 | ES: 367 |
TABLE 14-continued
| | | | | |
|---|---|---|---|---|
| 308 | 9 | $4\text{-}CF_3$ | 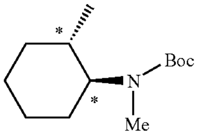 | F: 417 |
| 309 | 9 | 4-CN | 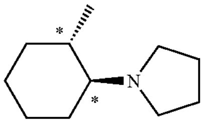 | ES: 314 |
| 310 | 140 | 4-CN | cHex | ES: 243 |
| 311 | 149 | 4-Cl | 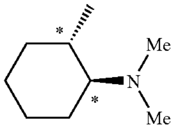 | ES: 297 |
| 312 | 149 | $4\text{-}CF_3$ | 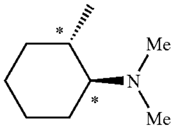 | F: 331 |
| 313 | 150 | $4\text{-}CF_3$ | 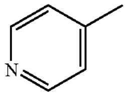 | ES: 283 |
| 314 | 150 | $4\text{-}CF_3$ | 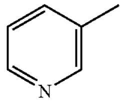 | ES: 283 |
| 315 | 150 | $4\text{-}CF_3$ | 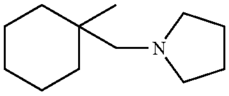 | ES: 372 |
| 316 | 150 | 4-OMe | 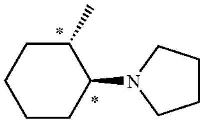 | ES: 319 |
| 317 | 150 | $4\text{-}CF_3$ | 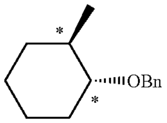 | ES: 394 |
| 318 | 150 | $4\text{-}CF_3$ | 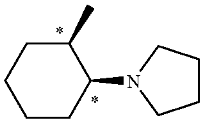 | ES: 357 |
| 319 | 150 | $4\text{-}CF_3$ | 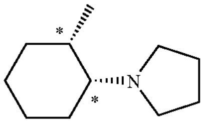 | APCI: 357 |

TABLE 15
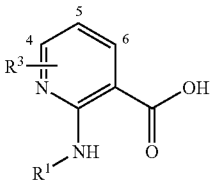
| REx | RSn | $R^3$ | $R^1$ | Dat |
|---|---|---|---|---|
| 151 | 151 | 5-Cl | 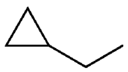 | ES: 227 |
| 152 | 152 | H | 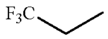 | ES: 221 |
| 153 | 153 | 4-$CF_3$ | 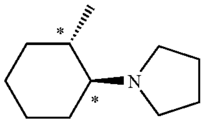 | F: 358 |
| 154 | 154 | H | 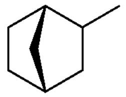 | F: 233 |
| 155 | 155 | 4-Cl | cHex | ES: 255 |
| 156 | 156 | 4-F | cHex | ES: 267 |
| 157 | 157 | 4-MeO | cHex | F: 251 |
| 320 | 1 | 4-$CF_3$ | 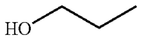 | F: 251 |
| 321 | 1 | 4-$CF_3$ | 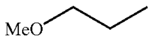 | F: 265 |
| 322 | 9 | 4-Cl | 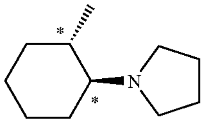 | F: 324 |
| 323 | 9 | 4-$CF_3$ | 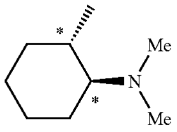 | F: 332 |
| 324 | 9 | 4-$OCH_2$—$CF_3$ | 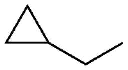 | ES: 291 |
| 325 | 153 | 4-$CF_3$ | 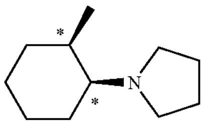 | ES: 358 |
| 326 | 153 | 4-$CF_3$ | 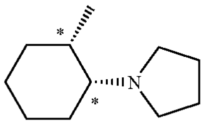 | ES: 358 |
| 327 | 153 | 4-$CF_3$ | 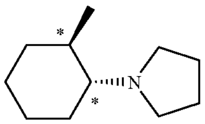 | F: 358 |
TABLE 15-continued
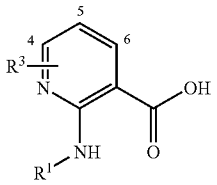
| REx | RSn | $R^3$ | $R^1$ | Dat |
|---|---|---|---|---|
| 328 | 154 | 4-Me | cHex | ES: 235 |
| 329 | 154 | H | 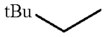 | F: 209 |
| 330 | 154 | H | cPen | F: 207 |
| 331 | 154 | H | 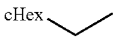 | ES: 235 |
| 332 | 154 | H | 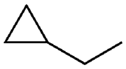 | ES: 193 |
| 333 | 154 | H | 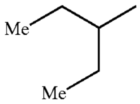 | F: 209 |
TABLE 16
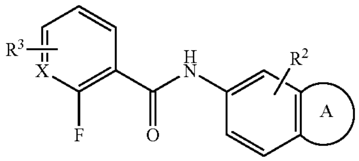
| REx | RSn | $R^3$ | X | 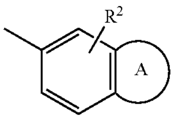 | Dat |
|---|---|---|---|---|---|
| 158 | 158 | 4-$CF_3$ | CH | 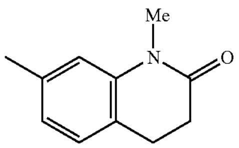 | F: 367 |
| 334 | 158 | 4-$CF_3$ | CH | 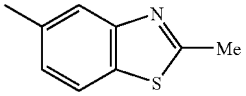 | F: 355 |
| 335 | 158 | 4-$CF_3$ | CH | 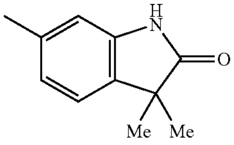 | ES: 367 |

TABLE 17
| REx | RSn | Str | Dat |
|---|---|---|---|
| 159 | 159 | 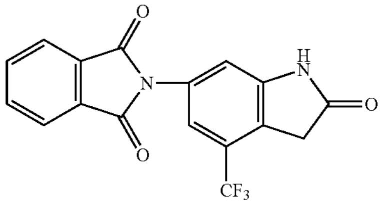 | ES: 347 |
| 160 | 160 | 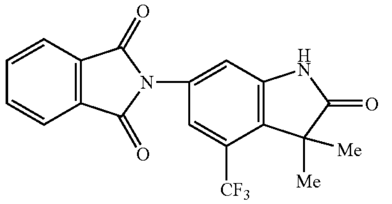 | F: 375 |
| 161 | 161 | 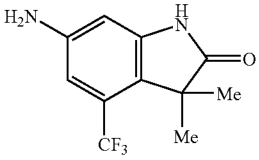 | F: 245 |
| 162 | 162 | 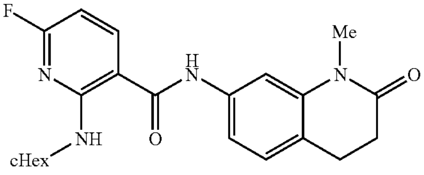 | F: 397 |
| 163 | 163 | 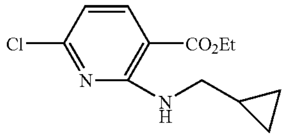 | ES: 255 |
| 164 | 164 | 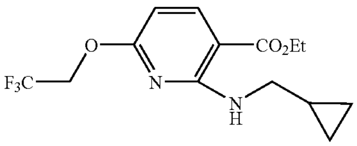 | ES: 319 |
| 165 | 165 | 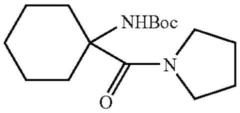 | F: 297 |
| 166 | 166 | 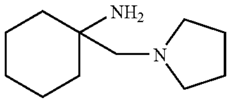 | F: 183 |
| 167 | 167 | 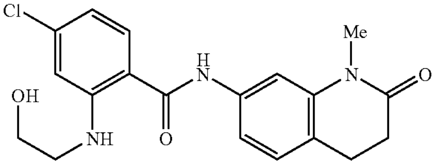 | ESN: 372 |

TABLE 17-continued
| REx | RSn | Str | Dat |
|---|---|---|---|
| 168 | 168 | 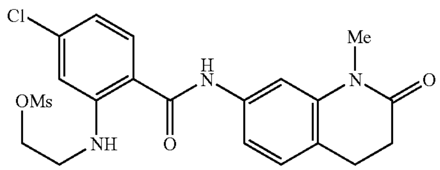 | F: 452 |
| 169 | 169 | 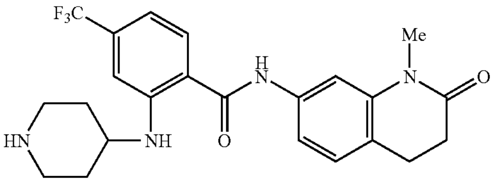 | F: 447 |
| 170 | 170 | 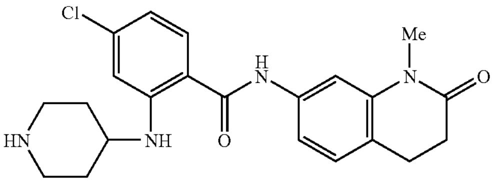 | ES: 413 |
| 171 | 171 | 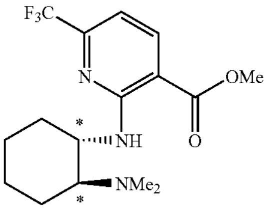 | F: 346 |
| 172 | 172 | 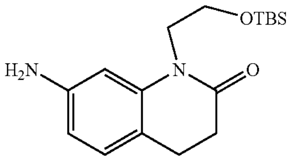 | F: 321 |
| 173 | 173 | 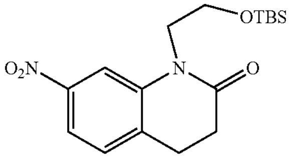 | F: 351 |
| 174 | 174 | 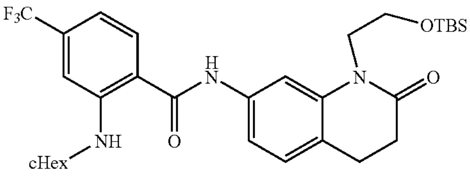 | F: 590 |
| 175 | 175 | 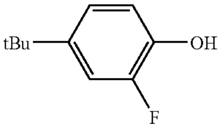 | F: 168 |
| 176 | 176 | 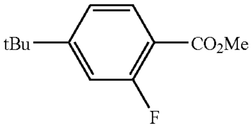 | EI: 210 |

TABLE 17-continued
| REx | RSn | Str | Dat |
|---|---|---|---|
| 177 | 177 | 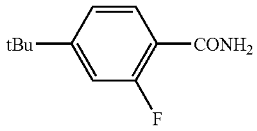 | EI:195 |
| 178 | 178 | 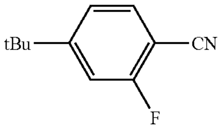 | EI: 177 |
| 179 | 179 | 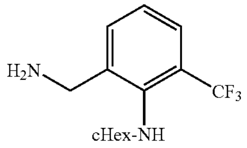 | F: 273 |
| 336 | 1 | 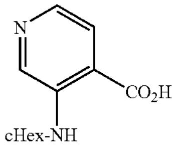 | F: 221 |
| 337 | 1 | 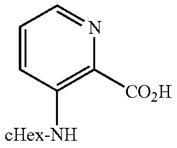 | ES: 221 |
| 338 | 1 | 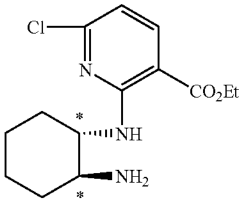 | ES: 298 |
TABLE 18
| | | | |
|---|---|---|---|
| 339 | 3 | 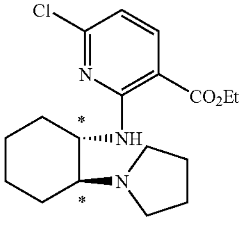 | F: 352 |
| 340 | 3 | 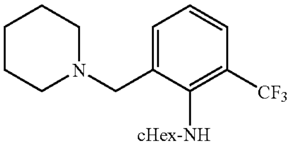 | F: 341 |

TABLE 18-continued
| | | | |
|---|---|---|---|
| 341 | 139 | 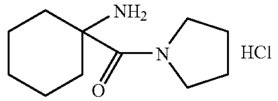 | F: 197 |
| 342 | 140 | 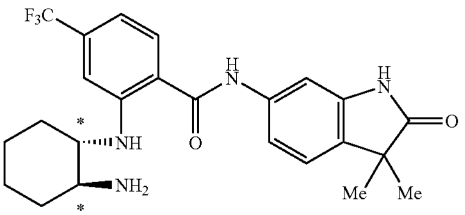 | AP: 461 |
| 343 | 169 | 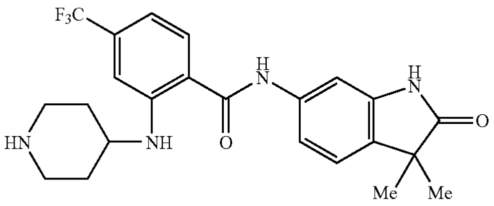 | F: 447 |
| 344 | 169 | 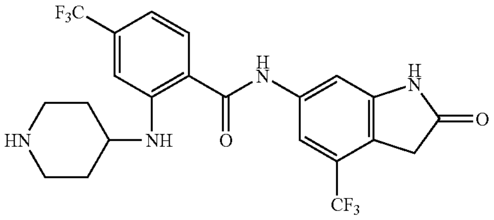 | F: 487 |
| 345 | 169 | 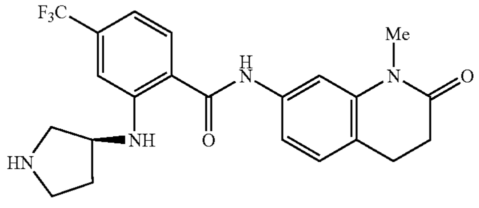 | F: 433 |
| 346 | 169 | 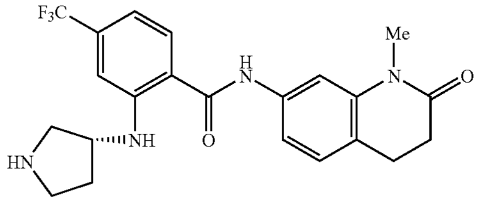 | F: 433 |
| 347 | 169 | 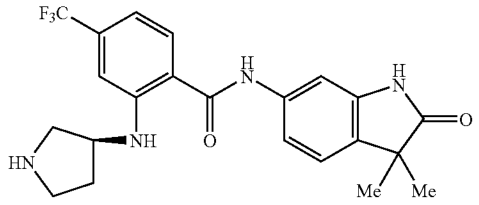 | F: 433 |
| 348 | 169 | 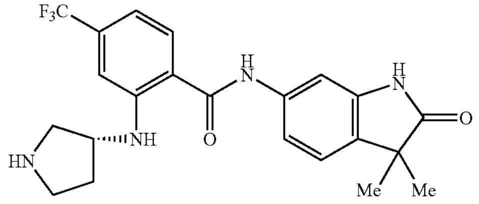 | F: 433 |

TABLE 18-continued
| | | | |
|---|---|---|---|
| 349 | 160 | 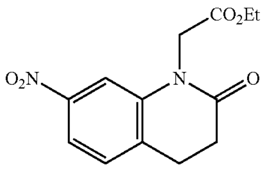 | F: 279 |
| 350 | 172 | 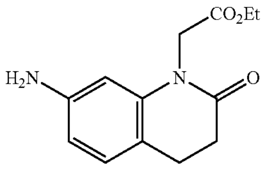 | ES: 249 |
| 351 | 174 | 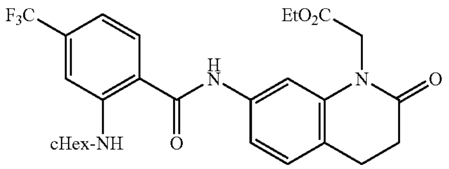 | F: 518 |
| 352 | 9 | 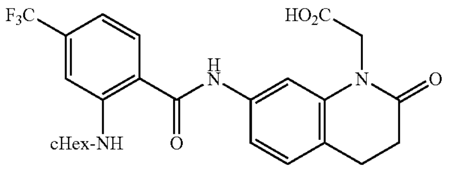 | ES: 490 |
| 353 | 159 | 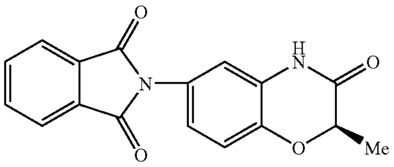 | FN: 308 |
| 354 | 160 | 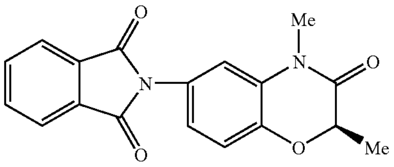 | F: 323 |
| 355 | 161 | 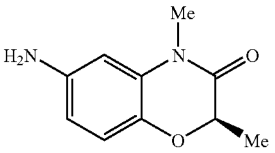 | ES: 193 |
| 356 | 159 | 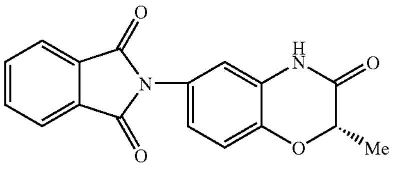 | FN: 308 |
| 357 | 160 | 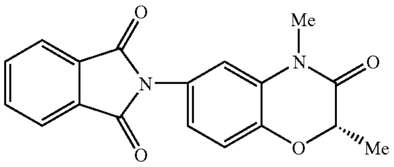 | F: 323 |

TABLE 18-continued
| | | | |
|---|---|---|---|
| 358 | 161 | 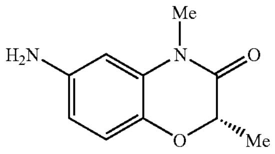 | F: 193 |
| 359 | 359 | 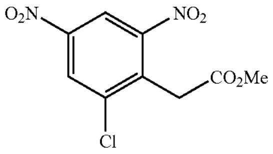 | AN: 259 |
| 360 | 360 | 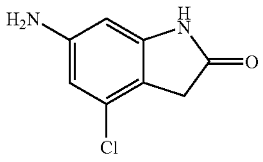 | FN: 181 |
TABLE 19
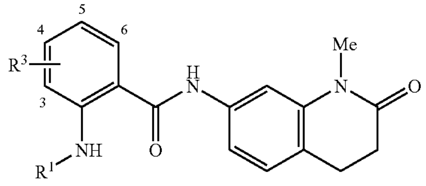
| Ex | Syn | $R^3$ | $R^1$ | Sal | Dat |
|---|---|---|---|---|---|
| 1 | 1 | 4-Cl | cPen | HCl | ES: 398, NMR: 10.13 (1H, s), 7.40 (1H, s), 3.23 (3H, s), 2.02-1.98 (2H, m) |
| 2 | 2 | 4-Cl | 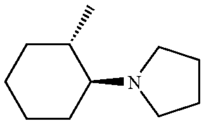 | HCl | F: 481, NMR: 10.33 (1H, s), 6.75 (1H, dd), 2.85-2.81 (2H, m), 2.11-2.09 (1H, m). |
| 3 | 3 | 4-Cl | $MeS(O)_2—C_2H_4—$ | | ESN: 434, NMR: 10.15 (1H, s), 6.74 (1H, dd), 3.43 (2H, t), 2.84-2.81 (2H, m). |
| 4 | 4 | 4-Cl | 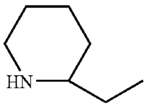 | HCl | ES: 427, NMR: 10.23 (1H, s), 3.23 (3H, s), 2.93-2.78 (3H, m). |
| 5 | 5 | 4-Cl | 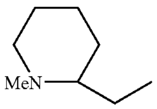 | HCl | ES: 441, NMR: 10.23 (1H, s), 3.81-3.71 (1H, m), 3.23 (3H, s). |
| 6 | 1 | 4-Cl | cHex | | F: 412, NMR: 10.09 (1H, s), 6.77 (1H, s), 3.24 (3H, s), 3.47-3.37 (1H, m), 2.87-2.78 (2H, m), 1.95-1.15 (10H, m). |
| 7 | 1 | $4-CF_3$ | cPen | | F: 432, NMR: 10.29 (1H, s), 3.95-3.86 (1H, m), 3.24 (3H, s), 2.88-2.79 (2H, m), 2.07-1.37 (8H, m). |
| 8 | 1 | $4-CF_3$ | cHex | | F: 446, NMR: 10.28 (1H, s), 3.56-3.45 (1H, m), 3.24 (3H, s), 1.97-1.18 (10H, m). |
| 9 | 1 | $5-CF_3$ | cHex | | F: 446, NMR: 10.28 (1H, s), 6.92 (1H, d), 2.86-2.82 (2H, m), 1.97-1.20 (10H, m). |

TABLE 19-continued

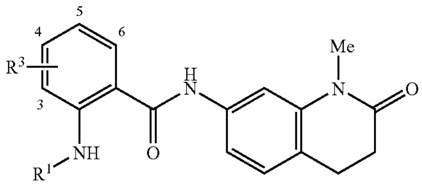

| Ex | Syn | $R^3$ | $R^1$ | Sal | Dat |
|---|---|---|---|---|---|
| 10 | 1 | 4- 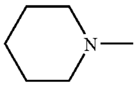 | cHex | HCl | F: 461, NMR: 10.19 (1H, s), 3.55-3.38 (5H, m), 3.24 (3H, s), 2.86-2.80 (2H, m), 2.03-1.19 (16H, m). |
| 11 | 1 | H | cHex | | F: 378, EA: $C_{23}H_{27}N_3O_2$, Calcd C, 73.18; 14, 7.21; N, 11.13. Found C, 73.16;H, 7.26; N, 11.12. |
| 12 | 1 | 4-Cl | 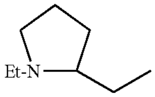 | HCl | F: 441, NMR: 10.24 (1H, s), 6.76 (1H, dd), 2.85-2.81 (2H, m), 1.18 (3H, t). |
| 13 | 1 | 4-Cl | 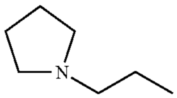 | 2HCl | ES: 427, NMR: 10.24 (1H, s), 6.74 (1H, dd), 2.84-2.81 (2H, m), 2.04-1.81 (4H, m). |
| 14 | 1 | 4-Cl | 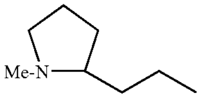 | 2HCl | F: 441, NMR: 10.20 (1H, s), 6.69 (1H, dd), 2.84-2.81 (2H, m), 2.33-1.66 (6H, m). |

TABLE 20

| | | | | | |
|---|---|---|---|---|---|
| 15 | 1 | 4-Cl | MeO—$C_2H_4$— | | F: 388, EA: $C_{20}H_{22}ClN_3O_3$, Calcd C, 61.93; H, 5.72; N, 10.83; Cl, 9.14. Found C, 61.75; H, 5.76; N, 10.80; Cl, 9.06. |
| 16 | 1 | 4-Cl | 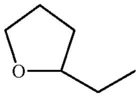 | | F: 414, EA: $C_{22}H_{24}ClN_3O_3$, Calcd C, 63.84;H, 5.84; N, 10.15; Cl, 8.57. Found C, 63.78; H, 5.82; N, 10.08; Cl, 8.46. |
| 17 | 1 | 4-Cl | $Et_2CH$— | | F: 400, EA: $C_{22}H_{26}ClN_3O_2$, Calcd C, 66.07; H, 6.55; N, 10.51; Cl, 8.87. Found C, 66.05; H, 6.57; N, 10.55; Cl, 8.60. |
| 18 | 1 | 4-Cl | $Me_2CH$—$CH_2$— | | F: 386, NMR, 10.11 (1H, s), 3.23 (3H, s), 1.92-1.80 (1H, m). |
| 19 | 1 | 4-Cl | 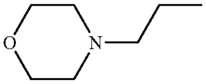 | 2HCl | F: 443, NMR: 10.26 (1H, s), 2.87-2.78 (2H, m). |
| 20 | 1 | 4-Cl | 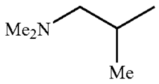 | HCl | F: 415, NMR: 10.28 (1H, s), 3.23 (3H, s), 1.19 (3H, d). |
| 21 | 1 | 4-Cl | 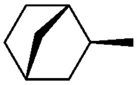 | | F: 424, EA: $C_{24}H_{26}ClN_3O_2$, Calcd C, 68.00; H, 6.18; N, 9.91; Cl, 8.36. Found C, 67.92; H, 6.24; N, 9.93; Cl, 8.40. |
| 22 | 1 | 4-Cl | 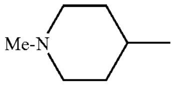 | 2HCl | F: 427, NMR: 10.25-10.18 (1H, m), 3.73-3.62 (1H, m), 3.24 (3H, s). |

TABLE 20-continued

| | | | | | |
|---|---|---|---|---|---|
| 23 | 1 | 4-Cl | 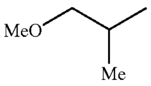 | | F: 402, NMR: 10.10 (1H, s), 7.16( 1H, d), 3.37 (2H, d). |
| 24 | 1 | 4-Cl | 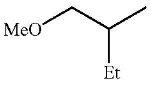 | | F: 416, EA: $C_{22}H_{26}ClN_3O_3$, Calcd C, 63.53; H, 6.30; N, 10.1; Cl, 8.52. Found C, 63.53; H, 6.31; N, 10.11; Cl, 8.55. |
| 25 | 2 | H | Me | | F: 310, EA: $C_{18}H_{19}N_3O_2$, Calcd C, 69.88; H, 6.19; N, 13.58. Found C, 69.83;H, 6.24; N, 13.56. |
| 26 | 2 | 4-Ph | cHex | | F: 454, NMR: 10.08 (1H, s), 7.80 (1H, d), 7.72-7.68 (3H, m), 2.85-2.81 (2H, m). |
| 27 | 2 | 4-Cl | EtO—$C_2H_4$— | | F: 402, EA: $C_{21}H_{24}ClN_3O_3$, Calcd C, 62.76; H, 6.02; N, 10.46; Cl, 8.82. Found C, 62.69; H, 6.04; N, 10.44; Cl, 8.87. |
| 28 | 2 | 4-Cl | MeO—$C_3H_6$— | | F: 402, EA: $C_{21}H_{24}ClN_3O_3$, Calcd C, 62.76; H, 6.02; N, 10.46; Cl, 8.82. Found C, 62.60; H, 6.03; N, 10.46; Cl, 8.82. |
| 29 | 2 | 4-Cl | 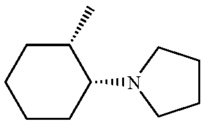 | HCl | F: 481:, NMR: 10.33 (1H, s), 6.78 (1H, dd), 2.85-2.82 (2H, m), 2.09-2.07 (1H, m). |
| 30 | 2 | 4-Cl | cPr | | F: 370, EA: $C_{20}H_{20}ClN_3O_2$, Calcd C, 64.95; H, 5.45; N, 11.36; Cl, 9.59. Found C, 65.05; H, 5.52; N, 11.22; Cl, 9.43. |
| 31 | 2 | 4-Cl | 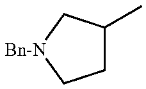 | 2HCl | F: 489, NMR: 10.27-10.23 (1H, m), 6.80-6.75 (2H, m), 2.85-2.80 (2H, m), 2.03-1.80 (1H, m). |

TABLE 21

| | | | | | |
|---|---|---|---|---|---|
| 32 | 2 | 4-Cl | 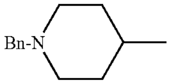 | 2HCl | F: 503, NMR: 10.20-10.17 (1H, m), 6.71-6.67 (1H, m), 3.08-3.00 (2H, m), 2.86-2.80 (2H, m). |
| 33 | 2 | 4-Cl | $iPr_2N$—$C_2H_4$— | 2HCl | F: 457, NMR: 10.23 (1H, s), 6.74 (1H, dd), 2.85-2.81 (2H, m), 1.32 (6H, d), 1.28 (6H, d). |
| 34 | 2 | 4-$CF_3$ | MeO—$C_2H_4$— | | F: 422, EA: $C_{21}H_{22}F_3N_3O_3$, Calcd C, 59.85, H, 5.26; N, 9.97; F, 13.52. Found C, 59.82; H, 5.36; N, 10.03; F, 13.68. |
| 35 | 2 | 4-Cl | 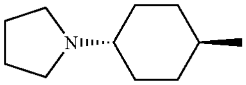 | 2HCl | F: 481, NMR: 10.17 (1H, s), 6.65 (1H, dd), 2.84-2.81 (2H, m), 1.76-1.67 (2H, m). |
| 36 | 2 | H | Ph | | F: 372, EA: $C_{23}H_{21}N_3O_2$, Calcd C, 74.37; H, 5.70; N, 11.31. Found C, 74.39;H, 5.69; N, 11.33. |
| 37 | 2 | 4-Cl | 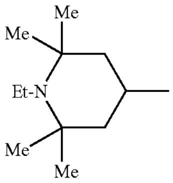 | 2HCl | F: 497, NMR: 10.22 (1H, s), 6.72 (1H, dd), 2.85-2.81 (2H, m), 2.09-1.92 (4H, m). |
| 38 | 2 | 4-Cl | 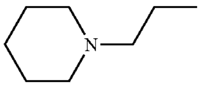 | HCl | F: 441, NMR: 10.24 (1H, s), 6.74 (1H, dd), 2.85-2.81 (2H, m), 1.81-1.68 (5H, m), 1.44-1.32 (1H, m). |
| 39 | 2 | 4-Cl | $Et_2N$—$C_2H_4$— | HCl | F: 429, NMR: 10.23 (1H, s), 6.74 (1H, dd), 2.84-2.81 (2H, m), 1.21 (6H, t). |
| 40 | 2 | 4-Cl | MeS—$C_2H_4$— | | F: 404, EA: $C_{20}H_{22}ClN_3O_2S$, Calcd C, 59.47; H, 5.49; N, 10.40; S, 7.94; Cl, 8.78. Found C, 59.34; H, 5.53; N, 10.39; |

TABLE 21-continued

| | | | | | |
|---|---|---|---|---|---|
| | | | | | S, 7.94; Cl, 8.80. |
| 41 | 2 | 5-Cl | cHex | | F: 412, EA: $C_{23}H_{26}ClN_3O_2$, Calcd C, 67.06; H, 6.36; N, 10.20; Cl, 8.61. Found C, 67.02; H, 6.42; N, 1023; Cl, 8.64. |
| 42 | 2 | 4-$CF_3$ | 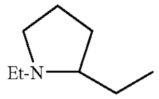 | HCl | F: 475, EA: $C_{25}H_{29}F_3N_4O_2$•HCl, Calcd C, 58.76; H, 5.92; N, 10.96; Cl, 6.94; F, 11.15. Found C, 58.58; H, 5.94; N, 10.89; Cl, 7.00; F, 11.27. |
| 43 | 2 | 4-$CF_3$ | 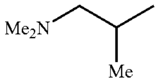 | HCl | F: 449, NMR: 10.46 (1H, s), 7.04-7.02 (1H, m), 2.56-2.52 (2H, m), 1.19 (3H, d). |
| 44 | 2 | 5-Me | cHex | | F: 392, EA: $C_{24}H_{29}N_3O_2$, Calcd C, 73.63; H, 7.47; N, 10.73. Found C, 73.41; H, 7.50; N, 10.39. |
| 45 | 2 | 6-Cl | cHex | | F: 412, EA: $C_{23}H_{26}ClN_3O_2$, Calcd C, 67.06; H, 6.36; N, 10.20; Cl, 8.61. Found C, 67.01;H, 6.35; N, 10.04; Cl, 8.60. |
| 46 | 2 | H | Bn | | F: 386, NMR: 10.11 (1H, s), 6.68-6.62 (2H, m), 4.42 (2H, d), 2.84-2.81 (2H, m). |
| 47 | 2 | 4-Cl | 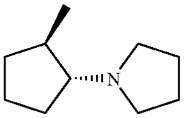 | HCl | F: 467, NMR: 10.22 (1H, s), 6.75 (1H, dd), 2.84-2.81 (2H, m), 2.27-1.41 (10H, m). |

TABLE 22

| | | | | | |
|---|---|---|---|---|---|
| 48 | 2 | 4-Cl | 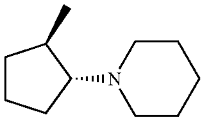 | HCl | F: 481, NMR: 10.22 (1H, s), 6.76 (1H, dd), 2.85-2.81 (2H, m), 2.19-1.34 (12H, m). |
| 49 | 2 | 4-Cl | 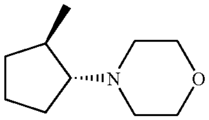 | HCl | F: 483, NMR: 10.22 (1H, s), 6.76 (1H, dd), 2.85-2.81 (2H, m), 2.22-1.43 (6H, m). |
| 50 | 2 | 4-Cl | 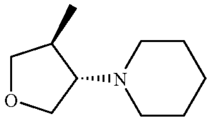 | HCl | ES: 483, NMR: 10.26 (1H, s), 6.79 (1H, dd), 2.85-2.81 (2H, m), 1.87-1.34 (6H, m). |
| 51 | 2 | 4-Cl | 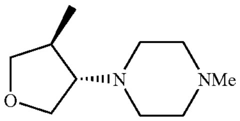 | 2HCl | ES: 498, NMR: 10.24 (1H, s), 6.77 (1H, dd), 2.85-2.81 (2H, m), 2.79 (3H, s). |
| 52 | 2 | 4-Cl | 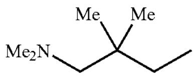 | HCl | F: 443, NMR: 10.21 (1H, s), 6.69 (1H, dd), 2.56-2.52 (2H, m), 1.13 (6H, s). |
| 53 | 2 | 4-Cl | 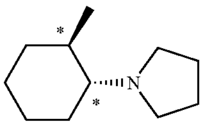 | HCl | F: 481, NMR: 10.34 (1H, s), 6.75 (1H, dd), 2.85-2.81 (2H, m), 2.15-1.23 (12H, m). |
| 54 | 2 | 4-Cl | 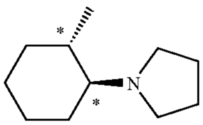 | HCl | F: 481, NMR: 10.31 (1H, s), 6.76 (1H, dd), 2.85-2.81 (2H, m), 2.13-1.23 (12H, m). |

TABLE 22-continued

| | | | | | |
|---|---|---|---|---|---|
| 55 | 2 | 4-Cl | 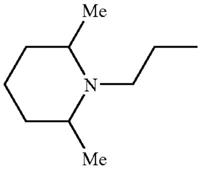 | 2HCl | F: 469, NMR: 10.26 (1H, s), 7.74-7.72 (1H, m), 2.84-2.81 (2H, m), 1.84-1.44 (6H, m). |
| 56 | 2 | 4-Cl | 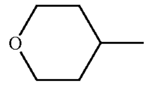 | | F: 414, NMR: 10.12 (1H, s), 6.66 (1H, dd), 3.86-3.80 (2H, m), 3.52-3.45 (2H, m), 2.84-2.81 (2H, m). |
| 57 | 2 | 4-Cl | 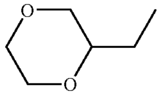 | | ES: 430, EA: $C_{22}H_{24}ClN_3O_4$, Calcd C, 61.46,H, 5.63; N, 9.77; Cl, 8.25. Found C, 61.34; H, 5.62; N, 9.76; Cl, 8.23. |
| 58 | 2 | 4-Cl | 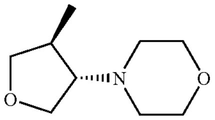 | HCl | F: 485, NMR: 10.26 (1H, s), 6.79 (1H, dd), 4.28-4.24 (1H, m), 2.85-2.81 (2H, m). |
| 59 | 2 | 4-Cl | $Et_2N—C_3H_6—$ | HCl | ES: 443, NMR: 10.18 (1H, s), 6.69 (1H, dd), 2.84-2.81 (2H, m), 1.20 (6H, t). |
| 60 | 2 | 4-Cl | 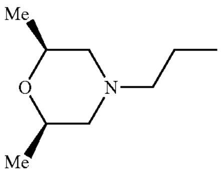 | HCl | F: 471, NMR: 10.23 (1H, s), 6.75 (1H, dd), 2.85-2.81 (2H, m), 1.12 (6H, d). |
| 61 | 2 | 4-Cl | 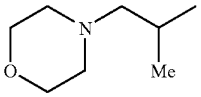 | HCl | ES 457, NMR: 10.25 (1H, s), 6.77 (1H, m), 2.85-2.81 (2H, m), 1.20 (3H, d). |
| 62 | 2 | 5- 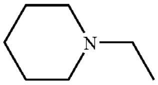 | cHex | 2HCl | F: 475, EA: $C_{29}H_{38}N_4O_2$•2HCl, Calcd C, 63.61; H, 7.36; N, 10.23; Cl, 12.95. Found C, 63.45; H, 7.38; N, 10.13; Cl, 13.05. |

TABLE 23

| | | | | | |
|---|---|---|---|---|---|
| 63 | 2 | 4-Cl | 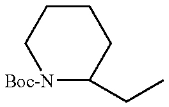 | | F: 527, EA: $C_{28}H_{35}ClN_4O_4$, Calcd C, 63.81; H, 6.69; N, 10.63; Cl, 6.73. Found C, 63.77; H, 6.59; N, 10.58; Cl, 6.70. |
| 64 | 2 | H | 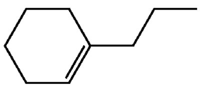 | | F: 404, NMR: 10.04 (1H, s), 7.16 (1H, d), 5.50 (1H, m), 2.84-2.80 (2H, m). |
| 65 | 2 | $4-CF_3$ | 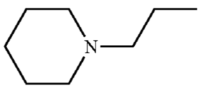 | HCl | F: 475, NMR: 10.41 (1H, s), 3.24 (3H, s), 2.99-2.80 (4H, m). |
| 66 | 2 | $4-CF_3$ | $Et_2N—C_2H_4—$ | HCl | F: 463, EA, $C_{24}H_{29}F_3N_4O_2$•HCl, Calcd C, 57.77; H, 6.06; N, 11.23; Cl, 7.11; F, 11.42. Found C, 57.53; H, 5.98; N, 11.16; Cl, 7.08; F, 11.58. |
| 67 | 2 | 4-Cl | $Et_2N—C_4H_8—$ | HCl | F: 457, NMR: 10.19 (1H, s), 3.24 (3H, s), 1.20 (6H, t). |

TABLE 23-continued

| | | | | | |
|---|---|---|---|---|---|
| 68 | 2 | 4-Cl | 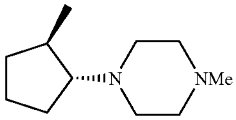 | 2HCl | F: 496, NMR: 10.24 (1H, s), 4.40-4.24 (1H, m), 3.24 (3H, s), 2.86-2.76 (5H, m), 2.57-2.52 (2H, m). |
| 69 | 2 | 4-Cl | 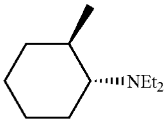 | HCl | F: 483, NMR: 10.37 (1H, s), 4.11-3.98 (1H, m), 3.58-3.48 (1H, m), 3.23 (3H, s). |
| 70 | 2 | 4-Cl | cHep | | F: 426, EA: $C_{24}H_{28}ClN_3O_2$, Calcd C, 67.67; H, 6.63; N, 9.87; Cl, 8.32. Found C, 67.61;H, 6.68; N, 9.91; Cl, 8.26. |
| 71 | 2 | 4-Cl | 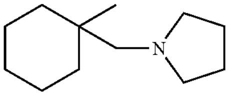 | HBr | F: 495, EA: $C_{28}H_{35}ClN_4O_2$•HBr, Calcd C, 58.39; H, 6.30; N, 9.73; Cl, 6.16. Found C, 58.24; H, 6.30; N, 9.68; Cl, 6.24. |
| 72 | 3 | 4-Cl | MeS(O)—$C_2H_4$— | | F: 420, NMR: 10.15 (1H, s), 6.72 (1H, dd), 3.14-3.07 (1H, m), 2.93-2.89 (1H, m), 2.84-2.81 (2H, m). |

TABLE 24

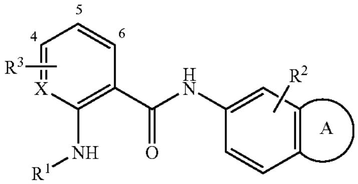

| Ex | Syn | $R^3$ | X | $R^1$ | 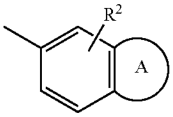 | Sal | Dat |
|---|---|---|---|---|---|---|---|
| 73 | 1 | 4-$CF_3$ | CH | cHex | 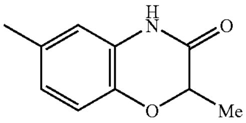 | | F: 448, EA: $C_{23}H_{24}F_3N_3O_3$, Calcd C, 61.74; H, 5.41; N, 9.39; Cl, 12.74. Found C, 61.59;H, 5.49; N, 9.35; Cl, 12.95. |
| 74 | 1 | 4-Cl | CH | iBu | 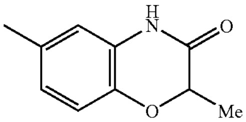 | | F: 388, EA: $C_{20}H_{22}ClN_3O_3$, Calcd C, 61.93; H, 5.72; N, 10.83; Cl, 9.14. Found C, 61.80; H, 5.76; N, 10.75; Cl, 9.06. |
| 75 | 1 | 4-Cl | CH | 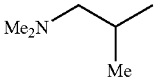 | 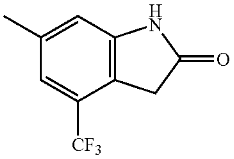 | | F: 455, NMR: 10.74 (1H, s), 10.29 (1H, s), 3.72-3.63 (1H, m), 1.13 (3H, d). |
| 76 | 1 | 4-Cl | CH | 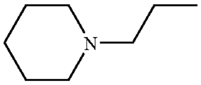 | 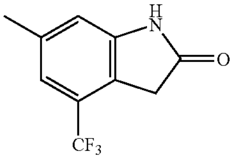 | | F: 481, EA: $C_{23}H_{24}ClF_3N_4O_2$, Calcd C, 57.44; H, 5.03; N, 11.65; Cl, 7.37; F, 11.85. Found C, 57.29; H, 5.00; N, 11.55; Cl, 7.32; F, 11.89. |

TABLE 24-continued

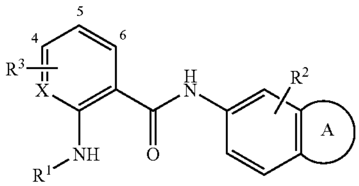

| Ex | Syn | $R^3$ | X | $R^1$ | 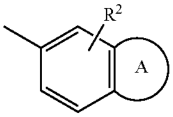 | Sal | Dat |
|---|---|---|---|---|---|---|---|
| 77 | 1 | 4-Cl | CH | $Et_2N—C_2H_4—$ | 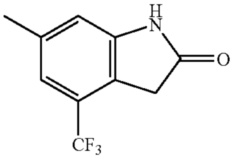 | | F: 469, EA: $C_{22}H_{24}ClF_3N_4O_2$, Calcd C, 56.35; H, 5.16; N, 11.95; Cl, 7.56; F, 12.16. Found C, 56.34; H, 5.10; N, 11.92; Cl, 7.50; F, 12.25. |
| 78 | 2 | 4-Cl | CH | 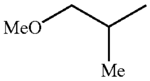 | 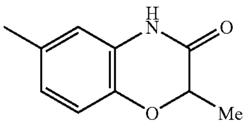 | | F: 404, EA: $C_{20}H_{22}ClN_3O_4$, Calcd C, 59.48; H, 5.49; N, 10.40; Cl, 8.78. Found C, 59.20; H, 5.58; N, 10.36; Cl, 8.72. |
| 79 | 2 | $4-CF_3$ | CH | $MeO—C_2H_4—$ | 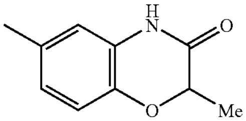 | | F: 424, EA: $C_{20}H_{20}F_3N_3O_4$, Calcd C, 57.74; H, 4.76; N, 9.92; Cl, 13.46. Found C, 56.51; H, 4.80; N, 9.85; Cl, 13.57. |
| 80 | 2 | 4-Cl | CH | $MeO—C_3H_6—$ | 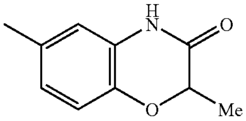 | | F: 404, EA: $C_{20}H_{22}ClN_3O_4$, Calcd C, 59.48; H, 5.49; N, 10.40; Cl, 8.78. Found C, 59.38; H, 5.41; N, 10.39; Cl, 8.78. |
| 81 | 2 | 4-Cl | CH | cHex | 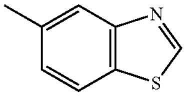 | | F: 386, EA: $C_{20}H_{20}ClN_3OS$, Calcd C, 62.25;H, 5.22; N, 10.89; S, 8.31; Cl, 9.19. Found C, 62.10; H, 5.27; N, 10.82; S, 8.27; Cl, 9.18. |

TABLE 25

| | | | | | | |
|---|---|---|---|---|---|---|
| 82 | 2 | H | N | iPr | 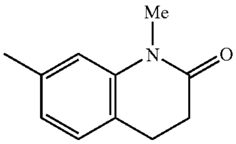 | F: 339, NMR: 10.16 (1H, s), 4.28-4.18 (1H, m), 3.24 (3H, s). |
| 83 | 2 | H | N | cHex | 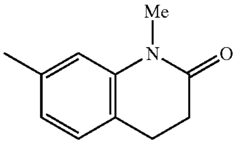 | F: 379, NMR: 10.15 (1H, s), 4.03-3.92 (1H, m), 3.24 (3H, s). |
| 84 | 2 | 4-Cl | CH | cHep | 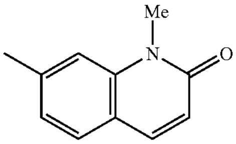 | F: 424, EA: $C_{24}H_{26}ClN_3O_2$, Calcd C, 68.00; H, 6.18; N, 9.91; Cl, 8.36. Found C, 68.05; H, 6.17; N, 9.96; Cl, 8.27. |

TABLE 25-continued

| | | | | | | | |
|---|---|---|---|---|---|---|---|
| 85 | 2 | 4-Cl | CH | cHex | 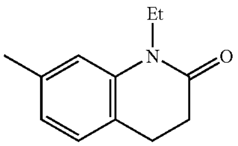 | | F: 426, EA: $C_{24}H_{28}ClN_3O_2$, Calcd C, 67.67; H, 6.63; N, 9.87; Cl, 8.32. Found C, 67.49; H, 6.70; N, 9.85; Cl, 8.22. |
| 86 | 2 | 4-Cl | CH | cHex | 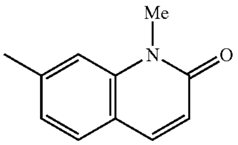 | | F: 410, NMR: 10.39 (1H, s), 6.65 (1H, dd), 6.51 (1H, d), 3.59 (3H, s), 3.50-3.39 (1H, m). |
| 87 | 2 | 4-Cl | CH | cHex | 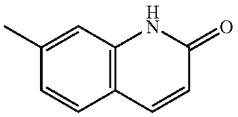 | | F: 398, EA: $C_{22}H_{24}ClN_3O_2$, Calcd C, 66.41; H, 6.08; N, 10.56; Cl, 8.91. Found C, 66.06; H, 6.08; N, 10.49; Cl, 8.96. |
| 88 | 2 | 4-Cl | CH | cHex | 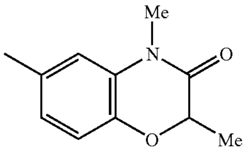 | | ES: 428, EA: $C_{23}H_{26}ClN_3O_3$, Calcd C, 64.55; H, 6.12; N, 9.82; Cl, 8.28. Found C, 64.44; H, 6.13; N, 9.79; Cl, 8.29. |
| 89 | 2 | 4-Cl | CH | cHex | 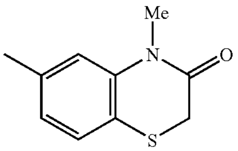 | | ES: 430, EA: $C_{22}H_{24}ClN_3O_2S$, Calcd C, 61.46; H, 5.63; N, 9.77; S, 7.46; Cl, 8.25. Found C, 61.27; H, 5.65; N, 9.70; S, 7.43; Cl, 8.21. |
| 90 | 2 | 4-Cl | CH | cHex | 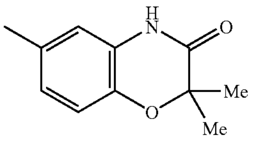 | | F: 428, NMR: 10.62 (1H, s), 10.06 (1H, s), 3.48-3.36 (1H, m), 1.39 (6H, s). |
| 91 | 2 | 4-$CF_3$ | N | cHex | 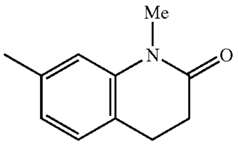 | | F: 447, EA: $C_{23}H_{25}F_3N_4O_2$, Calcd C, 61.87; H, 5.64; N, 12.55, Cl, 12.77. Found C, 61.76; H, 5.63; N, 12.53; Cl, 12.91. |
| 92 | 2 | 4-Cl | CH | 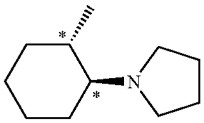 | 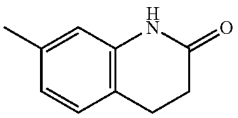 | HCl | F: 467, NMR: 10.26 (1H, s), 10.15 (1H, s), 4.04-3.91 (1H, m), 2.85-2.81 (2H, m), 2.45-2.41 (2H, m). |
| 93 | 2 | 4-Cl | CH | 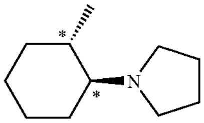 | 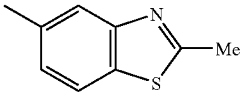 | 2HCl | F: 469, NMR: 10.46 (1H, s), 4.03-3.91 (1H, m), 2.79 (3H, s), 2.14-1.97 (2H, m). |
| 94 | 2 | 4-Cl | CH | 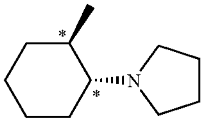 | 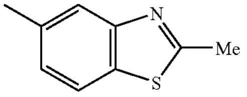 | 2HCl | F: 469, NMR: 10.54 (1H, s), 4.05-3.94 (1H, m), 2.80 (3H, s), 2.17-1.98 (2H, m). |

TABLE 26
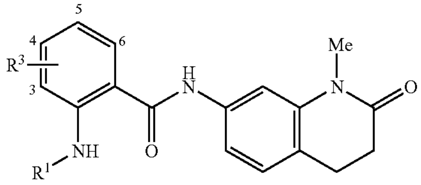
| Ex | Syn | $R^3$ | $R^1$ | Sal | Dat |
|---|---|---|---|---|---|
| 95 | 95 | 4-Cl | 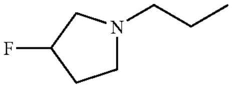 | HCl | F: 445, NMR: 10.26 (1H, s), 7.41 (1H, dd), 6.94 (1H, d), 6.73 (1H, dd), 5.56-5.36 (1H, m), 3.23 (3H, s), 2.83 (2H, t). |
| 96 | 96 | 4-$CF_3$ | 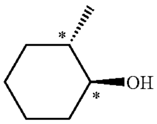 | | F: 462, NMR: 7.82 (1H, d), 7.66 (1H, d), 4.85 (1H, d), 2.84 (2H, t) |
| 97 | 97 | 4-$CF_3$ | 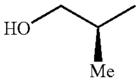 | | F: 422, NMR: 10.38 (1H, s), 7.40 (1H, dd), 4.90 (1H, t), 2.85-2.82 (2H, m) |
| 98 | 98 | 4-tBu | 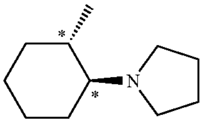 | Fum | F: 503, NMR: 10.00 (1H, s), 7.80-7.56 (2H, m), 7.45-7.38 (1H, m), 3.23 (3H, s), 2.11-2.01 (1H, m), 1.28 (9H, s). |
| 99 | 99 | 4-Cl | 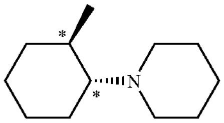 | HCl | F: 495, NMR: 10.38 (1H, s), 7.69 (1H, d), 7.39 (1H, dd), 6.80 (1H, dd), 4.03-3.92 (1H, m), 3.23 (3H, s), 3.03-2.90 (1H, m). |
| 100 | 100 | 4-$CF_3$ | 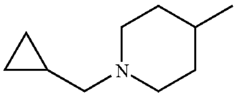 | HCl | F: 501, NMR: 10.64 (1H, s), 7.41 (1H, dd), 0.67-0.59 (2H, m), 0.43-0.38 (2H, m) |
| 101 | 101 | 4-$CF_3$ | 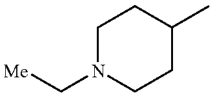 | HCl | F: 475, NMR: 10.28 (1H, s), 7.40 (1H, dd), 2.86-2.82 (2H, m), 1.26 (3H, t) |
| 102 | 102 | 4- 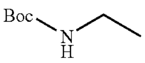 | cHex | | F: 507, NMR: 9.96 (1H, s), 7.15 (1H, d), 6.46 (1H, d), 4.07 (2H, d), 3.23 (3H, s), 1.99-1.89 (2H, m). |
| 103 | 103 | H | 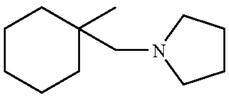 | 2HBr | F: 461, NMR: 10.27 (1H, s), 7.72 (1H, d), 7.19 (1H, d), 3.68-3.54 (4H, m), 3.23 (3H, s), 2.84 (2H, t). |
| 104 | 104 | 4-$CF_3$ | 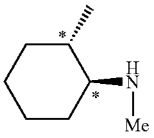 | HCl | F: 475, NMR: 10.44 (1H, s), 7.86 (1H, d), 7.28-7.17 (3H, m), 3.85-3.73 (1H, m), 3.23 (3H, s), 2.18-2.08 (1H, m). |
| 115 | 1 | 4-Cl | 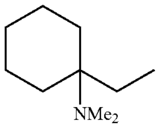 | HCl | F: 469, NMR: 10.25 (1H, s), 9.42 (1H, s), 7.93 (1H, br), 7.79 (1H, d), 7.42-7.35 (2H, m), 6.78 (1H, d), 1.98-1.86 (2H, m), 1.80-1.68 (3H, m). |

TABLE 26-continued
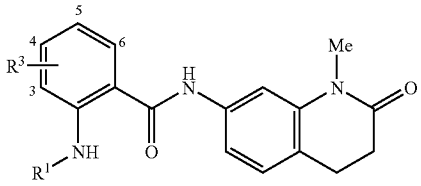
| Ex | Syn | $R^3$ | $R^1$ | Sal | Dat |
|---|---|---|---|---|---|
| 116 | 1 | 4-Cl | tBu | | F: 386, NMR: 10.15 (1H, s), 7.85 (1H, s), 7.69 (1H, d), 7.16 (1H, d), 6.85 (1H, d), 3.23 (3H, s), 2.83 (2H, t), 1.36 (9H, s). |
TABLE 27
| | | | | | |
|---|---|---|---|---|---|
| 117 | 1 | 4-Cl | 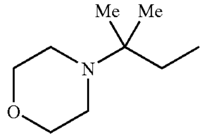 | HCl | ES: 471, NMR: 10.26 (1H, s), 7.77 (1H, d), 7.17 (1H, d), 6.75 (1H, dd), 4.00-3.93 (4H, m), 2.83 (2H, t), 1.40 (6H, s). |
| 118 | 1 | 4-Cl | 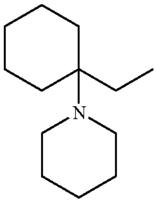 | HCl | ES: 509, NMR: 10.26 (1H, s), 9.31 (1H, s), 7.82 (1H, d), 7.18 (1H d), 6.78 (1H, dd), 3.23 (3H, s), 1.95-1.56 (10H, m). |
| 119 | 1 | 4-Cl | 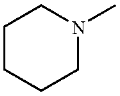 | HCl | F: 413, NMR: 10.21 (1H, s), 7.72 (1H, d), 7.16 (1H, d), 3.24 (3H, s), 1.64 (4H, t). |
| 120 | 1 | 4-Cl | 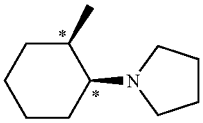 | | F: 481, NMR: 10.07 (1H, s), 7.95 (1H, d), 7.68 (1H, d), 7.17 (1H, d), 6.61 (1H, d), 3.23 (3H, s), 1.93-1.80 (2H, m). |
| 121 | 1 | 4-Cl | 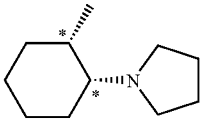 | | ES: 481, NMR: 10.07 (1H, s), 7.95 (1H, d), 7.68 (1H, d), 7.17 (1H, d), 6.61 (1H, d), 3.23 (3H, s), 1.93-1.80 (2H, m). |
| 122 | 2 | 3- 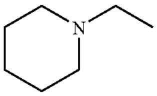 | cHex | 2HCl | F: 475, NMR: 10.57 (1H, s), 7.84 (1H, d), 4.33 (2H, s), 3.23 (3H, s), 2.89-2.77 (3H, m). |
| 123 | 2 | 4-Br | 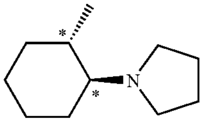 | HCl | ES: 525, NMR: 10.32 (1H, s), 7.65 (1H, d), 7.17 (1H, d), 6.89 (1H, dd), 4.03-3.90 (1H, m), 3.23 (3H, s), 2.83 (2H, t). |
| 124 | 2 | 4-CN | cHex | | F: 403, EA: $C_{24}H_{26}N_4O_2$, Calcd C, 71.62; H, 6.51; N, 13.92. Found C, 71.50; H, 6.52; N, 13.81. |
| 125 | 2 | 4-Cl | 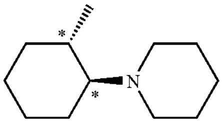 | HCl | F: 495, NMR: 10.39 (1H, s), 7.69 (1H, d), 7.39 (1H, dd), 6.80 (1H, dd), 4.03-3.92 (1H, m), 3.23 (3H, s), 3.03-2.89 (1H, m). |

TABLE 27-continued
| | | | | | |
|---|---|---|---|---|---|
| 126 | 2 | 4-$CF_3$ | 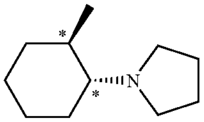 | HCl | F: 515, NMR: 10.55 (1H, s), 7.47 (1H, dd), 2.85-2.82 (2H, m), 2.56-2.52 (2H, m) |
| 127 | 2 | 4-$NO_2$ | 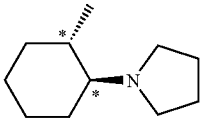 | HCl | ES: 492, NMR: 10.60 (1H, s), 7.89 (1H, d), 7.73 (1H, d), 4.11-3.99 (1H, m), 3.24 (3H, s), 2.84 (2H, t). |
| 128 | 2 | 4-Cl | 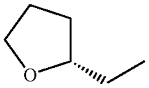 | | F: 414, NMR: 10.12 (1H, s), 6.66 (1H, dd), 2.84-2.81 (2H, m), 2.55-2.52 (2H, m) |
| 129 | 2 | 4-Cl | 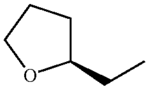 | | F: 414, NMR: 10.12 (1H, s), 6.66 (1H, dd), 2.84-2.81 (2H, m), 2.55-2.52 (2H, m) |
| 130 | 2 | 4-$CF_3$ | 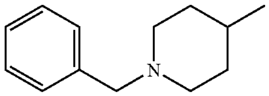 | HCl | ES: 537, NMR: 10.36 (1H, s), 7.39 (1H, dd), 4.28 (2H, d), 2.87-2.81 (2H, m), 2.57-2.52 (2H, m) |
TABLE 28
| | | | | | |
|---|---|---|---|---|---|
| 131 | 2 | 4-CN | 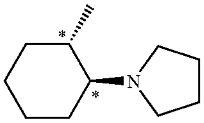 | HCl | F: 472, NMR: 10.51 (1H, s), 7.81 (1H, d), 7.23-7.12 (3H, m) 4.07-3.95 (1H, m), 2.84 (2H, t). |
| 132 | 2 | 4-$CF_3$ | 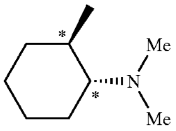 | HCl | F: 489, NMR: 10.59 (1H, s), 7.48 (1H, dd), 2.85-2.82 (2H, m), 2.74 (3H, d) |
| 133 | 2 | 4-Cl | 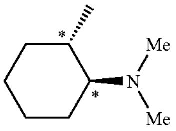 | HCl | F: 455, NMR: 10.38 (1H, s), 1H, dd), 2.84-2.81 (2H, m), 2.73 (3H, d) |
| 134 | 2 | 4-Cl | 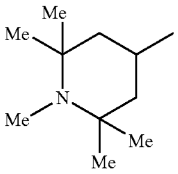 | HCl | ESN: 481, NMR: 10.20 (1H, s), 7.40 (1H, dd), 2.85-2.81 (2H, m), 2.69 (3H, d) |
| 135 | 2 | 4-$CF_3$ | 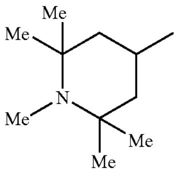 | HCl | F: 517, NMR: 10.38 (1H, s), 7.41 (1H, dd), 2.86-2.82 (2H, m), 2.70 (3H, d) |

TABLE 28-continued
| | | | | | |
|---|---|---|---|---|---|
| 136 | 2 | 4-$CF_3$ | 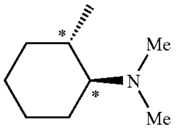 | HCl | F: 489, NMR: 10.60 (1H, s), 7.48 (1H, dd), 2.85-2.82 (2H, m), 2.74 (3H, d) |
| 137 | 2 | 4-$CF_3$ | 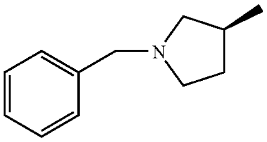 | | F: 523, NMR: 10.32 (1H, s), 7.42 (1H, dd), 3.65-3.57 (2H, m), 2.86-2.82 (2H, m) |
| 138 | 2 | 4-Cl | 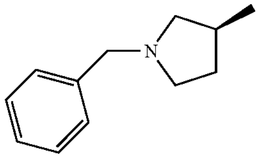 | | ES: 489, NMR: 10.13 (1H, s), 7.18 (1H, d), 3.65-3.57 (2H, m), 2.85-2.82 (3H, m) |
| 139 | 2 | 4-Cl | 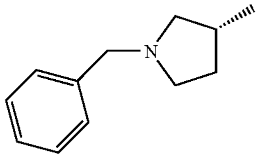 | | ES: 489, NMR: 10.13 (1H, s), 7.18 (1H, d), 3.64-3.56 (2H, m), 2.85-2.81 (3H, m) |
| 140 | 2 | 4-Cl | 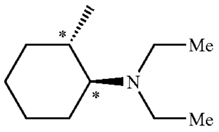 | | F: 483, NMR: 10.04 (1H, s), 7.80 (1H, d), 7.60 (1H, d), 7.15 (1H, s), 3.22 (3H, s), 2.82 (2H, t). |
| 141 | 2 | 4-$CF_3$ | 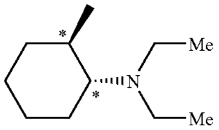 | | F: 517, NMR: 10.24 (1H, s), 7.74 (1H, d), 3.23 (3H, s), 2.83 (2H, t), 1.86-1.59 (2H, m). |
| 142 | 2 | 4-$CF_3$ | 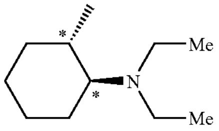 | | F: 517, NMR: 10.24 (1H, s), 7.74 (1H, d), 3.23 (3H, s), 2.83 (2H, t), 1.86-1.59 (2H, m). |
| 143 | 2 | 4-$CF_3$ | 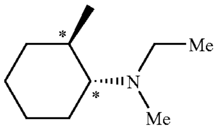 | | F: 503, NMR: 10.25 (1H, s), 7.75 (1H, d), 3.23 (3H, s), 2.83 (2H, t), 1.82-1.58 (3H, m). |
TABLE 29
| | | | | | |
|---|---|---|---|---|---|
| 144 | 2 | 5-Cl | 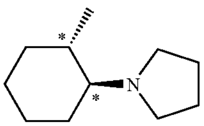 | HCl | ES: 481, NMR: 10.34 (1H, s), 7.76 (1H, d), 7.48-7.37 (2H, m), 3.97-3.85 (1H, m), 2.84 (2H, t), 1.67-1.51 (2H, m). |
| 145 | 2 | 4- 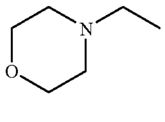 | cHex | 2HCl | F: 477, NMR: 10.13 (1H, s), 7.76 (1H, d), 7.47-7.39 (2H, m), 4.27 (2H, d), 4.00-3.82 (4H, m), 3.55-3.44 (1H, m). |

TABLE 29-continued
| | | | | | |
|---|---|---|---|---|---|
| 146 | 2 | 4-$CF_3$ | 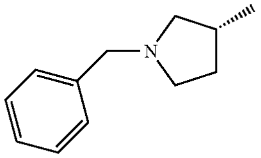 | | F: 523, NMR: 10.20 (1H, s), 7.20 (1H, d), 3.65-3.57 (2H, m), 2.86-2.81 (2H, m) |
| 147 | 2 | 5-F | cHex | | ES: 396, NMR: 10.08 (1H, s), 7.57 (1H, dd), 7.25-7.13 (2H, m), 3.24 (3H, s), 2.83 (2H, t), 1.98-1.86 (2H, m). |
| 148 | 2 | 4-F | cHex | | F: 396, NMR: 10.02 (1H, s), 7.77 (1H, dd), 7.42-7.35 (2H, m), 6.54 (1H, dd), 3.23 (3H, s), 2.82 (2H, t), 1.96-1.86 (2H, m). |
| 149 | 2 | 4-$CF_3$ | 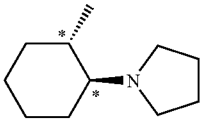 | HCl | F: 515, NMR: 10.51 (1H, s), 7.19 (1H, d), 2.86-2.82 (2H, m), 2.12-1.26 (12H, m) |
| 150 | 96 | 4-$CF_3$ | 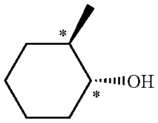 | | F: 462, NMR: 7.82 (1H, d), 6.87 (1H, d), 2.84 (2H, t), 1.99-1.97 (1H, m) |
| 151 | 97 | 4-$CF_3$ | 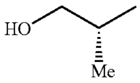 | | F: 422, NMR: 10.27 (1H, s), 7.40 (1H, dd), 4.90 (1H, t), 2.85-2.81 (2H, m) |
| 152 | 97 | 4-$CF_3$ | 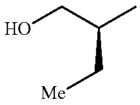 | | F: 436, NMR: 10.27 (1H, s), 7.18 (1H, d), 4.83 (1H, t), 2.85-2.82 (2H, m) |
| 153 | 97 | 4-$CF_3$ | 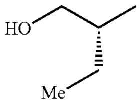 | | F: 436, NMR: 10.27 (1H, s), 7.18 (1H, d), 4.83 (1H, t), 2.85-2.82 (2H, m) |
| 154 | 97 | 4-$CF_3$ | 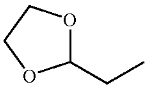 | | F: 450, NMR: 10.32 (1H, s), 7.40 (1H, dd), 5.04 (1H, t), 2.85-2.82 (2H, m) |
| 155 | 97 | 4-$CF_3$ | 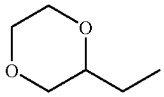 | | ES: 464, NMR: 10.32 (1H, s), 7.19 (1H, d), 3.80-3.57 (5H, m), 2.85-2.82 (2H, m) |
| 156 | 98 | 4-Cl, 5-Me | 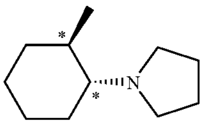 | HCl | F: 495, NMR: 7.69 (1H, s), 3.89-3.87 (1H, m), 2.83 (2H, t), 2.27 (3H, s) |
| 157 | 98 | 4-Cl, 5-Me | 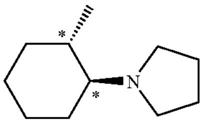 | HCl | F: 495, NMR: 7.69 (1H, s), 3.88-3.87 (1H, m), 2.83 (2H, t), 2.27 (3H, s) |
| 158 | 98 | 4-Cl, 5-Br | 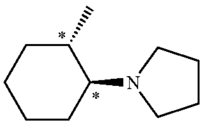 | HCl | F: 561, NMR: 8.03 (1H, s), 7.19 (1H, d), 3.96-3.94 (1H, m), 2.84 (2H, t) |

TABLE 30
| | | | | | |
|---|---|---|---|---|---|
| 159 | 98 | 4-Cl, 5-Cl | 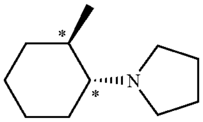 | HCl | F: 515, NMR: 7.94 (1H, s), 7.19 (1H, d), 3.97-3.96 (1H, m), 2.83 (2H, t) |
| 160 | 98 | 4-Cl, 5-F | 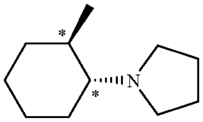 | HCl | F: 499, NMR: 10.41 (1H, s), 7.82 (1H, d), 7.52-7.38 (2H, m), 4.01-3.88 (1H, m), 2.83 (2H, t), 1.67-1.48 (2H, m). |
| 161 | 98 | 4-Cl, 5-F | 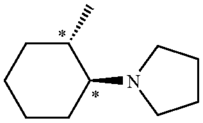 | HCl | F: 499, NMR: 10.39 (1H, s), 7.82 (1H, d), 7.50-7.40 (2H, m), 4.00-3.97 (1H, m), 2.83 (2H, t), 1.67-1.48 (2H, m). |
| 162 | 98 | 4-Cl, 5-Cl | 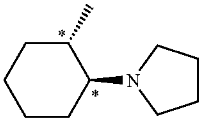 | HCl | F: 515, NMR: 7.94 (1H, s), 7.19 (1H, d), 3.98-3.97 (1H, m), 2.84 (2H, t) |
| 163 | 98 | 4-$NO_2$ | 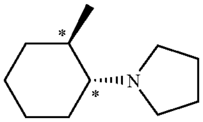 | HCl | ES: 492, NMR: 10.65 (1H, s), 7.89 (1H, d), 7.56-7.42 (2H, m), 4.13-4.00 (1H, m), 3.24 (3H, s), 2.84 (2H, t), 2.16-1.99 (2H, m). |
| 164 | 98 | 4-$CF_3$ | 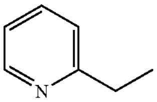 | HCl | F: 455, NMR: 8.21 (1H, t), 7.88 (1H, d), 4.81 (2H, s), 2.84 (2H, t) |
| 165 | 98 | 4-$CF_3$ | 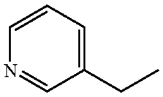 | HCl | F: 455, NMR: 8.87 (1H, s), 7.86 (1H, d), 4.73 (2H, s), 2.84 (2H, t) |
| 166 | 98 | 4-Cl | 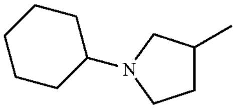 | HCl | ES: 481, NMR: 10.23 (1H, s), 7.82-7.72 (2H, m), 7.17 (1H, d), 6.82-6.74 (2H, m), 2.83 (2H, t), 1.65-1.54 (1H, m). |
| 167 | 98 | 4-$CF_3$ | 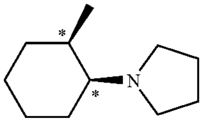 | HCl | ES: 515, NMR: 10.49 (1H, s), 8.02-7.93 (2H, m), 7.07 (1H, d), 4.64-4.51 (1H, m), 2.85 (2H, t), 2.16-1.74 (7H, m). |
| 168 | 98 | 4-Cl | 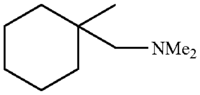 | | ES: 469, EA: $C_{26}H_{33}ClN_4O_2$, Calcd C, 66.58; H, 7.09; N, 11.95; Cl, 7.56. Found C, 66.36; H, 7.10; N, 11.88; Cl, 7.55. |
| 169 | 98 | 4-Cl | 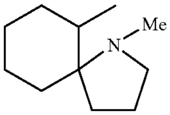 | | ES: 481, EA: $C_{27}H_{33}ClN_4O_2$, Calcd C, 66.42; H, 6.98; N, 11.48; Cl, 7.26. Found C, 66.75; H, 6.78; N, 11.37; Cl, 7.55. |
| 170 | 98 | 4-$CF_3$ | 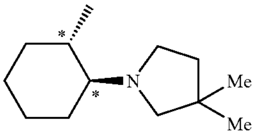 | | F: 543, EA: $C_{30}H_{37}F_3N_4O_2$, Calcd C, 66.40; H, 6.87; N, 10.32; F, 10.50. Found C, 66.31; H, 6.83; N, 10.55; F, 10.58. |

TABLE 30-continued
| | | | | | |
|---|---|---|---|---|---|
| 171 | 98 | 4-$CF_3$ | 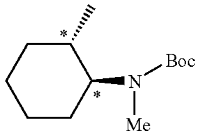 | | F: 575, NMR: 10.25 (0.5H, s), 10.16 (0.5H, s), 7.85-7.75 (1H, m), 6.90-6.84 (1H, m), 3.23 (3H, s), 1.32 (4.5H, s), 1.25 (4.5H, s). |
| 172 | 98 | 4-$CF_3$ | 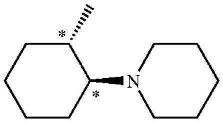 | 0.5 Fum | F: 529, NMR: 10.30 (1H, s), 7.72 (1H, d), 6.95-6.90 (2H, m), 3.23 (3H, s), 2.86-2.80 (2H, m), 1.87-1.72 (2H, m), 1.68-1.60 (1H, m). |
TABLE 31
| | | | | | |
|---|---|---|---|---|---|
| 173 | 98 | 4-$CF_3$ | 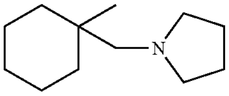 | HCl | F: 529, NMR: 7.93 (1H, d), 7.05 (1H, s), 3.06 (2H, bs), 2.84 (2H, t) |
| 174 | 98 | 4-OMe | 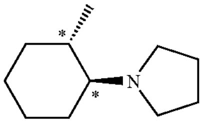 | HCl | F: 477, NMR: 7.43-7.40 (2H, m), 3.95-3.94 (1H, m), 3.81 (3H, s), 2.82 (2H, t) |
| 175 | 98 | 4-$CF_3$ | 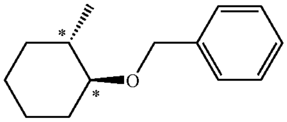 | | F: 552, NMR: 7.65 (1H, d), 6.98 (1H, d), 4.53 (2H, dd), 2.89 (2H, t) |
| 176 | 98 | 4-$CF_3$ | 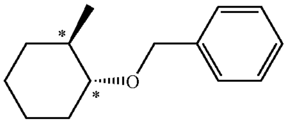 | | F: 552, EA: $C_{31}H_{32}F_3N_3O_3$, Calcd C, 67.50; H, 5.85; N, 7.62; F, 10.33. Found C, 67.22; H, 5.94; N, 7.40; F, 10.19. |
| 177 | 98 | 4-$CF_3$ | 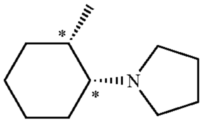 | HCl | F: 515, NMR: 7.49 (1H, dd), 7.06 (1H, d), 4.59-4.56 (1H, m), 2.85 (2H, t) |
| 178 | 98 | 4-$CF_3$ | 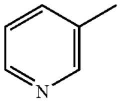 | HCl | F: 441, NMR: 8.04 (1H, d), 7.79-7.74 (2H, m), 3.21 (3H, s), 2.82 (2H, t) |
| 179 | 98 | 4-$CF_3$ | 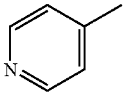 | HCl | F: 441, NMR: 8.29 (2H, d), 7.98 (1H, d), 3.19 (3H, s), 2.82 (2H, t) |
| 180 | 98 | 4-Me | 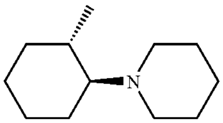 | Fum | F: 475, NMR: 9.95 (1H, s), 7.42-7.38 (1H, m), 3.23 (3H, s), 2.82 (2H, t), 2.30-2.22 (4H, m), 1.90-1.72 (2H, m). |
| 181 | 99 | 4-F | 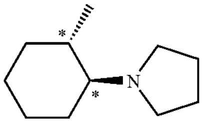 | HCl | F: 465, NMR: 10.23 (1H, s), 7.81 (1H, dd), 7.48-7.39 (2H, m), 3.99-3.86 (1H, m), 2.83 (2H, t), 1.67-1.50 (2H, m). |

TABLE 31-continued
| | | | | | |
|---|---|---|---|---|---|
| 182 | 99 | 5-Br | 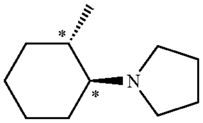 | HCl | F: 525, NMR: 10.34 (1H, s), 7.85 (1H, d), 7.03 (1H, d), 3.96-3.85 (1H, m), 2.84 (2H, t), 1.66-1.50 (2H, m). |
| 183 | 99 | 4-Br | 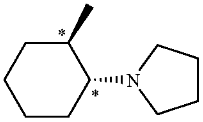 | HCl | F: 525, NMR: 10.33 (1H, s), 7.66 (1H, d), 6.89 (1H, dd), 4.02-3.90 (1H, m), 2.83 (2H, t), 1.67-1.51 (2H, m). |
| 184 | 100 | 4-$CF_3$ | 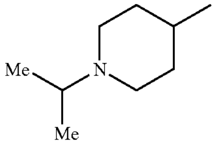 | HCl | F: 489, NMR: 10.39 (1H, s), 7.41 (1H, dd), 2.85-2.81 (2H, m), 1.29 (6H, d) |
| 185 | 100 | 4-$CF_3$ | 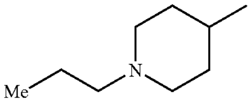 | HCl | F: 489, NMR: 10.70 (1H, s), 7.41 (1H, dd), 2.85-2.82 (2H, m), 0.92 (3H, t) |
| 186 | 100 | 4-$CF_3$ | 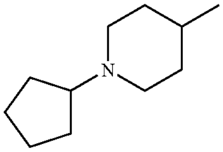 | HCl | F: 515, NMR: 10.39 (1H, s), 7.41 (1H, dd), 2.85-2.82 (2H, m), 2.16-1.50 (12H, m) |
| 187 | 100 | 4-$CF_3$ | 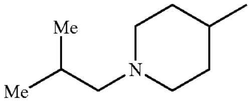 | HCl | F: 503, NMR: 10.41 (1H, s), 7.41 (1H, dd), 2.86-2.82 (2H, m), 1.00 (6H, d) |
TABLE 32
| | | | | | |
|---|---|---|---|---|---|
| 188 | 100 | 4-$CF_3$ | 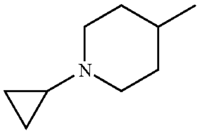 | HCl | F: 487, NMR: 10.38 (1H, s), 7.40 (1H, dd), 2.85-2.82 (2H, m), 0.82-0.77 (2H, m) |
| 189 | 100 | 4-$CF_3$ | 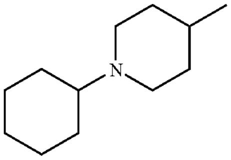 | HCl | F: 529, NMR: 10.39 (1H, s), 7.40 (1H, dd), 2.85-2.82 (2H, m), 2.16-1.07 (14H, m) |
| 190 | 100 | 4-$CF_3$ | 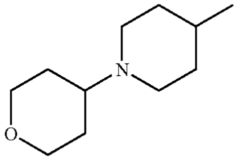 | HCl | F: 531, NMR: 10.38 (1H, s), 7.40 (1H, dd), 2.85-2.82 (2H, m), 2.18-1.67 (8H, m) |
| 191 | 100 | 4-$CF_3$ | 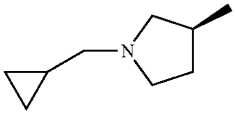 | HCl | F: 487, NMR: 10.45 (1H, s), 7.52 (1H, dd), 2.86-2.82 (2H, m), 0.63-0.37 (4H, m) |

TABLE 32-continued
| | | | | | |
|---|---|---|---|---|---|
| 192 | 100 | 4-$CF_3$ | 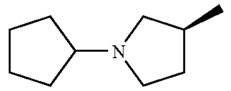 | HCl | F: 501, NMR: 10.43 (1H, s), 7.43-7.40 (1H, m), 2.85-2.82 (2H, m), 2.35-1.50 (9H, m) |
| 193 | 100 | 4-$CF_3$ | 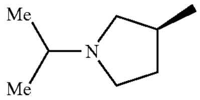 | HCl | F: 475, NMR: 10.44 (1H, s), 7.19 (1H, d), 2.86-2.82 (2H, m), 1.29 (6H, d) |
| 194 | 100 | 4-$CF_3$ | 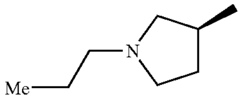 | HCl | F: 475, NMR: 10.43 (1H, s), 7.41 (1H, dd), 2.86-2.82 (2H, m), 0.93-0.89 (3H, m) |
| 195 | 100 | 4-$CF_3$ | 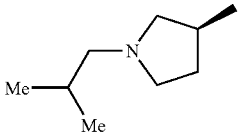 | HCl | F: 489, NMR: 10.45 (1H, s), 7.41 (1H, dd), 2.85-2.82 (2H, m), 0.98-0.97 (6H, m) |
| 196 | 100 | 4-$CF_3$ | 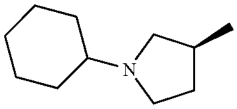 | HCl | F: 515, NMR: 10.43 (1H, s), 7.41 (1H, dd), 2.86-2.82 (2H, m), 2.10-1.05 (11H, m) |
| 197 | 100 | 4-$CF_3$ | 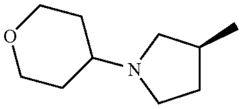 | | F: 517, NMR: 10.31 (1H, s), 7.39 (1H, dd), 2.85-2.82 (2H, m), 1.78-1.30 (5H, m) |
| 198 | 100 | 4-$CF_3$ | 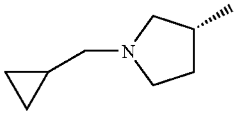 | HCl | F: 487, NMR: 10.44 (1H, s), 7.19 (1H, d), 2.86-2.82 (2H, m), 0.61-0.38 (4H, m) |
| 199 | 100 | 4-$CF_3$ | 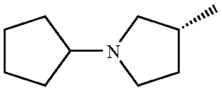 | HCl | F: 501, NMR: 10.43 (1H, s), 7.05 (1H, d), 2.86-2.82 (2H, m), 2.03-1.49 (3H, m) |
| 200 | 100 | 4-$CF_3$ | 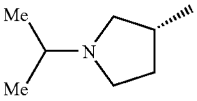 | HCl | F: 475, NMR: 10.43 (1H, s), 7.05 (1H, d), 2.86-2.82 (2H, m), 1.29 (6H, d) |
| 201 | 100 | 4-$CF_3$ | 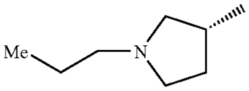 | HCl | F: 475, NMR: 10.45 (1H, s), 7.05 (1H, d), 2.85-2.82 (2H, m), 0.93-0.88 (3H, m) |
| 202 | 100 | 4-$CF_3$ | 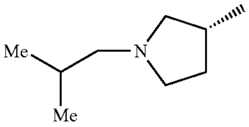 | HCl | F: 489, NMR: 10.45 (1H, s), 7.41 (1H, dd), 2.85-2.82 (2H, m), 0.99-0.97 (6H, m) |
| 203 | 100 | 4-$CF_3$ | 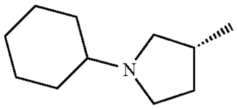 | HCl | F: 515, NMR: 10.43 (1H, s), 7.41 (1H, dd), 2.85-2.82 (2H, m), 2.10-1.05 (11H, m) |
| 204 | 100 | 4-$CF_3$ | 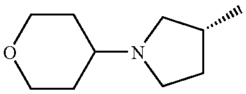 | | F: 517, NMR: 10.32 (1H, s), 7.39 (1H, dd), 2.85-2.82 (2H, m), 1.80-1.29 (5H, m) |

TABLE 33
| | | | | | |
|---|---|---|---|---|---|
| 205 | 100 | 4-$CF_3$ | 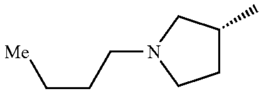 | HCl | F: 489, NMR: 10.32 (1H, s), 7.19 (1H, d), 2.86-2.82 (2H, m), 0.92-0.87 (3H, m) |
| 206 | 100 | 4-$CF_3$ | 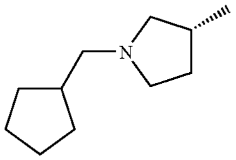 | HCl | F: 515, NMR: 10.32 (1H, s), 7.41 (1H, dd), 2.86-2.82 (2H, m), 2.24-1.20 (10H, m) |
| 207 | 100 | 4-$CF_3$ | 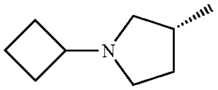 | HCl | F: 487, NMR: 10.43 (1H, s), 7.19 (1H, d), 2.86-2.82 (2H, m), 2.42-1.63 (7H, m) |
| 208 | 100 | 4-$CF_3$ | 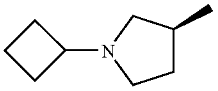 | HCl | F: 487, NMR: 10.43 (1H, s), 7.19 (1H, d), 2.86-2.82 (2H, m), 2.43-1.62 (7H, m) |
| 209 | 100 | 4-$CF_3$ | 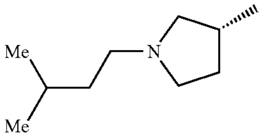 | HCl | F: 503, NMR: 10.43 (1H, s), 7.19 (1H, d), 2.86-2.82 (2H, m), 0.89 (6H, t) |
| 210 | 100 | 4-$CF_3$ | 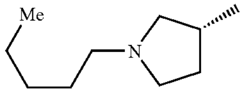 | HCl | F: 503, NMR: 10.43 (1H, s), 7.19 (1H, d), 2.86-2.82 (2H, m), 0.90-0.85 (3H, m) |
| 211 | 100 | 4-$CF_3$ | 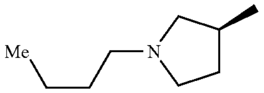 | HCl | F: 489, NMR: 10.44 (1H, s), 7.19 (1H, d), 2.85-2.82 (2H, m), 0.92-0.87 (3H, m) |
| 212 | 100 | 4-$CF_3$ | 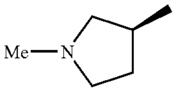 | HCl | F: 447, NMR: 10.45 (1H, s), 7.19 (1H, d), 2.85-2.82 (5H, m), 2.56-2.52 (2H, m) |
| 213 | 100 | 4-Cl | 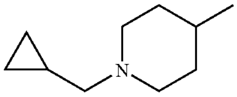 | HCl | F: 467, NMR: 10.20 (1H, s), 7.17 (1H, d), 2.85-2.82 (3H, m), 0.67-0.38 (4H, m) |
| 214 | 100 | 4-Cl | 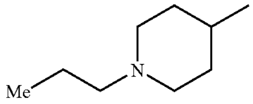 | HCl | ES: 455, NMR: 10.21 (1H, s), 7.16 (1H, d), 2.84-2.81 (3H, m), 0.92 (3H, t) |
| 215 | 100 | 4-Cl | 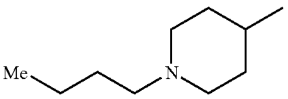 | HCl | F: 469, NMR: 10.20 (1H, s), 7.16 (1H, d), 2.85-2.81 (3H, m), 0.92 (3H, t) |
| 216 | 100 | 4-Cl | 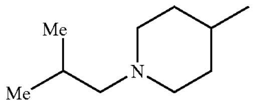 | HCl | F: 469, NMR: 10.23 (1H, s), 7.17 (1H, d), 2.85-2.81 (3H, m), 1.00 (6H, d) |
| 217 | 100 | 4-Cl | 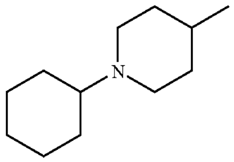 | HCl | F: 495, NMR: 10.19 (1H, s), 7.16 (1H, d), 2.85-2.81 (3H, m), 2.16-1.06 (14H, m) |

TABLE 33-continued
| | | | | | |
|---|---|---|---|---|---|
| 218 | 11 | 4-Cl | 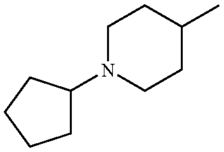 | HCl | ES: 481, NMR: 10.23 (1H, s), 7.16 (1H, d), 2.85-2.81 (3H, m), 2.16-1.52 (12H, m) |
| 219 | 100 | 4-Cl | 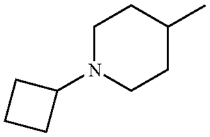 | HCl | ES: 467, NMR: 10.20 (1H, s), 7.16 (1H, d), 2.85-2.81 (3H, m), 2.45-1.61 (10H, m) |
| 220 | 100 | 4-Cl | 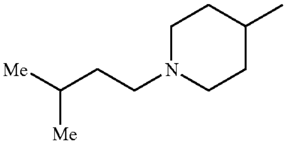 | HCl | ES: 483, NMR: 10.20 (1H, s), 7.17 (1H, d), 2.85-2.81 (3H, m), 0.92 (6H, d) |
| 221 | 100 | 4-$CF_3$ | 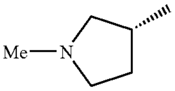 | HCl | F: 447, NMR: 10.44 (1H, s), 7.19 (1H, d), 2.86-2.82 (5H, m), 2.56-2.52 (2H, m) |
TABLE 34
| | | | | | |
|---|---|---|---|---|---|
| 222 | 100 | 4-$CF_3$ | 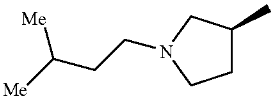 | HCl | F: 503, NMR: 10.44 (1H, s), 7.19 (1H, d), 2.86-2.82 (2H, m), 0.90 (6H, d) |
| 223 | 100 | 4-$CF_3$ | 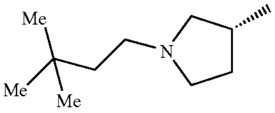 | HCl | F: 517, NMR: 10.43 (1H, s), 7.19 (1H, d), 2.86-2.82 (2H, m), 0.90 (9H, s) |
| 224 | 100 | 4-$CF_3$ | 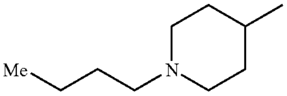 | HCl | F: 503, NMR: 10.38 (1H, s), 7.19 (1H, d), 2.86-2.82 (2H, m), 0.92 (3H, t) |
| 225 | 100 | 4-$CF_3$ | 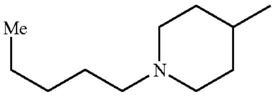 | HCl | F: 517, NMR: 10.38 (1H, s), 7.18 (1H, d), 2.86-2.82 (2H, m), 0.90 (3H, t) |
| 226 | 100 | 4-$CF_3$ | 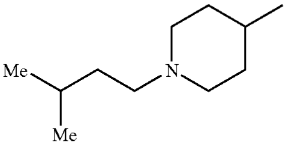 | HCl | F: 517, NMR: 10.39 (1H, s), 7.18 (1H, d), 2.85-2.82 (2H, m), 0.91 (6H, d) |
| 227 | 100 | 4-$CF_3$ | 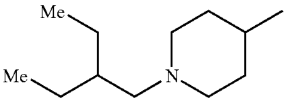 | HCl | F: 531, NMR: 10.40 (1H, s), 7.19 (1H, d), 2.85-2.82 (2H, m), 0.86 (6H, t) |
| 228 | 100 | 4-$CF_3$ | 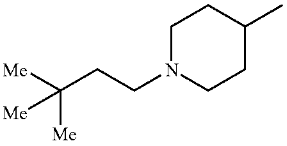 | HCl | F: 531, NMR: 10.38 (1H, s), 7.19 (1H, d), 2.85-2.82 (2H, m), 0.92 (9H, s) |

TABLE 34-continued
| | | | | | |
|---|---|---|---|---|---|
| 229 | 100 | 4-$CF_3$ | 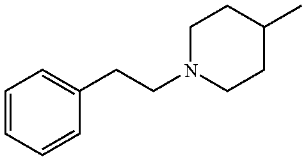 | HCl | F: 551, NMR: 10.38 (1H, s), 7.19 (1H, d), 2.86-2.82 (2H, m), 2.21-1.76 (4H, m) |
| 230 | 100 | 4-$CF_3$ | 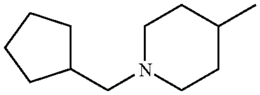 | HCl | F: 529, NMR: 10.39 (1H, s), 7.19 (1H, d), 2.86-2.82 (2H, m), 2.33-1.21 (13H, m) |
| 231 | 100 | 4-$CF_3$ | 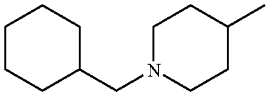 | HCl | F: 543, NMR: 10.39 (1H, s), 7.19 (1H, d), 2.86-2.82 (2H, m), 2.14-0.90 (15H, m) |
| 232 | 100 | 4-$CF_3$ | 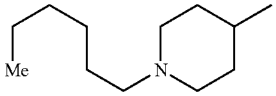 | HCl | F: 531, NMR: 10.37 (1H, s), 7.18 (1H, d), 2.86-2.82 (2H, m), 0.90-0.87 (3H, m) |
| 233 | 100 | 4-$CF_3$ | 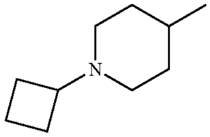 | HCl | F: 501, NMR: 10.38 (1H, s), 7.18 (1H, d), 2.85-2.82 (2H, m), 2.45-1.61 (10H, m) |
| 234 | 100 | 4-Cl | 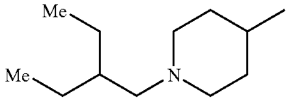 | HCl | F: 497, NMR: 10.20 (1H, s), 7.17 (1H, d), 2.85-2.81 (2H, m), 0.87 (6H, t) |
| 235 | 101 | 4-$CF_3$ | 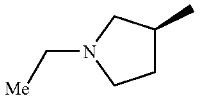 | HCl | ES: 461, NMR: 10.44 (1H, s), 7.19 (1H, d), 2.85-2.82 (2H, m), 1.25-1.22 (3H, m) |
| 236 | 101 | 4-$CF_3$ | 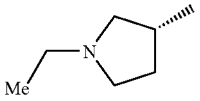 | HCl | F: 461, NMR: 10.44 (1H, s), 7.19 (1H, d), 2.86-2.82 (2H, m), 1.26-1.22 (3H, m) |
TABLE 35
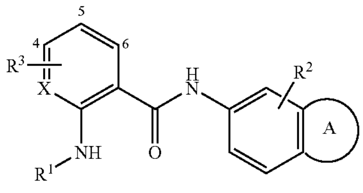
| Ex | Syn | $R^3$ | X | $R^1$ | 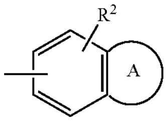 | Sal | Dat |
|---|---|---|---|---|---|---|---|
| 105 | 105 | 4-$CF_3$ | CH | cHex | 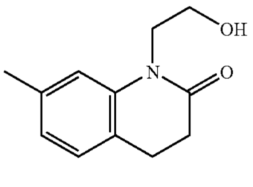 | | F: 476, NMR: 10.29 (1H, s), 7.85 (1H, d), 7.17 (1H, d), 3.90 (1H, t), 2.82 (2H, t), 1.96-1.85 (2H, m). |

TABLE 35-continued
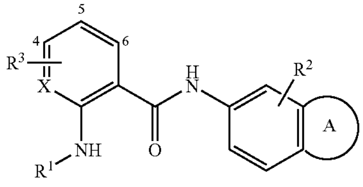
| Ex | Syn | $R^3$ | X | $R^1$ | 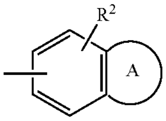 | Sal | Dat |
|---|---|---|---|---|---|---|---|
| 106 | 106 | 4-Cl | CH | 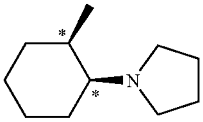 | 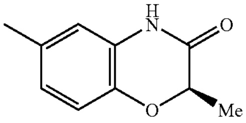 | HCl | F: 483, NMR: 10.74 (1H, s), 10.26 (1H, s), 7.77 (1H, d), 6.78 (1H, d), 4.62 (1H, q), 3.60-3.47 (1H, m), 2.14-1.73 (7H, m). |
| 107 | 107 | 4-$CF_3$ | CH | 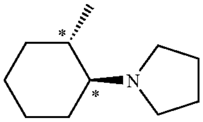 | 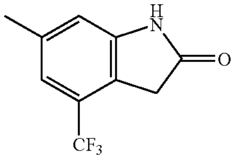 | HCl | F: 555, NMR: 10.86 (1H, s), 10.78 (1H, s), 7.29 (1H, s), 7.13 (1H, d), 3.61 (2H, s), 2.12-1.23 (12H, m) |
| 108 | 108 | 4-$CF_3$ | CH | 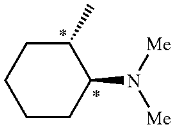 | 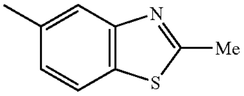 | HCl | F: 477, NMR: 10.79 (1H, s), 7.89 (1H, d), 2.80 (3H, s), 2.74 (3H, d), 2.71 (3H, d) |
| 109 | 109 | 4-$CF_3$ | CH | 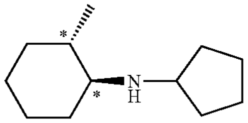 | 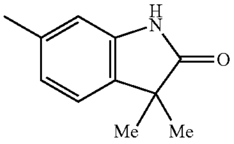 | HCl | F: 529, NMR: 7.79 (1H, d), 7.04 (1H, d), 3.20 (1H, bs), 1.24 (6H, s) |
| 110 | 110 | 4-$CF_3$ | CH | 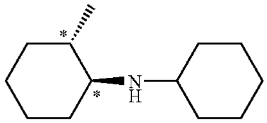 | 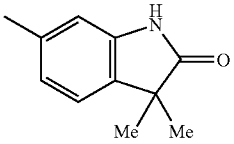 | HCl | F: 543, NMR: 7.77 (1H, d), 7.00 (1H, d), 3.15 (1H, bs), 1.24 (6H, d) |
| 111 | 111 | 4-$CF_3$ | CH | 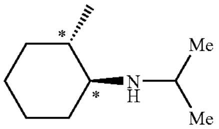 | 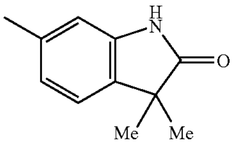 | HCl | F: 503, NMR: 7.82 (1H, d), 7.04 (1H, d), 3.50 (1H, bs), 1.24 (6H, s) |
| 112 | 112 | 4-$CF_3$ | CH | 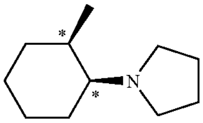 | 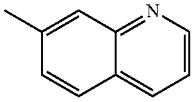 | 2HCl | ES: 483, NMR: 11.30 (1H, s), 9.14 (1H, d), 7.91-7.76 (2H, m), 7.32 (1H, s), 7.08 (1H, d), 4.62 (1H, d), 2.16-2.06 (1H, m). |
| 113 | 113 | 4- 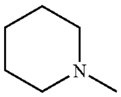 | N | cHex | 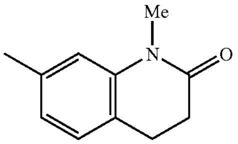 | | F: 462, NMR: 9.55 (1H, s), 7.93 (1H, d), 6.05 (1H, d), 3.92-3.82 (1H, m), 3.24 (3H, s), 2.81 (2H, t), 1.99-1.89 (2H, m). |

TABLE 36
| | | | | | | | |
|---|---|---|---|---|---|---|---|
| 114 | 114 | 4-$CF_3$ | CH | cHex | 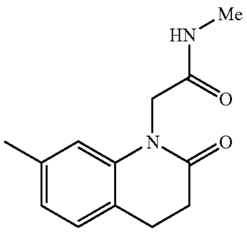 | | ES: 503, NMR: 10.29 (1H, s), 7.82 (1H, d), 4.37 (2H, s), 3.56-3.46 (1H, m), 2.87 (2H, t), 1.95-1.85 (2H, m). |
| 237 | 1 | 4-Cl | CH | cHex | 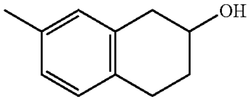 | | F: 399, NMR: 9.94 (1H, s), 7.78 (1H, d), 7.68 (1H, d), 7.00 (1H, d), 6.59 (1H, q), 3.90 (1H, m). |
| 238 | 1 | 4-$CF_3$ | N | 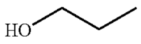 | 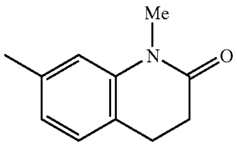 | | F: 409, NMR: 10.43 (1H s), 7.47 (1H, d), 7.20 (1H, d), 7.08 (1H, d), 3.58 (2H, q), 3.24 (3H, s), 2.84 (2H, t). |
| 239 | 1 | 4-$CF_3$ | N | 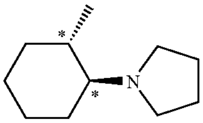 | 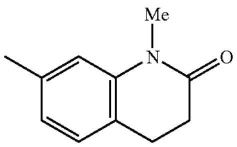 | | F: 516, NMR: 10.41 (1H, s), 8.22 (1H, d), 7.20 (1H, d), 7.05 (1H, d), 3.24 (3H, s), 2.84 (2H, m), 1.80-1.20 (12H, m). |
| 240 | 1 | 4-$CF_3$ | N | 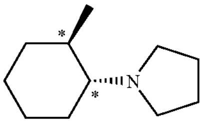 | 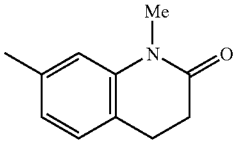 | | F: 516, NMR: 10.41 (1H, s), 8.22 (1H, d), 7.20 (1H, d), 7.02 (1H, d), 3.24 (3H, s), 2.84 (2H, m) 1.80-1.20 (12H, m). |
| 241 | 1 | 4-$CF_3$ | N | 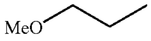 | 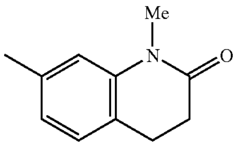 | | F: 423, NMR: 10.44 (1H, s), 8.24 (1H, d), 7.09 (1H, d), 3.28 (3H, s), 3.24 (3H, s). |
| 242 | 1 | 4-$CF_3$ | N | 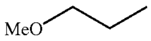 | 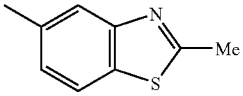 | | F: 411, NMR: 10.61 (1H, s), 7.99 (1H, d), 7.11 (1H, d), 3.62-3.51 (4H, m), 2.80 (3H, s). |
| 243 | 2 | 4-$CF_3$ | CH | 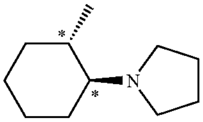 | 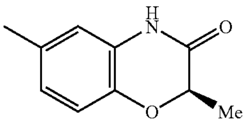 | HCl | F: 517, NMR: 10.43 (1H, s), 6.94 (1H, d), 4.62 (1H, q), 1.41 (3H, d) |
| 244 | 2 | 4-$CF_3$ | CH | 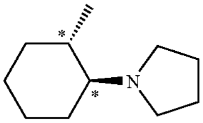 | 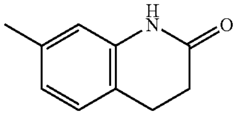 | HCl | ES: 501, NMR: 10.45 (1H, s), 7.13 (1H, d), 2.86-2.81 (2H, m), 2.11-1.23 (12H, m) |
| 245 | 2 | 4-Cl | CH | 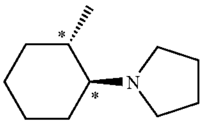 | 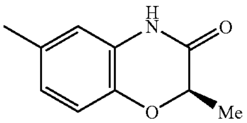 | HCl | F: 483, NMR: 10.26 (1H, s), 6.93 (1H, d), 4.62 (1H, q), 1.41 (3H, d) |

TABLE 36-continued
| | | | | | | | |
|---|---|---|---|---|---|---|---|
| 246 | 2 | 4-Cl | CH | cHex | 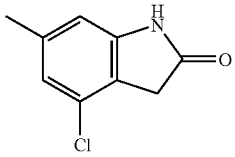 | | F: 418, NMR: 10.62 (1H, s), 10.16 (1H, s), 7.74 (1H, d), 7.70 (1H, d), 6.78 (1H, d), 1.95-1.85 (2H, m), 1.72-1.52 (3H, m). |
| 247 | 2 | 4-$CF_3$ | CH | 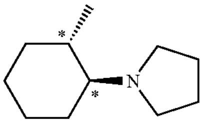 | 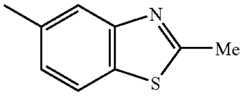 | HCl | F: 503, NMR: 10.72 (1H, s), 7.03 (1H, d), 2.80 (3H, s), 2.13-1.29 (12H, m) |
| 248 | 2 | 4-$CF_3$ | CH | 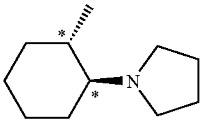 | 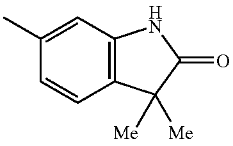 | HCl | F: 515, NMR: 10.46 (1H, s), 10.42 (1H, s), 7.02 (1H, dd), 4.12-4.01 (1H, m), 2.12-1.21 (12H, m), 1.24 (6H, s) |
TABLE 37
| | | | | | | | |
|---|---|---|---|---|---|---|---|
| 249 | 2 | 4-$CF_3$ | CH | 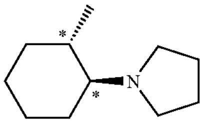 | 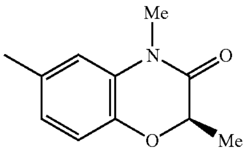 | HCl | F: 531, NMR: 10.54 (1H, s), 7.24 (1H, d), 4.70 (1H, q), 1.44 (3H, d) |
| 240 | 2 | 4-$CF_3$ | CH | 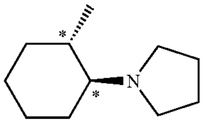 | 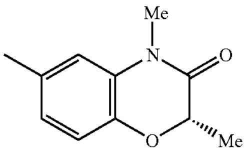 | HCl | F: 531, NMR: 10.55 (1H, s), 7.23 (1H, d), 4.70 (1H, q), 1.44 (3H, d) |
| 251 | 2 | 4-Cl | CH | 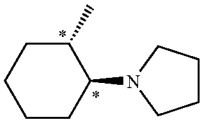 | 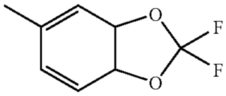 | HCl | F: 478, NMR: 10.50 (1H, s), 7.73 (1H, d), 3.96 (1H, m), 2.12-1.23 (12H, m) |
| 252 | 2 | 4-Cl | CH | cHex | 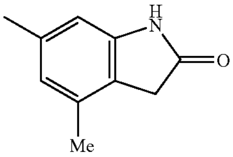 | | F: 398, NMR: 10.34 (1H, s), 9.98 (1H, s), 7.77 (1H, d), 7.69 (1H, d), 7.04 (1H, d), 6.75 (1H, d), 1.94-1.83 (2H, m), 1.71-1.51 (3H, m). |
| 253 | 2 | 4-Cl | CH | 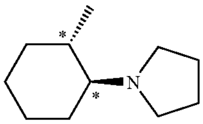 | 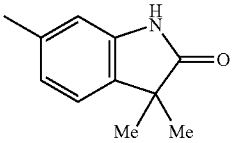 | HCl | F: 481, NMR: 10.27 (1H, s), 6.75 (1H, dd), 2.11-1.20 (12H, m), 1.24 (6H, s) |
| 254 | 2 | 4-Cl | CH | 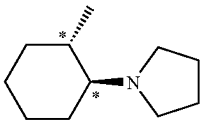 | 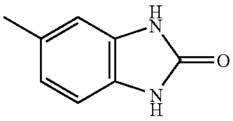 | HCl | F: 454, NMR: 10.65 (1H, s), 10.57 (1H, s), 10.18 (1H, s), 7.34 (1H, d), 2.11-1.25 (12H, m) |

TABLE 37-continued
| | | | | | | |
|---|---|---|---|---|---|---|
| 255 | 2 | 4-Cl | CH | 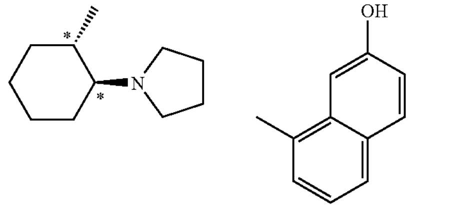 | HCl | ES: 464, NMR: 8.14 (1H, d), 7.73 (1H, d), 4.14 (1H, m), 2.10-1.24 (12H, m) |
| 256 | 2 | 4-Cl | CH | 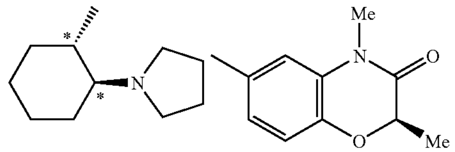 | HCl | F: 497, NMR: 10.32 (1H, s), 6.99 (1H, d), 4.69 (1H, q), 1.43 (3H, d) |
| 257 | 2 | 4-Cl | CH | 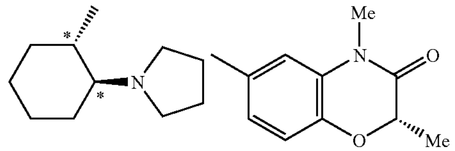 | HCl | F: 497, NMR: 10.31 (1H, s), 6.99 (1H, d), 4.69 (1H, q), 1.43 (3H, d) |
| 258 | 2 | 4-Cl | CH | 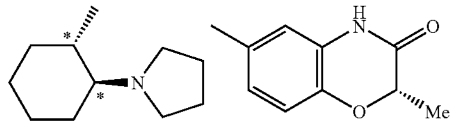 | HCl | F: 483, NMR: 10.24 (1H, s), 6.93 (1H, d), 4.62 (1H, q), 1.41 (3H, d) |
| 259 | 2 | 4-$CF_3$ | CH | 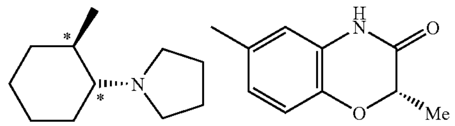 | HCl | F: 517, NMR: 10.42 (1H, s), 7.02 (1H, d), 4.62 (1H, q), 1.42 (3H, d) |
| 260 | 2 | 4-$CF_3$ | CH | 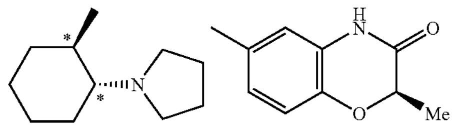 | HCl | F: 517, NMR: 10.45 (1H, s), 7.01 (1H, d), 4.62 (1H, q), 1.41 (3H, d) |
TABLE 38
| | | | | | | |
|---|---|---|---|---|---|---|
| 261 | 2 | 4-$CF_3$ | CH | 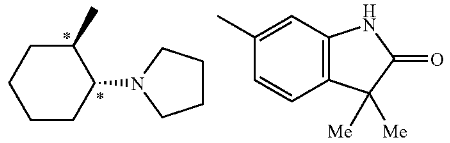 | HCl | F: 515, NMR: 10.47 (1H, s), 10.42 (1H, s), 7.02 (1H, dd), 4.14-4.01 (1H, m), 2.12-1.22 (12H, m), 1.24 (6H, s). |
| 262 | 2 | 4-$CF_3$ | CH | 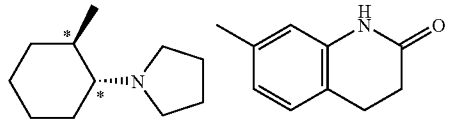 | HCl | F: 501, NMR: 10.45 (1H, s), 7.13 (1H, d), 2.86-2.82 (2H, m), 2.11-1.26 (12H, m) |
| 263 | 2 | 4-$CF_3$ | CH | 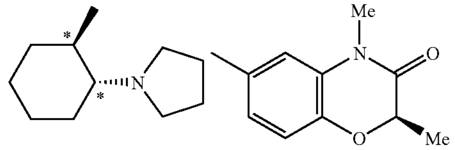 | HCl | F: 531, NMR: 10.50 (1H, s), 7.23 (1H, d), 4.69 (1H, q), 1.44 (3H, d) |

TABLE 38-continued
| | | | | | | | |
|---|---|---|---|---|---|---|---|
| 264 | 2 | 4-$CF_3$ | CH | 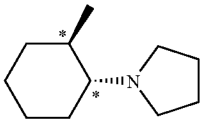 | 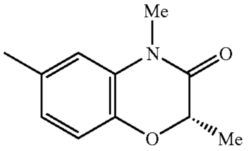 | HCl | F: 531, NMR: 10.55 (1H, s), 7.24 (1H, d), 4.70 (1H, q), 1.44 (3H, d) |
| 265 | 2 | 4-$CF_3$ | CH | 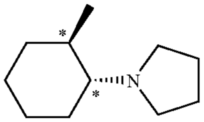 | 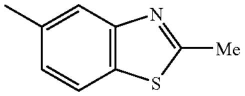 | HCl | F: 503, NMR: 10.74 (1H, s), 7.03 (1H, d), 2.80 (3H, s), 2.14-1.29 (12H, m) |
| 266 | 2 | 4-$CF_3$ | CH | 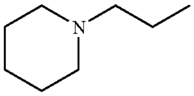 | 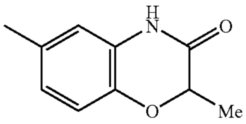 | HCl | F: 477, NMR: 10.76 (1H, s), 7.81 (1H, d), 7.08 (1H, s), 4.62 (1H, q), 1.85-1.65 (5H, m) |
| 267 | 2 | 4-Cl | CH | 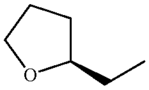 | 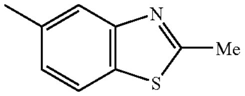 | | F: 402, NMR: 10.30 (1H, s), 7.75 (1H, d), 4.06-3.64 (3H, m), 2.79 (3H, s) |
| 268 | 2 | 4-Cl | CH | 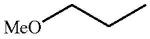 | 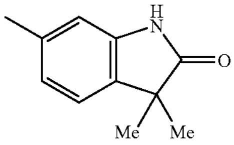 | | F: 388, NMR: 10.34 (1H, s), 6.67 (1H, dd), 3.54 (2H, t), 1.24 (6H, s) |
| 269 | 2 | 4-Cl | CH | 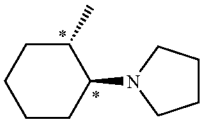 | 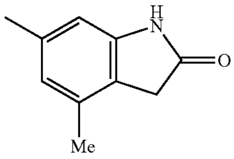 | HCl | F: 467, NMR: 10.42 (1H, s), 7.50 (1H, d), 2.17 (3H, s), 2.12-1.24 (12H, m) |
| 270 | 2 | 4-$CF_3$ | CH | 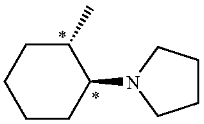 | 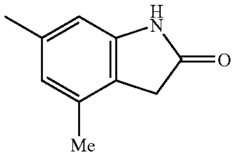 | HCl | F: 501, NMR: 10.43 (1H, s), 7.00 (1H, d), 2.18 (3H, s), 2.12-1.26 (12H, m) |
| 271 | 2 | 4-Cl | CH | 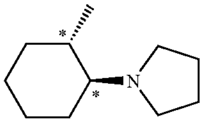 | 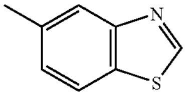 | HCl | F: 455, NMR: 10.54 (1H, s), 9.40 (1H, s), 3.98 (1H, m), 2.11-1.26 (12H, m) |
| 272 | 2 | 4-$CF_3$ | CH | 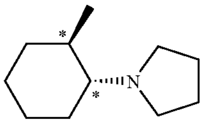 | 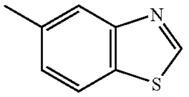 | HCl | F: 489, NMR: 10.75 (1H, s), 9.41 (1H, s), 4.09 (1H, m), 2.13-1.25 (12H, m) |
| 273 | 2 | 4-Cl | CH | 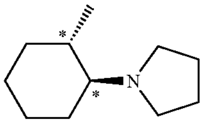 | 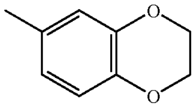 | HCl | F: 456, NMR: 10.12 (1H, s), 7.69 (1H, d), 4.24-4.20 (4H, m), 2.11-1.23 (12H, m) |
| 274 | 2 | 4-Cl | CH | 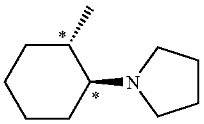 | 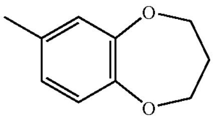 | HCl | F: 470, NMR: 10.19 (1H, s), 7.69 (1H, d), 4.12-4.06 (4H, m), 2.12-1.23 (14H, m) |

TABLE 39
| | | | | | | | |
|---|---|---|---|---|---|---|---|
| 275 | 2 | H | N | cPen | 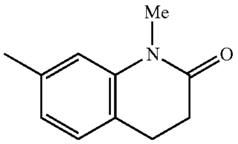 | | F: 365, NMR: 10.16 (1H, s), 7.17 (1H, d), 2.85-2.81 (2H, m), 2.03-1.37 (8H, m) |
| 276 | 2 | 4-Me | N | cHex | 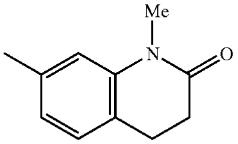 | | F: 393, NMR: 10.03 (1H, s), 7.16 (1H, d), 2.84-2.81 (2H, m), 1.95-1.20 (8H, m) |
| 277 | 2 | 4-Cl | CH | 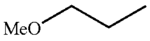 | 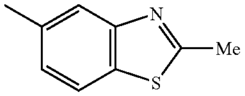 | | F: 376, NMR: 10.31 (1H, s), 6.69 (1H, dd), 3.55 (2H, t), 2.79 (3H, s) |
| 278 | 2 | 4-$CF_3$ | CH | 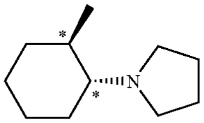 | 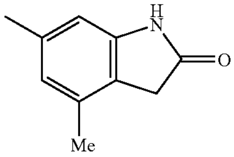 | HCl | F: 501, NMR: 10.44 (1H, s), 7.00 (1H, d), 2.18 (3H, s), 2.14-1.27 (12H, m) |
| 279 | 2 | H | N | 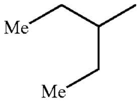 | 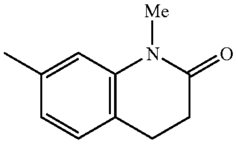 | | F: 367, NMR: 10.16 (1H, s), 7.18 (1H, d), 2.85-2.81 (2H, m), 0.87 (6H, t) |
| 280 | 2 | 4-$CF_3$ | CH | 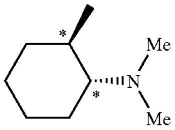 | 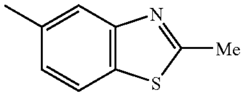 | HCl | F: 477, NMR: 10.78 (1H, s), 7.89 (1H, d), 2.80 (3H, s), 2.75 (3H, d), 2.71 (3H, d) |
| 281 | 2 | 4-$CF_3$ | CH | 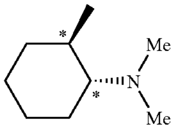 | 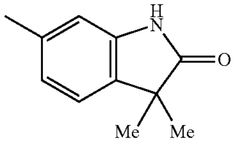 | HCl | F: 489, NMR: 10.52 (1H, s), 7.81 (1H, d), 2.80 (3H, s), 2.74 (3H, d), 2.70 (3H, d) |
| 282 | 2 | 4-$CF_3$ | CH | 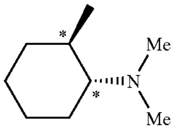 | 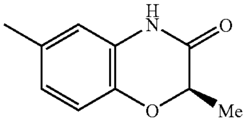 | HCl | F: 491, NMR: 10.77 (1H, s), 7.80 (1H, d), 4.62 (1H, q), 2.74 (3H, d), 2.70 (3H, d) |
| 283 | 2 | 4-Cl | CH | 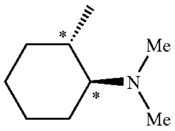 | 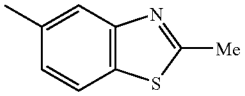 | HCl | F: 443, NMR: 10.53 (1H, s), 7.97 (1H, d), 2.79 (3H, s), 2.74 (3H, d), 2.69 (3H, d) |
| 284 | 2 | 4-Cl | CH | 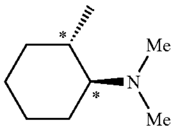 | 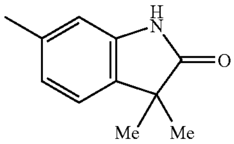 | HCl | F: 455, NMR: 10.43 (1H, s), 7.70 (1H, d), 2.73 (3H, d), 2.69 (3H, d), 1.24 (6H, s) |

TABLE 39-continued
| | | | | | | | |
|---|---|---|---|---|---|---|---|
| 285 | 2 | 4-Cl | CH | 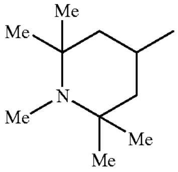 | 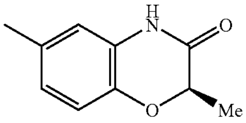 | HCl | F: 485, NMR: 10.64 (1H, s), 6.92 (1H, d), 4.62 (1H, q), 1.50 (6H, s), 1.45 (6H, s) |
| 286 | 2 | 4-Cl | CH | 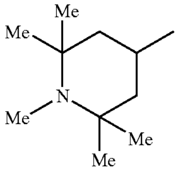 | 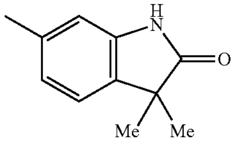 | HCl | F: 483, NMR: 10.32 (1H, s), 7.78 (1H, d), 1.51 (6H, s), 1.45 (6H, s), 1.24 (6H, s) |
| 287 | 2 | 4-$CF_3$ | CH | 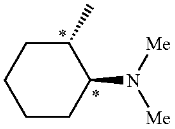 | 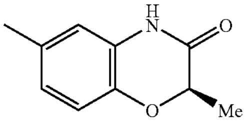 | HCl | F: 491, NMR: 10.78 (1H, s), 7.80 (1H, d), 4.62 (1H, q), 2.74 (3H, d), 2.70 (3H, d) |
TABLE 40
| | | | | | | | |
|---|---|---|---|---|---|---|---|
| 288 | 2 | 4-$CF_3$ | CH | 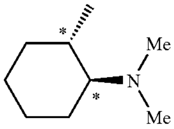 | 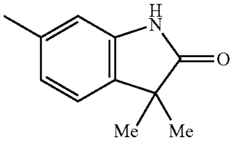 | HCl | F: 489, NMR: 10.57 (1H, s), 7.81 (1H, d), 2.74 (3H, d), 2.71 (3H, d), 1.24 (6H, s) |
| 289 | 2 | 4-Cl | CH | 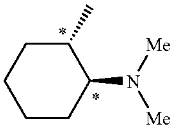 | 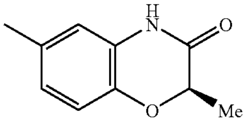 | HCl | F: 457, NMR: 10.76 (1H, s), 7.69 (1H, d), 4.61 (1H, q), 2.73 (3H, d), 2.69 (3H, d) |
| 290 | 2 | 4-$CF_3$ | CH | 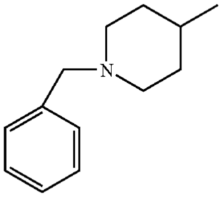 | 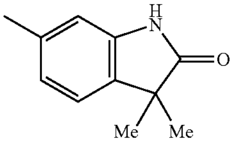 | | F: 537, NMR: 10.36 (1H, s), 6.91 (1H, d), 1.96-1.40 (4H, m), 1.25 (6H, s) |
| 291 | 2 | 4-Cl | CH | 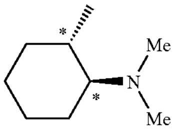 | 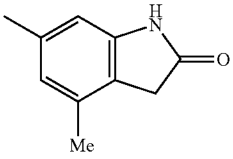 | HCl | ES: 441, NMR: 10.43 (1H, s), 7.71 (1H, d), 2.74 (3H, d), 2.69 (3H, d), 2.17 (3H, s) |
| 292 | 2 | 4-$CF_3$ | CH | 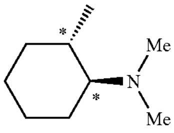 | 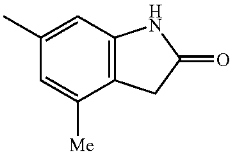 | HCl | F: 475, NMR: 10.46 (1H, s), 7.82 (1H, d), 2.74 (3H, d), 2.70 (3H, d), 2.17 (3H, s) |

TABLE 40-continued
| | | | | | | | |
|---|---|---|---|---|---|---|---|
| 293 | 2 | 4-$CF_3$ | CH | 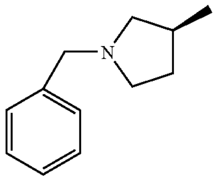 | 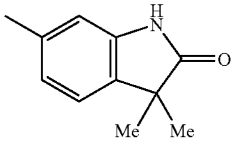 | HCl | F: 523, NMR: 10.38 (1H, s), 6.94 (1H, d), 3.64-3.57 (2H, m), 1.25 (6H, s) |
| 294 | 2 | 4-$CF_3$ | CH | cHex | 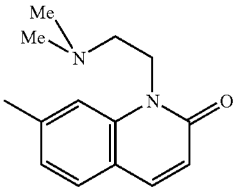 | | F: 501, NMR: 10.70 (1H, s), 7.93 (1H, d), 6.57 (1H, d), 4.58 (2H, t), 1.97-1.87 (2H, m) |
| 295 | 2 | 4-Cl | CH | 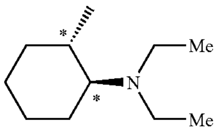 | 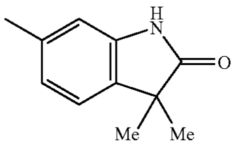 | | F: 483, NMR: 10.35 (1H, s), 7.56 (1H, d), 7.25-7.15 (2H, m), 128-1.18 (7H, m), 0.90 (6H, t) |
| 296 | 2 | 4-$CF_3$ | CH | cHex | 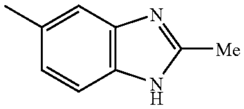 | | F: 417, NMR: 10.64 (1H, s), 7.95 (1H, d), 3.58-3.49 (1H, m), 2.80 (3H, s), 1.97-1.86 (2H, m). |
| 297 | 2 | 4-$CF_3$ | N | 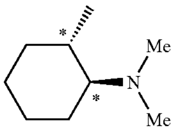 | 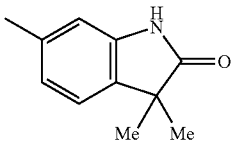 | | F: 490, NMR: 10.69 (1H, s), 7.95 (1H, d), 2.75 (3H, d), 2.71 (3H, d), 1.24 (6H, s) |
| 298 | 2 | 4-$CF_3$ | N | 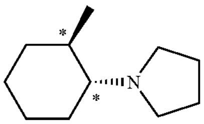 | 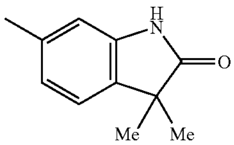 | | F: 516, NMR: 10.36 (2H, s), 8.20 (1H, d), 7.04 (1H, d), 4.10-4.00 (1H, m), 2.27-2.16 (1H, m). |
| 299 | 2 | 4-$CF_3$ | N | 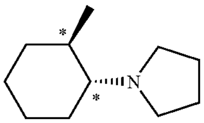 | 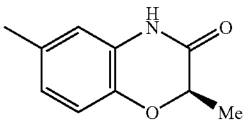 | HCl | F: 518, NMR: 10.76 (1H, s), 8.29 (1H, d), 6.95 (1H, d), 4.63 (1H, q), 4.46-4.34 (1H, m). |
TABLE 41
| | | | | | | |
|---|---|---|---|---|---|---|
| 300 | 2 | 4-$CF_3$ | N | 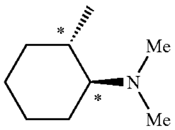 | 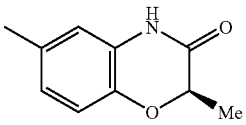 | F: 492, NMR: 10.78 (1H, s), 7.98 (1H, d), 4.63 (1H, q), 2.75 (3H, d), 2.71 (3H, d) |
| 301 | 2 | 4-$CF_3$ | N | 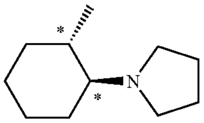 | 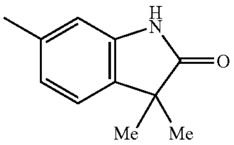 | F: 516, NMR: 10.36 (2H, s), 820 (1H, d), 7.04 (1H,d), 4.10-4.00 (1H, m), 2.27-2.16 (1H, m). |

TABLE 41-continued
| | | | | | | | |
|---|---|---|---|---|---|---|---|
| 302 | 2 | 4-$CF_3$ | N | 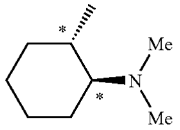 | 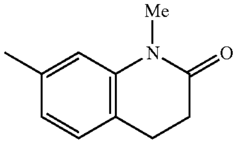 | HCl | F: 490, NMR: 10.75 (1H, s), 7.47 (1H, dd), 2.86-2.82 (2H, m), 2.74 (3H, d), 2.71 (3H, d) |
| 303 | 2 | H | N | 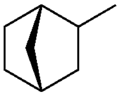 | 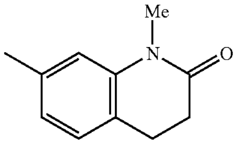 | | F: 391, NMR: 10.16 (1H, s), 7.18 (1H, d), 2.85-2.81 (2H, m), 2.28-1.11 (10H, m) |
| 304 | 2 | H | N | 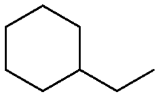 | 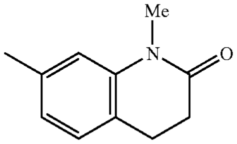 | | F: 393, NMR: 10.16 (1H, s), 7.18 (1H, d), 2.85-2.81 (2H, m), 1.74-0.92 (11H, m) |
| 305 | 2 | H | N | 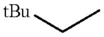 | 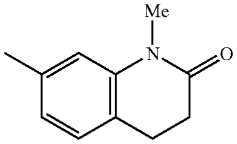 | | F: 367, NMR: 10.18 (1H, s), 7.18 (1H, d), 2.85-2.81 (2H, m), 0.93 (9H, s) |
| 306 | 2 | 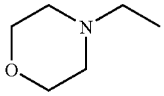 | CH | cHex | 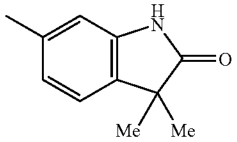 | 2HCl | F: 477, NMR 10.34 (1H, s), 7.74 (1H, d), 3.53-3.44 (1H, m), 2.00-1.90 (2H, m). |
| 307 | 97 | 4-$CF_3$ | CH | 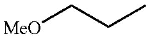 | 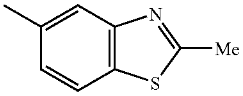 | | F: 410, NMR: 10.49 (1H, s), 6.96 (1H, d), 3.56 (2H, t), 2.80 (3H, s) |
| 308 | 97 | 4-$CF_3$ | CH | 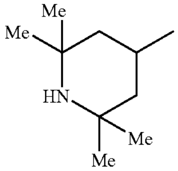 | 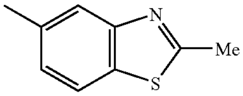 | HCl | F: 491, NMR: 10.56 (1H, s), 7.01 (1H, d), 2.80 (3H, s), 1.53 (6H, s), 1.44 (6H, s) |
| 309 | 97 | 4-$CF_3$ | CH | 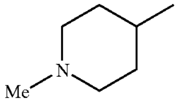 | 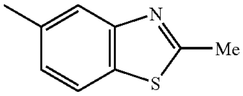 | HCl | F: 449, NMR: 10.59 (1H, s), 6.99 (1H, d), 2.81 (3H, s), 2.73 (3H, d) |
| 310 | 97 | 4-$CF_3$ | CH | 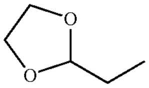 | 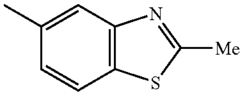 | | F: 438, NMR: 10.49 (1H, s), 7.89 (1H, d), 5.06 (1H, t), 280 (3H, s) |
| 311 | 97 | 4-$CF_3$ | CH | 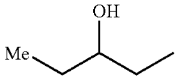 | 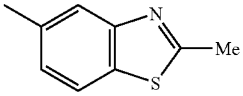 | | F: 424, NMR: 10.46 (1H, s), 7.87 (1H, d), 4.89 (1H, d), 2.80 (3H, s) |
| 312 | 97 | 4-$CF_3$ | CH | 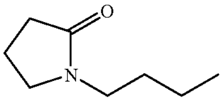 | 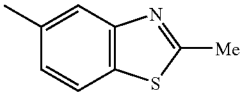 | | F: 477, NMR: 10.48 (1H, s), 7.87 (1H, d), 3.36-3.18 (6H, m), 2.80 (3H, s) |
| 313 | 97 | 4-$CF_3$ | CH | 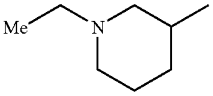 | 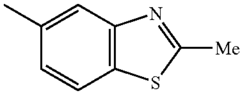 | HCl | F: 463, NMR: 10.63 (1H, s), 7.02 (1H, d), 2.81 (3H, s), 126 (3H, t) |

TABLE 42
| | | | | | | | |
|---|---|---|---|---|---|---|---|
| 314 | 97 | 4-$CF_3$ | CH | 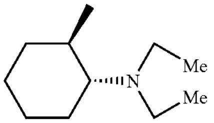 | 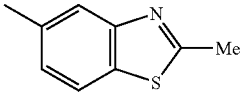 | HCl | F: 505, NMR: 10.83 (1H, s), 7.91 (1H, d), 2.80 (3H, s), 1.30 (3H, t), 1.23 (3H, t) |
| 315 | 97 | 4-$CF_3$ | CH | 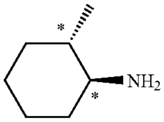 | 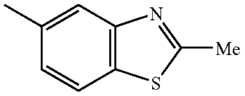 | HCl | F: 449, NMR: 10.60 (1H, s), 7.90 (1H, d), 2.80 (3H, s), 2.09-1.25 (8H, m) |
| 316 | 97 | 4-$CF_3$ | CH | 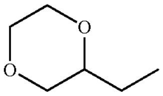 | 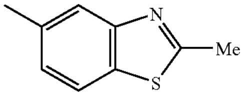 | | F: 452, NMR: 10.50 (1H, s), 7.89 (1H, d), 3.81-3.12 (9H, m), 2.80 (3H, s) |
| 317 | 97 | 4-$CF_3$ | CH | 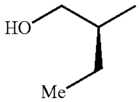 | 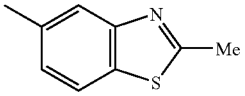 | | F: 424, NMR: 10.45 (1H, s), 7.87 (1H, d), 4.85 (1H, t), 2.80 (3H, s) |
| 318 | 97 | 4-$CF_3$ | CH | 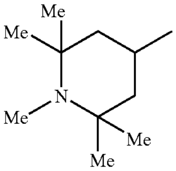 | 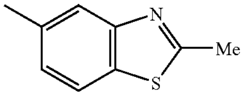 | HCl | F: 505, NMR: 10.57 (1H, s), 7.01 (1H, d), 2.80 (3H, s), 1.50 (6H, s), 1.45 (6H, s) |
| 319 | 97 | 4-$CF_3$ | CH | 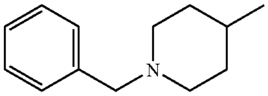 | 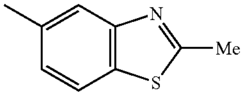 | HCl | F: 525, NMR: 10.55 (1H, s), 6.98 (1H, d), 2.80 (3H, s), 2.20-1.77 (4H, m) |
| 320 | 97 | 4-$CF_3$ | CH | 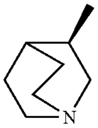 | 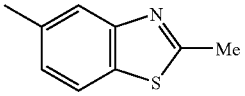 | HCl | F: 461, NMR: 10.66 (1H, s), 7.05 (1H, d), 2.80 (3H, s), 2.23-1.77 (5H, m) |
| 321 | 97 | 4-$CF_3$ | CH | 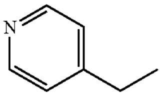 | 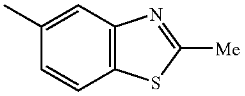 | HCl | F: 443, NMR: 10.72 (1H, s), 8.88 (2H, d), 7.78 (1H, dd), 4.91 (2H, s), 2.81 (3H, s). |
| 322 | 97 | 4-$CF_3$ | CH | 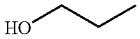 | 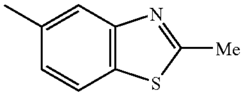 | | F: 396, NMR: 10.47 (1H, s), 7.87 (1H, d), 4.88 (1H, t), 2.80 (3H, s) |
| 323 | 97 | 4-$CF_3$ | CH | 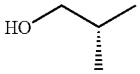 | 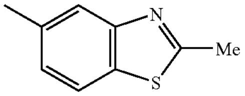 | | F: 410, NMR: 10.45 (1H, s), 7.88 (1H, d), 4.92 (1H, t), 2.80 (3H, s) |
| 324 | 100 | 4-$CF_3$ | CH | 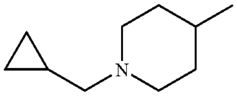 | 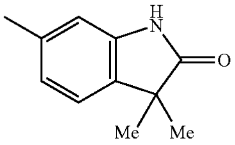 | HCl | F: 501, NMR: 10.35 (2H, s), 6.97 (1H, d), 1.25 (6H, s), 0.67-0.37 (4H, m) |
| 325 | 100 | 4-$CF_3$ | CH | 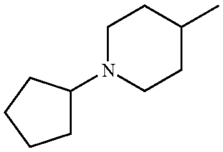 | 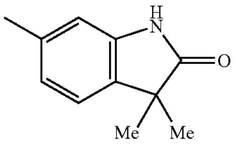 | HCl | F: 515, NMR: 10.35 (1H, s), 6.97 (1H, d), 2.17-1.52 (12H, m), 1.24 (6H, s) |

TABLE 42-continued
| | | | | | | | |
|---|---|---|---|---|---|---|---|
| 326 | 100 | 4-$CF_3$ | CH | 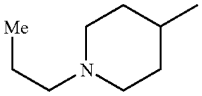 | 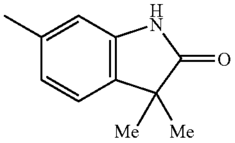 | HCl | F: 489, NMR: 10.35 (2H, s), 6.97 (1H, d), 1.24 (6H, s), 0.92 (3H, t) |
| 327 | 100 | 4-$CF_3$ | CH | 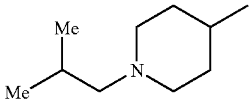 | 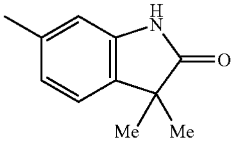 | HCl | F: 503, NMR: 10.37 (2H, s), 6.97 (1H, d), 1.24 (6H, s), 1.01 (6H, d) |
TABLE 43
| | | | | | | | |
|---|---|---|---|---|---|---|---|
| 328 | 100 | 4-$CF_3$ | CH | 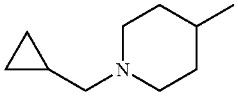 | 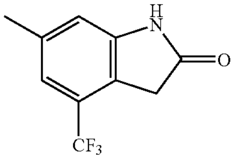 | HCl | F: 541, NMR: 10.76 (1H, s), 6.98 (1H, d), 220-1.80 (4H, m), 0.68-0.38 (4H, m) |
| 329 | 100 | 4-$CF_3$ | CH | 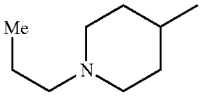 | 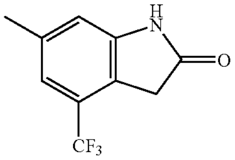 | HCl | F: 529, NMR: 10.76 (1H, s), 6.98 (1H, d), 3.61 (2H, s), 0.92 (3H, t) |
| 330 | 100 | 4-$CF_3$ | CH | 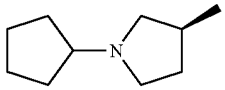 | 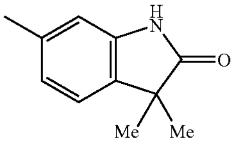 | HCl | F: 501, NMR: 10.38 (1H, s), 7.44 (1H, d), 2.02-1.49 (9H, m), 1.24 (6H, s) |
| 331 | 100 | 4-$CF_3$ | CH | 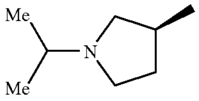 | 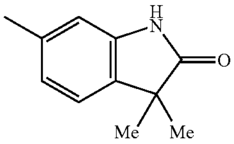 | HCl | F: 475, NMR: 10.39 (1H, s), 7.44 (1H, d), 1.29 (6H, s), 1.24 (6H, s) |
| 332 | 100 | 4-$CF_3$ | CH | 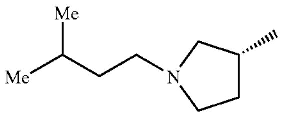 | 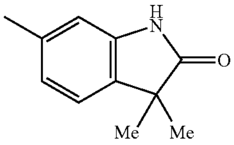 | HCl | F: 503, NMR: 10.39 (1H, s), 7.87 (1H, dd), 1.24 (6H, s), 0.89 (3H, t) |
| 333 | 100 | 4-$CF_3$ | CH | 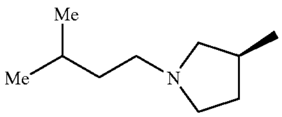 | 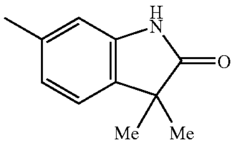 | HCl | F: 503, NMR: 10.40 (1H, s), 7.87 (1H, dd), 1.24 (6H, s), 0.89 (3H, t) |
| 334 | 100 | 4-$CF_3$ | CH | 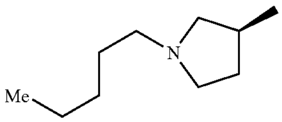 | 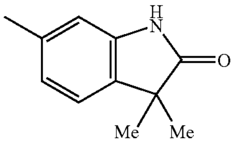 | HCl | F: 503, NMR: 10.38 (1H, s), 7.87 (1H, dd), 1.24 (6H, s), 0.90-0.85 (3H, m) |

TABLE 43-continued
| | | | | | | | |
|---|---|---|---|---|---|---|---|
| 335 | 100 | 4-$CF_3$ | CH | 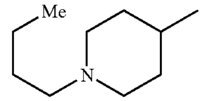 | 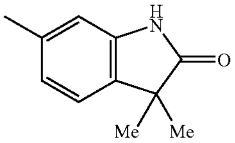 | HCl | F: 503, NMR: 10.35 (2H, s), 6.97 (1H, d), 1.24 (6H, s), 0.92 (3H, t) |
| 336 | 101 | 4-$CF_3$ | CH | 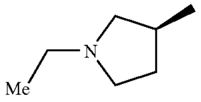 | 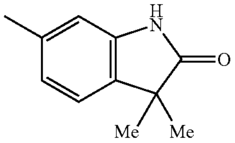 | HCl | F: 461, NMR: 10.40 (1H, s), 7.44 (1H, d), 2.00-1.80 (1H, m), 126-1.22 (9H, m) |
| 337 | 101 | 4-$CF_3$ | CH | 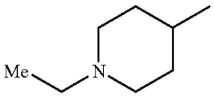 | 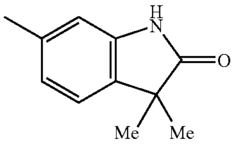 | HCl | F: 475, NMR: 10.35 (2H, s), 6.97 (1H, d), 1.27 (3H, t), 1.24 (6H, s) |
| 338 | 106 | 4-$CF_3$ | CH | 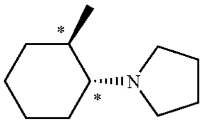 | 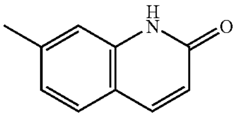 | HCl | F: 499, NMR: 11.80 (1H, s), 10.80 (1H, s), 7.10 (1H, d), 2.13-1.25 (12H, m) |
TABLE 44
| | | | | | | | |
|---|---|---|---|---|---|---|---|
| 339 | 106 | 4-$CF_3$ | CH | 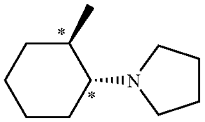 | 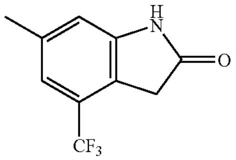 | HCl | F: 555, NMR: 10.77 (1H, s), 7.14 (1H, d), 3.61 (2H, s), 2.12-1.25 (12H, m) |
| 340 | 106 | 4-Cl | CH | 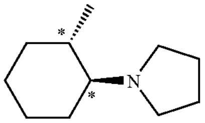 | 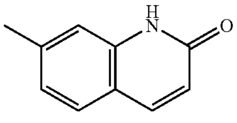 | HCl | F: 465, NMR: 11.76 (1H, s), 10.58 (1H, s), 7.36 (1H, d), 2.12-1.23 (12H, m) |
| 341 | 106 | 4-Cl | CH | 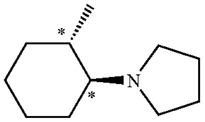 | 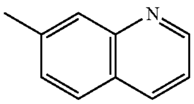 | 2HCl | ES: 449, NMR: 11.21 (1H, s), 9.14 (1H, m), 734 (1H, d), 2.12-1.27 (12H, m) |
| 342 | 106 | 4-$CF_3$ | CH | 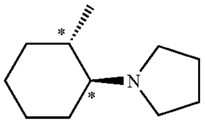 | 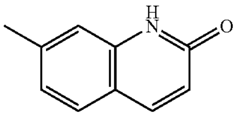 | HCl | F: 499, NMR: 11.78 (1H, s), 10.78 (1H, s), 7.11 (1H, d), 2.13-1.23 (12H, m) |
| 343 | 106 | 4-Cl | CH | 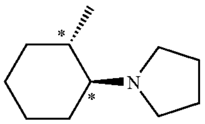 | 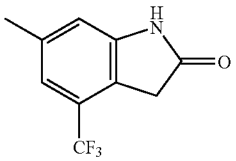 | HCl | F: 521, NMR: 10.55 (1H, s), 7.38 (1H, d), 3.60 (2H, s), 2.11-1.21 (12H, m) |
| 344 | 106 | 4-Cl | CH | 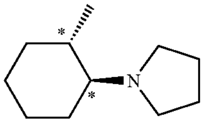 | 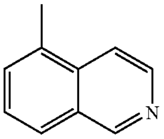 | 2HCl | ES: 449, NMR: 10.94 (1H, s), 9.89 (1H, s), 7.75 (1H, d), 2.08-1.22 (12H, m) |

TABLE 44-continued
| | | | | | | | |
|---|---|---|---|---|---|---|---|
| 345 | 106 | 4-Cl | CH | 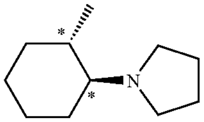 | 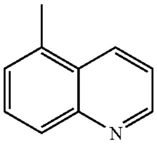 | 2HCl | ES: 449, NMR: 10.98 (1H, s), 7.73 (1H, d), 4.03 (1H, m), 2.09-1.22 (12H, m) |
| 346 | 106 | 4-Cl | CH | 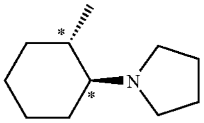 | 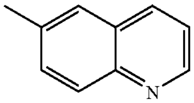 | 2HCl | ES: 449, NMR: 10.97 (1H, s), 7.43 (1H, d), 4.03 (1H, m), 2.12-127 (12H, m) |
| 347 | 106 | 4-$CF_3$ | CH | 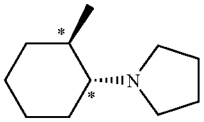 | 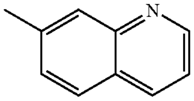 | 2HCl | ES: 483, NMR: 11.43 (1H, s), 10.22 (1H, s), 8.96 (1H, s), 8.35-8.24 (2H, m), 4.18-4.07 (1H, m), 2.13-1.29 (12H, m) |
| 348 | 106 | 4-F | N | cHex | 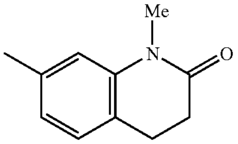 | | F: 397, NMR: 10.11 (1H, s), 8.30 (1H, t), 3.89-3.78 (1H, m), 2.83 (2H, t), 1.95-1.85 (2H,m). |
| 349 | 106 | 4-Cl | N | cHex | 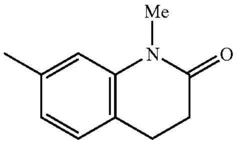 | | F: 413, NMR: 10.20 (1H, s), 8.12 (1H, d), 3.95-3.83 (1H, m), 2.83 (2H, t), 1.96-1.86 (2H, m). |
| 350 | 106 | 4-MeO | N | cHex | 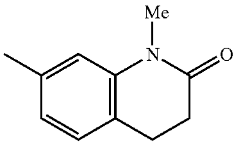 | | F: 409, NMR: 9.83 (1H, s), 6.01 (1H, d), 3.84 (3H, s), 324 (3H, s), 2.03-1.91 (2H, m). |
| 351 | 106 | 4-Cl | CH | 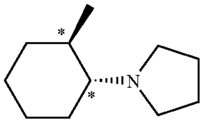 | 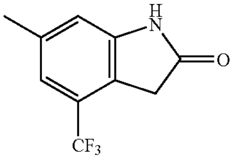 | HCl | F: 521, NMR: 10.53 (1H, s), 7.38 (1H, d), 3.60 (2H, s), 2.11-1.23 (12H, m) |
TABLE 45
| | | | | | | | |
|---|---|---|---|---|---|---|---|
| 352 | 106 | 4-Cl | CH | 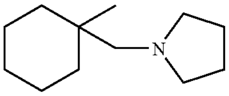 | 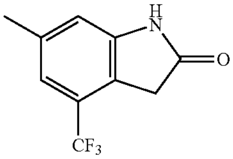 | HCl | F: 535, NMR: 6.94 (1H, s), 6.83 (1H, d), 3.05 (2H, bs), 2.08 (2H, s) |
| 353 | 106 | 4-Cl | CH | 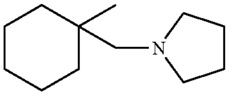 | 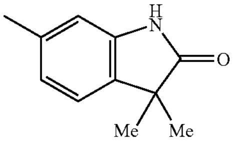 | HCl | F: 495, NMR: 7.75 (1H, d), 6.79 (1H, d), 3.04 (2H, bs), 1.24 (6H, s) |

TABLE 45-continued
| | | | | | | | |
|---|---|---|---|---|---|---|---|
| 354 | 106 | 4-$CF_3$ | CH | 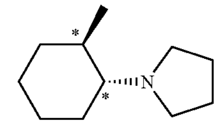 | 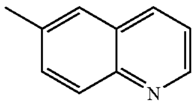 | 2HCl | ES: 483, NMR: 11.31 (1H, s), 7.19 (1H, d), 4.15 (1H, m), 2.15-1.28 (12H, m) |
| 355 | 106 | 4-Cl | CH | 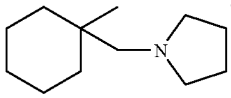 | 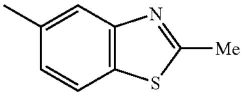 | 2HCl | F: 483, NMR: 7.98 (1H, d), 6.94 (1H, d), 3.05 (2H, bs), 2.80 (3H, s) |
| 356 | 106 | 4-Cl | CH | 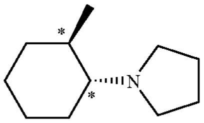 | 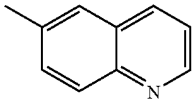 | 2HCl | ES: 449, NMR: 10.98 (1H, s), 7.43 (1H, d), 4.03 (1H, m), 2.13-1.27 (12H, m) |
| 357 | 106 | 4-Cl | CH | 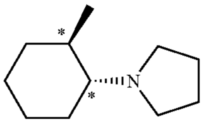 | 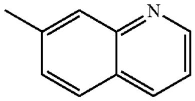 | 2HCl | ES: 449, NMR: 11.25 (1H, s), 9.15 (1H, m), 7.34 (1H, d), 2.14-1.27 (12H, m) |
| 358 | 106 | 4-Cl, 5-Cl | CH | 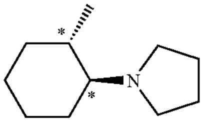 | 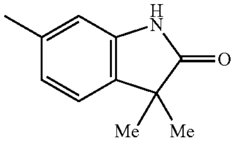 | HCl | F: 515, NMR: 7.92 (1H, s), 7.31 (1H, s), 3.98-3.96 (1H, m), 1.24 (6H, s) |
| 359 | 106 | 4-Cl, 5-Cl | CH | 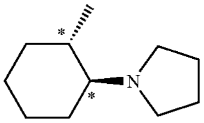 | 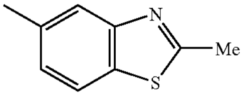 | HCl | F: 503, NMR: 7.99 (2H, s), 7.33 (1H, s), 4.00-3.98 (1H, m), 2.80 (3H, s) |
| 360 | 106 | 4-$CF_3$ | CH | 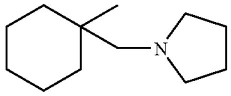 | 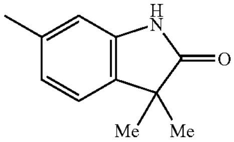 | HCl | F: 529, NMR: 7.90 (1H, d), 7.04 (1H, s), 3.05 (2H, bs), 1.24 (6H, s) |
| 361 | 106 | 4-$CF_3$ | CH | 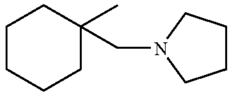 | 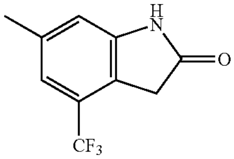 | HCl | F: 569, NMR: 7.96 (1H, d), 7.05 (1H, s), 3.06 (2H, bs), 2.20-2.17 (2H, m) |
| 362 | 106 | 4-$CF_3$ | CH | 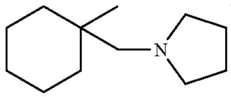 | 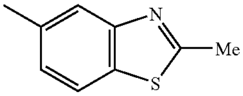 | 2HCl | F: 517, NMR: 8.37 (1H, d), 7.12 (1H, d), 3.07 (2H, bs), 2.80 (3H, s) |
| 363 | 106 | 4-$CF_3$ | CH | 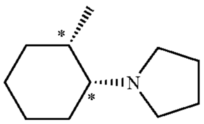 | 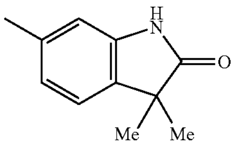 | HCl | F: 515, NMR: 7.45 (1H, s), 7.06 (1H, d), 3.53 (1H, bs), 1.25 (6H, s) |
| 364 | 106 | 4-$CF_3$ | CH | 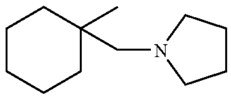 | 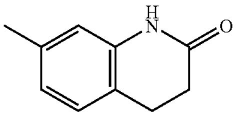 | HCl | F: 515, NMR: 7.89 (1H, d), 7.09 (1H, d), 3.05 (2H, bs), 2.84 (2H, t) |

TABLE 45-continued
| | | | | | | | |
|---|---|---|---|---|---|---|---|
| 365 | 106 | 4-Cl, 5-Me | CH | 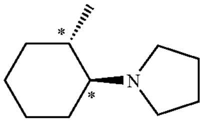 | 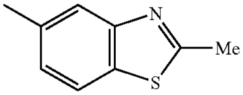 | 2HCl | F: 483, NMR: 8.34 (1H, d), 7.97 (1H, d), 3.91-3.90 (1H, m) 2.80 (3H, s) |
TABLE 46
| | | | | | | | |
|---|---|---|---|---|---|---|---|
| 366 | 106 | 4-$CF_3$ | CH | 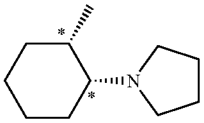 | 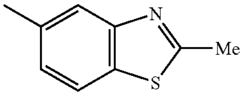 | 2HCl | F: 503, NMR: 8.03-8.00 (3H, m), 7.08 (1H, d), 2.80 (3H, s), 2.26-2.24 )2H, m) |
| 367 | 106 | 4-$CF_3$ | CH | 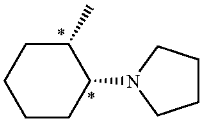 | 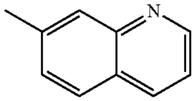 | 2HCl | F: 483, NMR: 8.27 (1H, d), 7.32 (1H, s), 7.08 (1H, d), 3.13-3.09 (1H, m) |
| 368 | 106 | 4-$CF_3$ | CH | 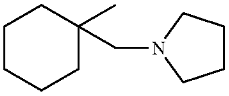 | 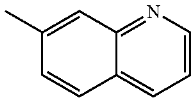 | 2HCl | F: 497, NMR: 8.23 (1H, d), 7.45 (1H, s), 7.14 (1H, d), 3.05 (2H, bs) |
| 369 | 106 | 4-$CF_3$ | CH | 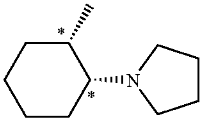 | 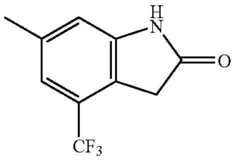 | HCl | F: 555, NMR: 7.97 (1H, d), 7.30 (1H, s), 3.13-3.09 (1H, m), 2.13-2.10 (1H, m) |
| 370 | 106 | H | N | 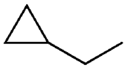 | 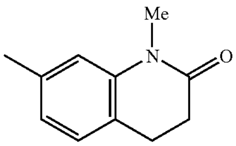 | HCl | F: 351, NMR: 8.52 (1H, d), 7.21 (1H, d), 2.85 (2H, t), 0.35-0.31 (2H, m) |
| 371 | 106 | 4-Cl | CH | 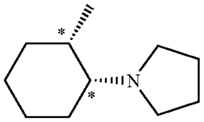 | 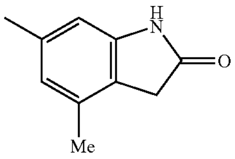 | HCl | F: 467, NMR: 7.24 (1H, s), 6.78 (1H, dd), 3.54 (1H, bs), 2.18 (2H, s) |
| 372 | 106 | 4-Cl | CH | 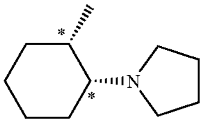 | 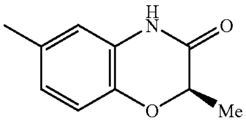 | HCl | F: 483, NMR: 7.77 (1H, d), 6.95 (1H, d), 4.62 (1H, q), 3.53 (1H, bs) |
| 373 | 106 | 4-$CF_3$ | CH | 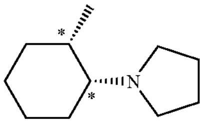 | 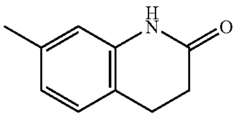 | HCl | F: 501, NMR: 7.33 (1H, d), 7.04 (1H, d), 3.52 (1H, bs), 2.84 (2H, t) |
| 374 | 106 | 4-Cl, 5-Cl | CH | 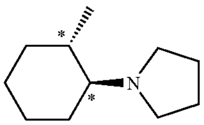 | 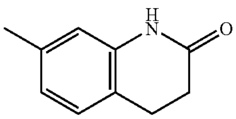 | HCl | F: 501, NMR: 7.31 (1H, s), 7.12 (1H, d), 3.97-3.96 (1H, m), 2.84 (2H, t) |

TABLE 46-continued
| | | | | | | | |
|---|---|---|---|---|---|---|---|
| 375 | 106 | 4-Cl | CH | 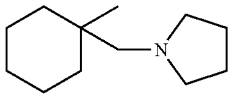 | 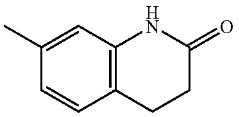 | HCl | F: 481, NMR: 7.32 (1H, d), 6.79 (1H, dd), 3.04 (2H, bs), 2.83 (2H, t) |
| 376 | 106 | 4-$CF_3$ | CH | 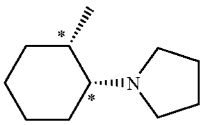 | 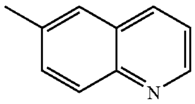 | 2HCl | F: 483, NMR: 8.05 (1H, d), 7.31 (1H, s), 7.08 (1H, d), 3.54 (1H, bs) |
| 377 | 106 | 4-Cl | CH | 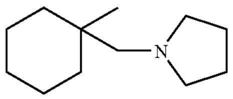 | 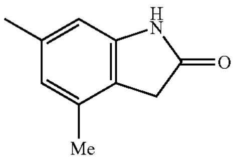 | HCl | F: 481, NMR: 7.74 (1H, d), 6.80 (1H, dd), 3.05 (2H, bs), 1.34-1.31 (1H, m) |
| 378 | 106 | 4-$CF_3$ | CH | 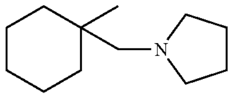 | 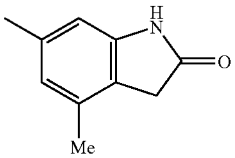 | HCl | F: 515, NMR: 7.89 (1H, d), 7.26 (1H, s), 3.05 (2H, bs), 1.94-1.89 (4H, m) |
TABLE 47
| | | | | | | | |
|---|---|---|---|---|---|---|---|
| 379 | 106 | 4-Cl | CH | 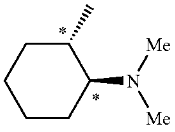 | 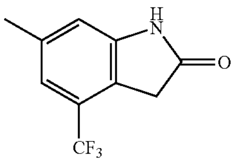 | HCl | F: 495, NMR 10.89 (1H, s), 6.76 (1H, dd), 3.60 (2H, s), 2.74 (3H, d), 2.68 (3H, d) |
| 380 | 106 | 4-$CF_3$ | CH | 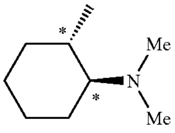 | 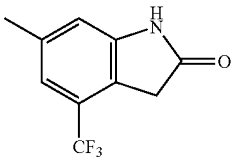 | HCl | F: 529, NMR: 10.89 (1H, s), 6.94 (1H, d), 3.60 (2H, s), 2.74 (3H, d), 2.69 (3H, d) |
| 381 | 106 | 4-$CF_3$ | CH | 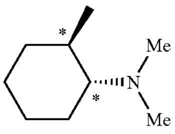 | 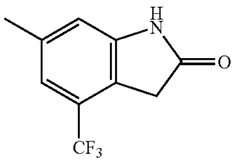 | | F: 529, NMR: 10.89 (1H, s), 6.94 (1H, d), 3.61 (2H, s), 2.74 (3H, d), 2.69 (3H, d) |
| 382 | 106 | 4-$CF_3$ | CH | 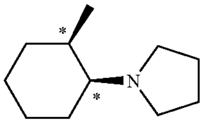 | 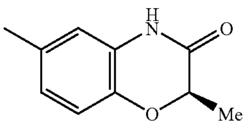 | HCl | F: 517, NMR: 10.76 (1H, s), 7.96-7.87 (2H, m), 6.96 (1H, d), 4.63 (1H, q), 2.14-1.72 (7H, m). |
| 383 | 106 | 4-$CF_3$ | CH | 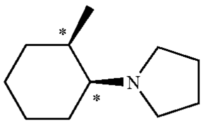 | 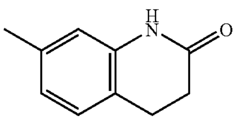 | HCl | F: 501, NMR: 7.32 (1H, d), 7.05 (1H, d), 3.53 (1H, bs), 2.84 (2H, t) |

TABLE 47-continued
| | | | | | | | |
|---|---|---|---|---|---|---|---|
| 384 | 106 | 4-$CF_3$ | CH | 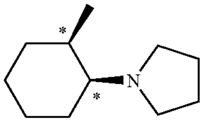 | 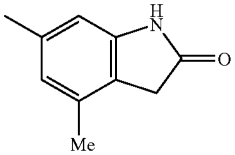 | HCl | F: 501, NMR: 7.29 (1H, s), 7.27 (1H, d), 3.54 (1H, bs), 2.19 (3H, s) |
| 385 | 106 | 4-$CF_3$ | N | 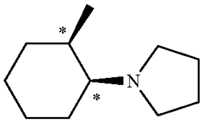 | 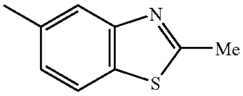 | HCl | F: 504, NMR: 8.02 (1H, d), 7.22 (1H, d), 3.26-321 (1H, m), 2.87 (3H, s) |
| 386 | 106 | 4-$CF_3$ | CH | 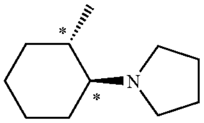 | 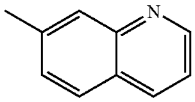 | 2HCl | F: 483, NMR: 11.46 (1H, s), 8.97 (1H, s), 4.13 (1H, m), 2.14-1.29 (12H, m) |
| 387 | 106 | 4-$CF_3$ | CH | 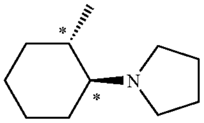 | 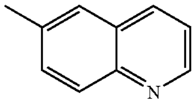 | 2HCl | F: 483, NMR: 11.26 (1H, s), 9.02 (1H, s), 4.14 (1H, m), 2.14-1.28 (12H, m) |
| 388 | 106 | 4-$CF_3$ | N | 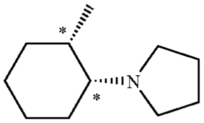 | 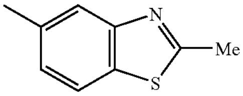 | HCl | F: 504, NMR: 8.36 (1H, d), 7.76 (1H, dd), 3.26-3.21 (1H, m), 2.81 (3H, s) |
| 389 | 106 | 4-$CF_3$ | CH | 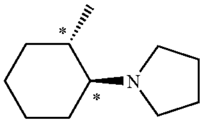 | 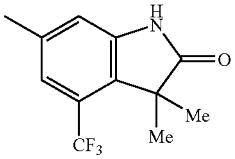 | Fum | F: 583, NMR: 10.85 (1H, s), 7.84 (1H, d), 7.05 (1H, s), 2.82-2.61 (4H, m), 1.34 (6H, s). |
| 390 | 106 | 4-Cl | CH | 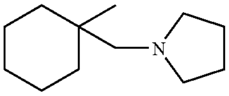 | 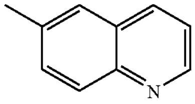 | 2HCl | F: 463, NMR: 8.69 (1H, s), 7.73 (1H, s), 6.85 (1H, dd), 3.04 (2H, bs) |
| 391 | 106 | 4-Cl | CH | 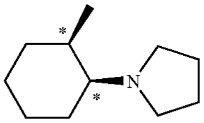 | 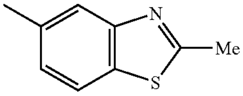 | 2HCl | ES: 469, NMR: 8.19 (1H, d), 7.15 (1H, d), 3.53 (1H, bs), 2.80 (3H, s) |
TABLE 48
| | | | | | | | |
|---|---|---|---|---|---|---|---|
| 392 | 106 | 4-$CF_3$ | CH | 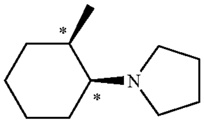 | 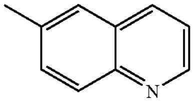 | 2HCl | F: 483, NMR: 8.66 (1H, s), 8.05 (1H, d), 7.32 (1H, s), 2.11-2.09 (1H, m) |
| 393 | 106 | 4-Cl | CH | 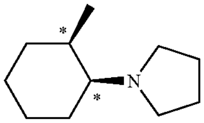 | 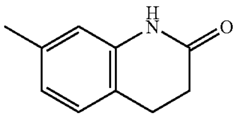 | HCl | ES: 467, NMR: 7.78 (1H, d), 6.78 (1H, dd), 3.52 (1H, bs), 2.84 (2H, t) |

TABLE 48-continued
| | | | | | | | |
|---|---|---|---|---|---|---|---|
| 394 | 106 | 4-Cl | CH | 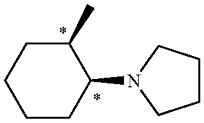 | 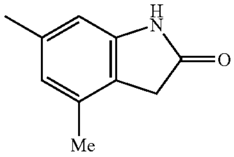 | HCl | F: 467, NMR: 8.08 (1H, d), 7.02 (1H, s), 3.54 (1H, bs), 2.18 (3H, s) |
| 395 | 106 | 4-Cl | CH | 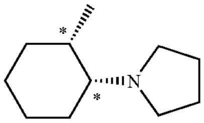 | 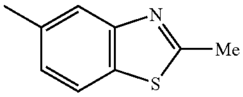 | 2HCl | F: 469, NMR: 7.99 (1H, d), 6.80 (1H, dd), 3.53 (1H, bs), 2.80 (3H, s) |
| 396 | 106 | 4-Cl | CH | 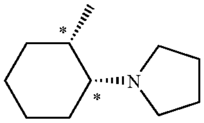 | 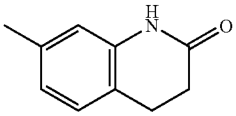 | HCl | F: 467, NMR: 8.10 (1H, d), 6.78 (1H, dd), 3.52 (1H, bs), 2.84 (2H, t) |
| 397 | 106 | 4-Cl | CH | 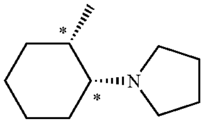 | 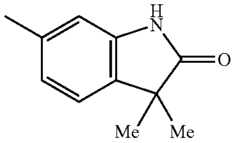 | HCl | F: 481, NMR: 10.38 (1H, s), 7.78 (1H, d), 4.47 (1H, d), 2.14-1.72 (7H, m), 1.24 (6H, s). |
| 398 | 106 | 4-$CF_3$ | CH | 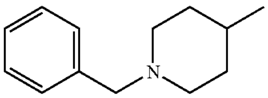 | 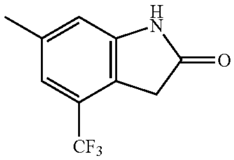 | | F: 577, NMR: 10.76 (1H, s), 7.89 (1H, d), 3.61 (2H, s), 1.95-1.41 (4H, m) |
| 399 | 106 | 4-$CF_3$ | CH | 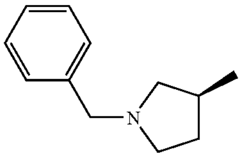 | 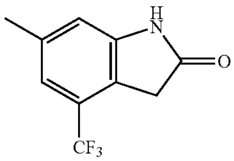 | | F: 563, NMR: 10.76 (1H, s), 7.89 (1H, d), 3.66-3.58 (4H, m), 1.58 (1H, m) |
| 400 | 106 | 5-Cl | N | 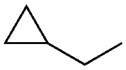 | 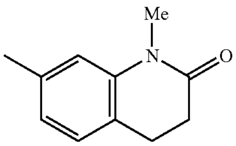 | HCl | F: 385, NMR: 8.23-8.21 (2H, m), 7.19 (1H, d), 2.84 (2H, t), 0.48-0.43 (2H, m) |
| 401 | 106 | 4-Cl | CH | 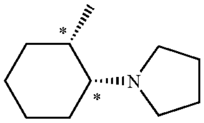 | 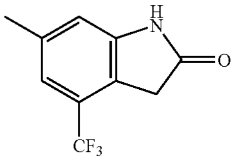 | HCl | F: 521, NMR: 8.01 (1H, d), 7.14 (1H, d), 3.55 (1H, bs), 2.12-2.09 (1H, m) |
| 402 | 107 | 4-$CF_3$ | CH | 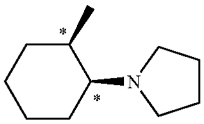 | 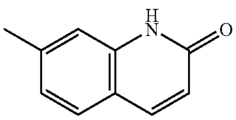 | HCl | F: 499, NMR: 7.97 (1H, d), 7.63 (1H, d), 7.30 (1H, s), 3.54 (1H, bs) |
| 403 | 107 | 4-$CF_3$ | N | 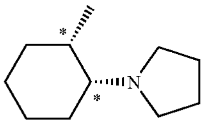 | 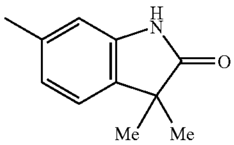 | HCl | F: 516, NMR: 8.82 (1H, d), 7.42 (1H, d), 3.65 (1H, bs), 1.25 (6H, s) |

TABLE 48-continued
| | | | | | | | |
|---|---|---|---|---|---|---|---|
| 404 | 107 | 4-Cl | CH | 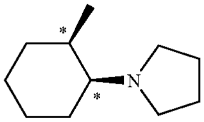 | 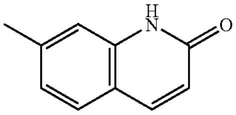 | HCl | ES: 465, NMR: 8.03 (1H, d), 7.15 (1H, s), 6.39 (1H, d), 3.55 (1H, bs) |
TABLE 49
| | | | | | | | |
|---|---|---|---|---|---|---|---|
| 405 | 107 | 4-$CF_3$ | N | 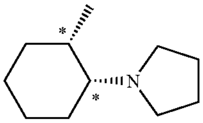 | 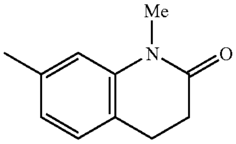 | HCl | F: 516, NMR: 8.84 (1H, d), 7.48 (1H, dd), 3.10-3.05 (1H, m), 2.85 (2H, t) |
| 406 | 107 | 4-Cl | CH | 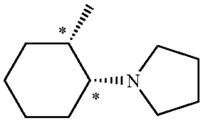 | 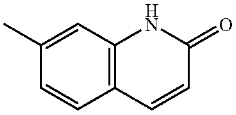 | HCl | F: 465, NMR: 8.02 (1H, d), 7.14 (1H, d), 6.81 (1H, dd), 3.54 (1H, bs) |
| 407 | 107 | 4-$CF_3$ | N | 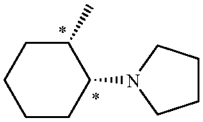 | 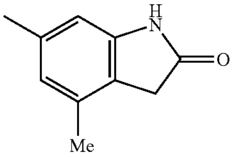 | HCl | F: 502, NMR: 8.82 (1H, d), 7.06 (1H, s), 3.52 (1H, bs), 2.18 (3H, s) |
| 408 | 107 | 4-$CF_3$ | N | 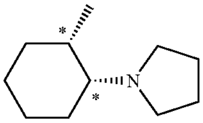 | 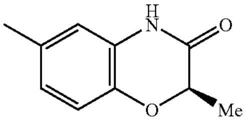 | HCl | F: 518, NMR: 8.83 (1H, d), 6.97 (1H, d), 4.64 (1H, q), 3.52 (1H, bs) |
| 409 | 107 | 4-$CF_3$ | N | 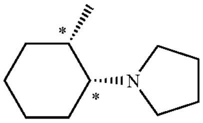 | 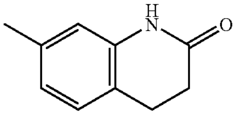 | HCl | F: 502, NMR: 8.43 (1H, d), 7.31 (1H, d), 3.10-3.05 (1H, m), 2.85 (2H, t) |
| 410 | 107 | 4-$CF_3$ | N | 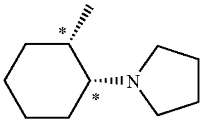 | 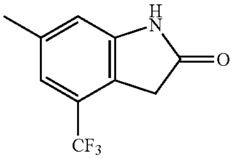 | HCl | F: 556, NMR: 8.69 (1H, d), 7.61 (1H, s), 3.25-3.21 (1H, m), 3.10-3.06 (1H, m) |
| 411 | 107 | 4-$CF_3$ | N | 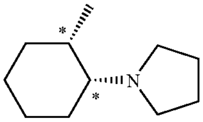 | 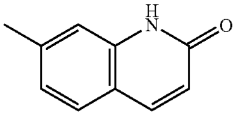 | HCl | F: 500, NMR: 8.48 (1H, d), 7.65 (1H, d), 6.41 (1H, dd), 3.26-3.21 (1H, m) |
| 412 | 107 | 4-$CF_3$ | N | 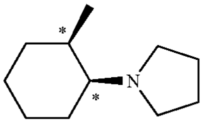 | 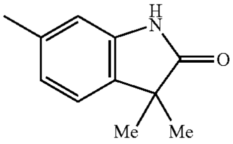 | HCl | F: 516, NMR: 8.81 (1H, d), 7.43 (1H, s), 3.25-3.21 (1H, m), 1.25 (3H, s) |
| 413 | 107 | 4-$CF_3$ | N | 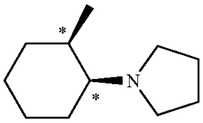 | 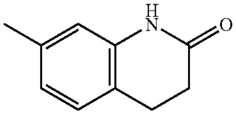 | HCl | F: 502, NMR: 8.43 (1H, d), 7.31 (1H, d), 3.52 (1H, bs), 2.85 (2H, t) |

TABLE 49-continued
| | | | | | | | |
|---|---|---|---|---|---|---|---|
| 414 | 107 | 4-Cl | CH | 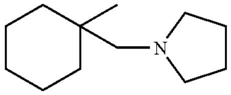 | 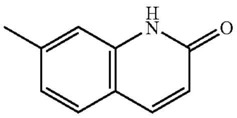 | HCl | F: 479, NMR: 7.89 (1H, d), 6.94 (1H, d), 6.39 (1H, dd), 3.05 (2H, bs) |
| 415 | 107 | 4-$CF_3$ | CH | 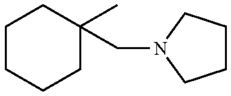 | 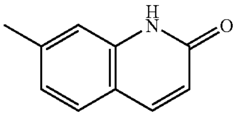 | HCl | F: 513, NMR 7.84 (1H, d), 7.06 (1H, s), 640 (1H, dd), 3.06 (2H, bs) |
| 416 | 107 | 4-$OCH_2$—$CF_3$ | N | 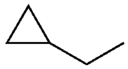 | 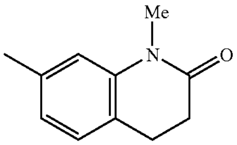 | | F: 449, NMR: 8.70 (1H, t), 6.16 (1H, d), 5.01 (2H, q), 0.27-0.23 (2H, m) |
| 417 | 107 | 4-Cl | N | 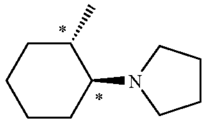 | 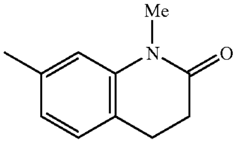 | HCl | F: 482, NMR: 10.38 (1H, s), 7.78 (1H, d), 4.47 (1H, d), 2.14-1.72 (7H, m), 1.24 (6H, s). |
TABLE 50
| | | | | | | | |
|---|---|---|---|---|---|---|---|
| 418 | 107 | 4-$CF_3$ | N | 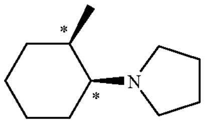 | 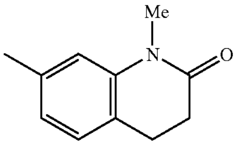 | HCl | F: 516, NMR: 8.84 (1H, d), 7.41 (1H, s), 3.53 (1H, bs), 2.85 (2H, t) |
| 419 | 107 | 5-Cl | N | 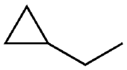 | 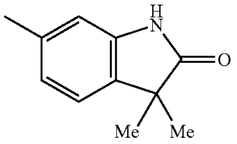 | HCl | F: 385, NMR: 8.22 (2H, s), 7.42 (1H, s), 1.24 (6H, s), 0.49-0.45 (2H, m) |
| 420 | 107 | 4-$CF_3$ | N | 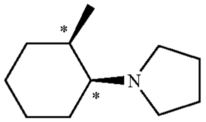 | 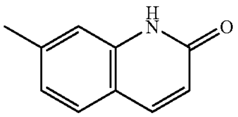 | HCl | F: 500, NMR: 8.74 (1H, d), 7.65 (1H, d), 6.41 (1H, dd), 3.26-321 (1H, m) |
| 421 | 107 | H | N | 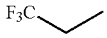 | 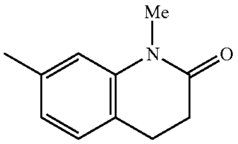 | HCl | F: 379, NMR: 8.39 (1H, t), 7.19 (1H, d), 4.43-4.34 (2H, m), 2.84 (2H, t) |
| 422 | 112 | 4-Cl | CH | 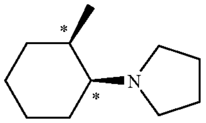 | 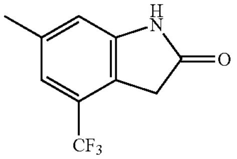 | HCl | F: 521, NMR: 10.77 (1H, s), 7.82 (1H, d), 4.53-4.44 (1H, m), 1.57-1.27 (5H, m). |
| 423 | 112 | 4-Cl | CH | 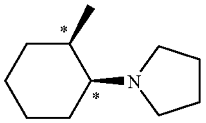 | 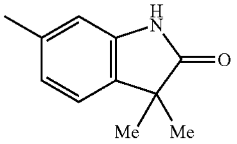 | HCl | F: 481, NMR: 10.38 (1H, s), 7.78 (1H, d), 4.53-4.41 (1H, m), 1.24 (6H, s). |

TABLE 50-continued
| | | | | | | | |
|---|---|---|---|---|---|---|---|
| 424 | 112 | 4-$CF_3$ | CH | 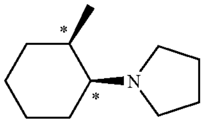 | 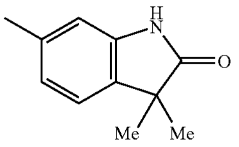 | HCl | F: 515, NMR: 10.49 (1H, s), 7.46 (1H, s), 7.05 (1H, d), 4.65-4.52 (1H, m), 1.25 (6H, s). |
| 425 | 112 | 4-$CF_3$ | CH | 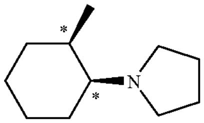 | 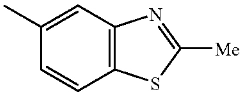 | HCl | F: 503, NMR: 10.72 (1H, s), 8.37 (1H, d), 4.59 (1H, d), 3.59-3.48 (1H, m), 3.30-3.18 (1H, m). |
| 426 | 112 | 4-$CF_3$ | CH | 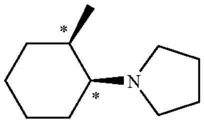 | 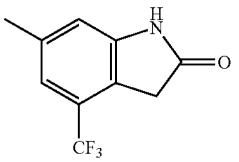 | HCl | F: 555, NMR: 10.79 (1H, s), 7.97 (1H, d), 7.07 (1H, d), 4.65-4.53 (1H, m), 3.62 (2H, s). |
| 427 | 113 | 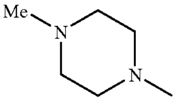 | N | cHex | 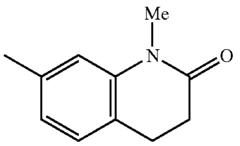 | HCl | F: 477, NMR 9.71 (1H, s), 8.07 (1H, d), 6.17 (1H, d), 3.95-3.84 (1H, m), 2.85-2.76 (5H, m). |
| 428 | 113 | 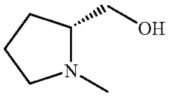 | N | cHex | 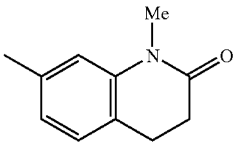 | | F: 478, NMR 9.54 (1H, s), 7.92 (1H, d), 5.76 (1H, d), 2.81 (2H, t), 1.74-1.62 (2H, m). |
TABLE 51
| Ex | Syn | Str | Dat |
|---|---|---|---|
| 429 | 2 | 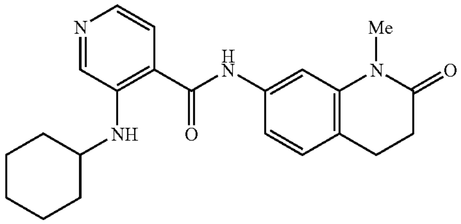 | F: 379, NMR: 10.30 (1H, s), 825 (1H, s), 3.24 (3H, s), 2.86-2.52 (4H, m), 1.98-1.19 (10H, m) |
| 430 | 2 | 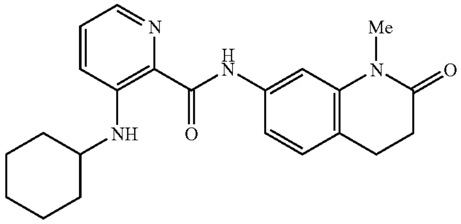 | F: 379, NMR: 10.54 (1H, s), 8.34 (1H, d), 7.62-7.54 (2H, m), 3.53-3.42 (1H, m), 3.26 (3H, s). |

TABLE 52
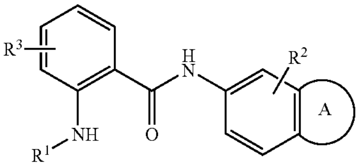
| No | $R^3$ | $R^1$ | 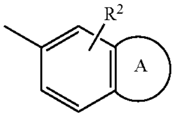 |
|---|---|---|---|
| 1 | 4-Cl | 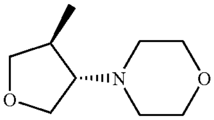 | 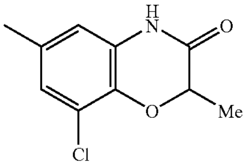 |
| 2 | 4-Cl | 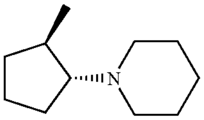 | 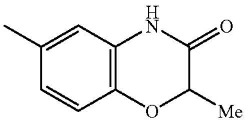 |
| 3 | 4-Cl | 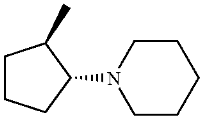 | 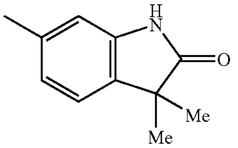 |
| 4 | 4-Cl | 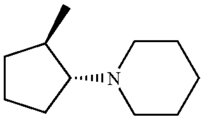 | 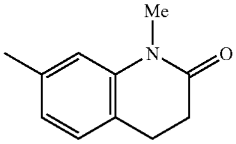 |
| 5 | 4-Cl | 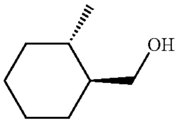 | 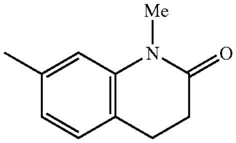 |
| 6 | 4-Cl | 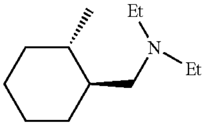 | 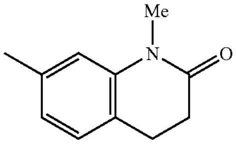 |
| 7 | 4-Cl | 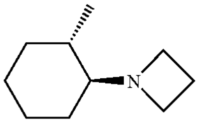 | 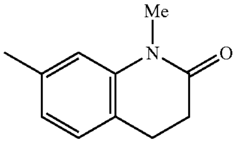 |
| 8 | 4-Cl | 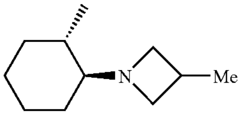 | 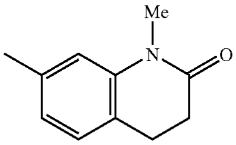 |
TABLE 52-continued
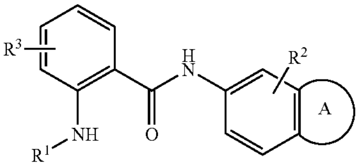
| No | $R^3$ | $R^1$ | 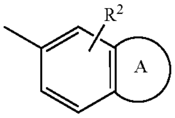 |
|---|---|---|---|
| 9 | 4-Cl | 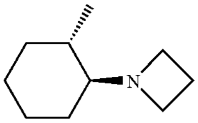 | 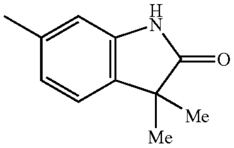 |
| 10 | 4-Cl | 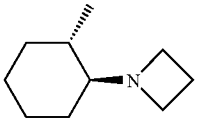 | 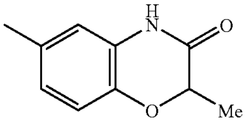 |
TABLE 53
| | | | |
|---|---|---|---|
| 11 | 4-$CF_3$ | 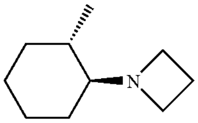 | 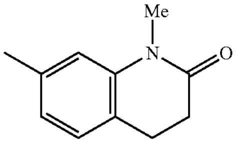 |
| 12 | 4-$CF_3$ | 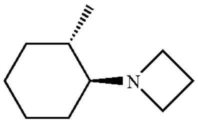 | 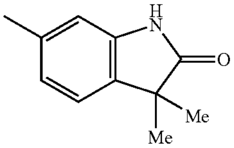 |
| 13 | 4-$CF_3$ | 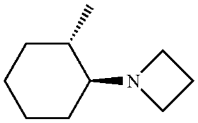 | 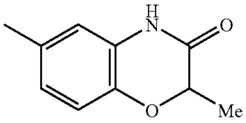 |
| 14 | 4-$CF_3$ | 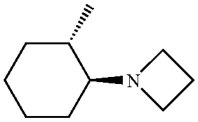 | 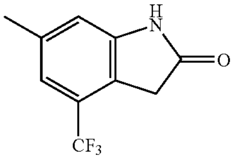 |
| 15 | 4-$CF_3$ | 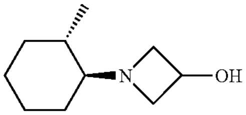 | 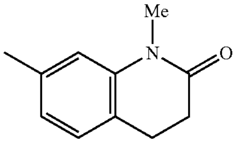 |
| 16 | H | 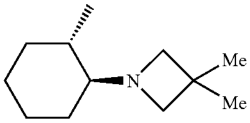 | 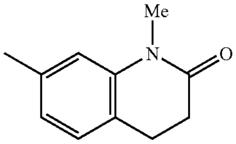 |

TABLE 53-continued
| | | | |
|---|---|---|---|
| 17 | 4-Me | 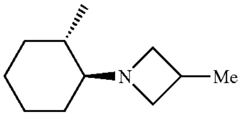 | 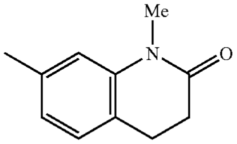 |
| 18 | 4-Cl | 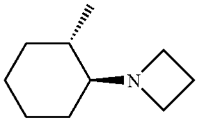 | 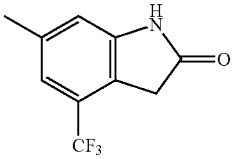 |
| 19 | 4-Cl | 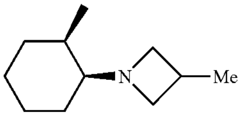 | 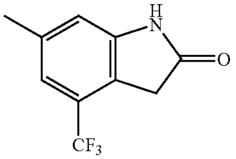 |
| 20 | 4-$CF_3$ | 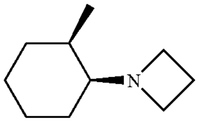 | 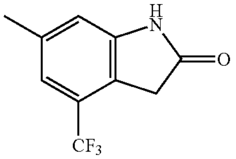 |
| 21 | 4-$CF_3$ | 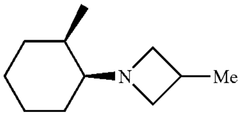 | 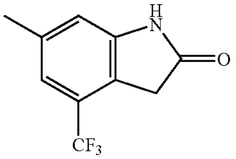 |
| 22 | 4-Cl | 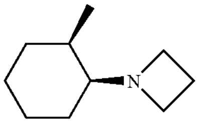 | 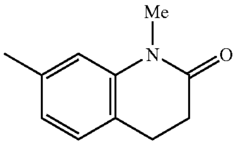 |
| 23 | 4-Cl | 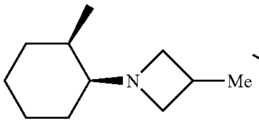 | 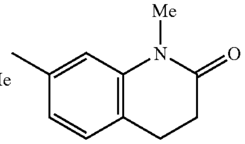 |
| 24 | 4-$CF_3$ | 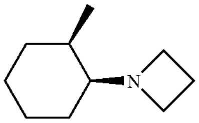 | 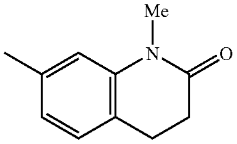 |
| 25 | 4-$CF_3$ | 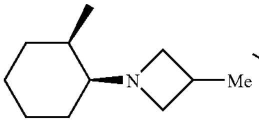 | 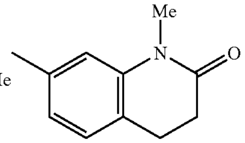 |
TABLE 53-continued
| | | | |
|---|---|---|---|
| 26 | 4-Cl | 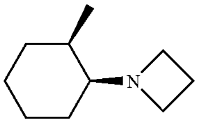 | 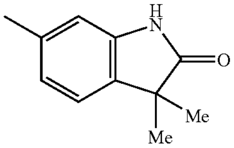 |
| 27 | 4-Cl | 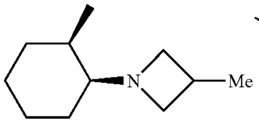 | 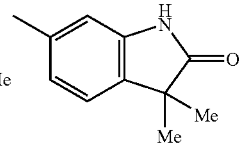 |
| 28 | 4-$CF_3$ | 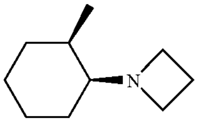 | 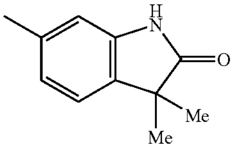 |
| 29 | 4-$CF_3$ | 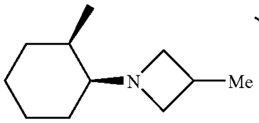 | 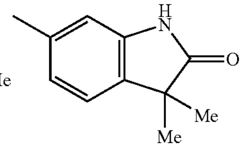 |
| 30 | 4-Cl | 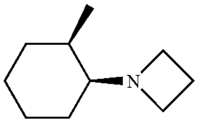 | 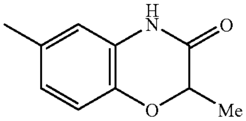 |
| 31 | 4-Cl | 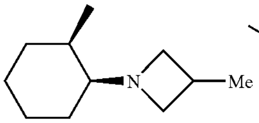 | 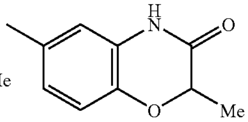 |
| 32 | 4-$CF_3$ | 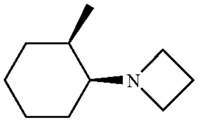 | 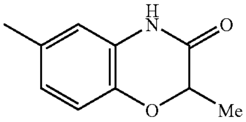 |
TABLE 54
| | | | |
|---|---|---|---|
| 33 | 4-$CF_3$ | 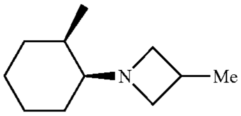 | 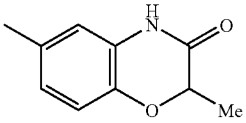 |
| 34 | 4-Cl | 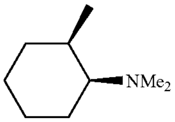 | 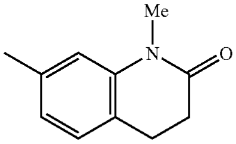 |
| 35 | 4-Cl | 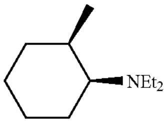 | 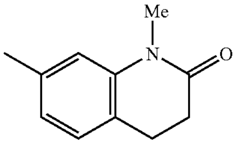 |

TABLE 54-continued
| | | | |
|---|---|---|---|
| 36 | 4-$CF_3$ | 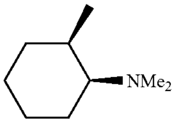 | 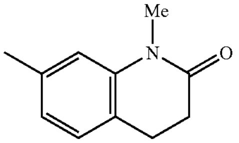 |
| 37 | 4-$CF_3$ | 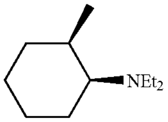 | 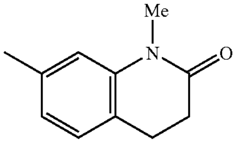 |
| 38 | 4-Cl | 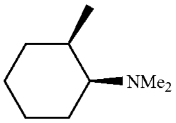 | 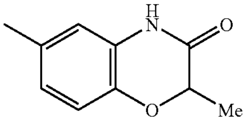 |
| 39 | 4-Cl | 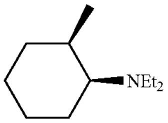 | 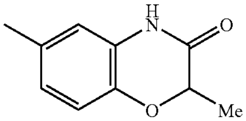 |
| 40 | 4-$CF_3$ | 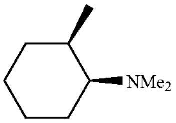 | 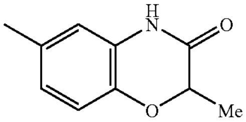 |
| 41 | 4-$CF_3$ | 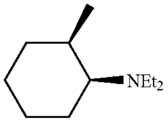 | 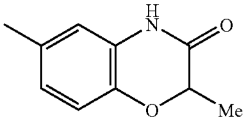 |
| 42 | 4-Cl | 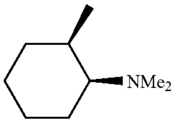 | 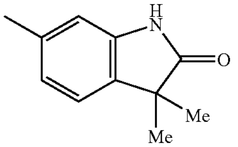 |
| 43 | 4-Cl | 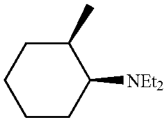 | 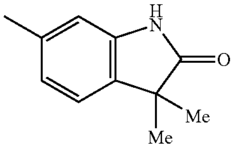 |
| 44 | 4-$CF_3$ | 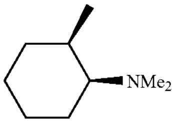 | 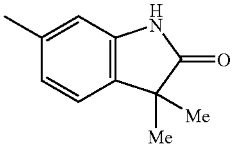 |
| 45 | 4-$CF_3$ | 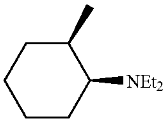 | 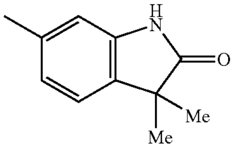 |
| 46 | 4-Cl | 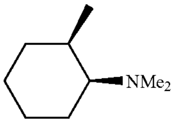 | 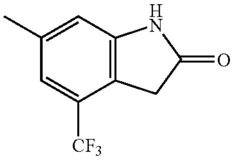 |
| 47 | 4-Cl | 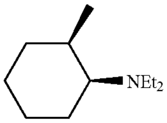 | 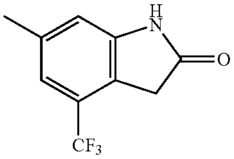 |
| 48 | 4-$CF_3$ | 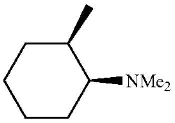 | 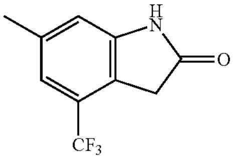 |
| 49 | 4-$CF_3$ | 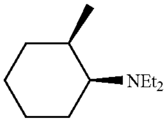 | 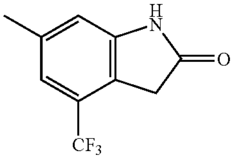 |
| 50 | 4-Cl | 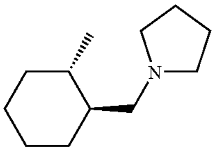 | 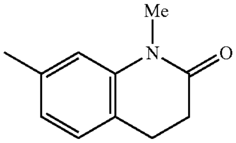 |
| 51 | 4-Cl | 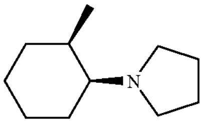 | 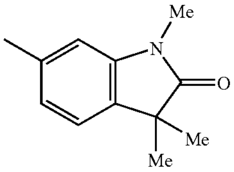 |
| 52 | 4-Cl | 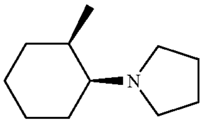 | 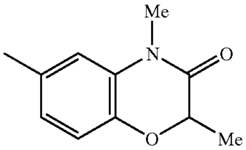 |
| 53 | 4-Et | 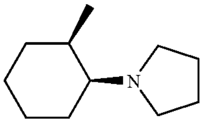 | 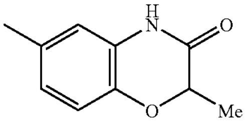 |
| 54 | 4-Me | 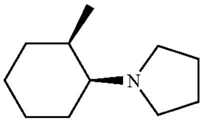 | 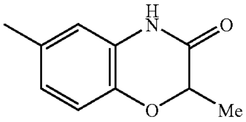 |
Test Examples
Pharmacological activities of the compounds as the active ingredients of the pharmaceutical preparations of the present invention are confirmed by the following tests.

1. Receptor Binding Assay Using VR1 Stably Expressing Cell

1) Construction of Human VR1 Stably Expressing Cell

A complete length cDNA coding for human VR1 was obtained by the following method. Firstly, a first strand cDNA was synthesized by carrying out reverse transcription of human brain mRNA using a reverse transcriptase. Next, PCR by Hot Start method was carried out using this first strand cDNA as the template and using Taq DNA polymerase. In the aforementioned PCR, an oligonucleotide consisting of the $424^{th}$ to $443^{rd}$ nucleotide sequence of a conventionally known human VR1 cDNA sequence (Genbank AJ277028.1) was used as the sense primer, and an oligonucleotide consisting of a complementary chain sequence of the $3082^{nd}$ to $3100^{th}$ nucleotide sequence as the antisense primer, and thermal denaturation was firstly carried out at 98° C. (1 minute) and then a cycle consisting of 98° C. (15 seconds)/63° C. (30 seconds)/72° C. (3 minutes) was repeated 35 times.

Cloning of the thus amplified DNA fragment was carried out using pCR-XL-TOPO vector (TOPO XL PCR Cloning Kit; Invitrogen, USA). The human VR1-cDNA alone was isolated by digesting the resulting plasmid DNA with a restriction enzyme EcoRI and then integrated into pcDNA3.1 (+) plasmid (Invitrogen, USA). In this case, the above genetic engineering operations were carried out by conventionally known methods (Sambrook, J. et al., "Molecular Cloning—A Laboratory Manual", Cold Spring Harbor Laboratory Press, NY, 2001) and in accordance with the instructions attached to respective reagents.

Next, the resulting pcDNA3.1-VR1 was transferred into HEK 293 cell. By selecting VR1/HEK 293 cells using DMEM medium (Invitrogen, USA) containing 10% FBS, 100 µg/ml streptomycin, 100 U/ml penicillin and 400 µg/ml G 418, a receptor stably expressing cell strain was prepared. The receptor stably expressing cell was sub-cultured in the medium described in the above.

2) Preparation of Membrane Sample

The VR1/HEK 293 cell described in the above was mass-produced in a dish and then, after discarding the medium, scraped out after adding ice-cooled PBS. Centrifugation was carried out at 1000 rpm and at 4° C. for 10 minutes, and the resulting residue was homogenized by adding a homogenization buffer (25 mM Tris-HCl, 220 mM sucrose, pH 7.4) and centrifuged at 2,200 rpm and at 4° C. for 10 minutes. The resulting supernatant was centrifuged at 30,000×g and at 4° C. for 20 minutes and the resulting residue was mixed with 25 mM Tris-HCl, pH 7.4, and centrifuged at 30,000×g and at 4° C. for 20 minutes, and this operation was repeated twice. The resulting residue was suspended in 25 mM Tris-HCl, pH 7.4, and the protein concentration was determined using a protein assay staining solution (Bio-Rad, USA). The thus prepared membrane sample was stored at −80° C.

3) Receptor Binding Assay

This was carried out by modifying the method of [Neurosci., 57: 747-757 (1993)]. As the assay buffer, 25 mM Tris-HCl, 0.025% BSA, pH 7.4 was used. Each test compound, $[^3H]$RTX 50 µl (about 50,000 dpm; Perkin Elmer Life Science, USA) and the aforementioned membrane sample (protein quantity about 25 µg) were suspended in a microplate to a total volume of 300 µl, incubated at 37° C. for 60 minutes and then incubated on ice for 10 minutes. A 200 µg/50 µl portion of an ice-cooled $\alpha_1$ acid glycoprotein (AGP; Sigma) was added thereto and further incubated for 5 minutes. Completion of the incubation was carried out by rapid filtration of the reaction liquid using a GF/B filter (Perkin Elmer Life Science, USA). After 7 times of washing with ice-cooled 25 mM Tris-HCl buffer (pH 7.4), radioactivity of the filter was measured by a liquid scintillation counter. Regarding the specific binding, a part substituted by 1 µM of RTX among the total binding of $[^3H]$RTX with the VR1 receptor stably expressing cell membrane fraction was regarded as the specific binding originated from the VR1 receptor. Evaluation of test compounds was carried out in the following manner. That is, reduced quantity of the binding at the time of the addition of each compound was calculated as a relative value when reduced quantity of the binding at the time of the addition of RTX was regarded as 100%. Subsequently, the $IC_{50}$ value was calculated by a Logistic regression method.

The compounds of the present invention were proved to have good activity. The VR1 receptor binding inhibitory activity of the compounds as the active ingredients of the pharmaceutical preparations of the present invention is exemplified in the following parentheses. The value is an $IC_{50}$ value shown by µM.

Example number ($IC_{50}$ value, µM): 1 (0.012), 17 (0.0058), 105 (0.0042), 106 (0.052), 107 (0.013), 108 (0.019), 119 (0.045), 170 (0.0026), 173 (0.0056), 176 (0.0089), 178 (0.062), 248 (0.031), 307 (0.0098), 321 (0.025), 327 (0.0037), 334 (0.023), 335 (0.087), 367 (0.015), 386 (0.018), 400 (0.06)

In addition, the compounds of Examples 2, 5 to 12, 15 to 21, 23 and 24, 26 to 34, 36 to 50, 52 to 58, 60 and 61, 63 to 66, 68 to 71 and 73 to 94 showed $IC_{50}$ values of 5 µM or less. It was confirmed by this assay that the compounds as the active ingredients of the pharmaceutical preparations of the present invention have the VR1 receptor affinity.

2. Measurement of Inhibitory Activity on Capsaicin-Induced Electric Current Using VR1 Stably Expressing Cell The VR1 receptor-expressed HEK 293 cells prepared in the aforementioned Test Example 1 were inoculated onto a poly-D-lysine-coated cover glass to a density of from 1 to $1.5\times10^4$ cells/$cm^2$. This was allowed to stand still in a $CO_2$ incubator (37° C., 5% $CO_2$) and used in this test after a lapse of from 3 to 15 hours.

By recording whole cell patch clamp for the VR1 receptor-expressed HEK 293 cells under a voltage-clamped condition, the current response induced by topically applying capsaicin (1 µM) to the vicinity of the cells was measured. Test compounds were dissolved in an extracellular liquid and applied to a chamber by multi-barrel. Composition (mM) of the extracellular solution was set to NaCl 145, CsCl 5, $CaCl_2$ 1, $MgCl_2$ 1, HEPES 10 and glucose 10 [pH=7.3]. Composition (mM) of the intracellular solution was set to CsCl 120, $MgCl_2$ 2, HEPES 10, BAPTA 10, $Na_2$ GTP 0.2, Mg ATP 4 and phosphorcreatine $Na_2$ 4 [pH=7.2]. By defining the current response of capsaicin in the absence of test compound as 100% and continuously applying each test compound starting from a lower concentration, inhibition rate at each concentration was measured. The $IC_{50}$ value was calculated by nonlinear recursion from respective inhibition rate.

As a result, the compounds as the active ingredients of the pharmaceutical preparations of the present invention showed good inhibitory action. For example, $IC_{50}$ value of the compound of Example 107 was 8.8 nM. By this test, it was confirmed that the compounds as the active ingredients of the pharmaceutical preparations of the present invention has the action to inhibit activation of VR1 receptor.

3. Capsaicin Test

Inhibitory action on pain behavior of the compounds as the active ingredients of the pharmaceutical preparations of the present invention was evaluated in accordance with the method described in a reference [Neuropharmacol., 31: 1279-1285 (1992)]. That is, when 1.6 µg of capsaicin is administered to a planta of a mouse (ddY, male, 4 to 5 weeks of age), it induces paw-licking behavior. The pain behavior suppressing action was evaluated by measuring the paw-licking behavior expressing time during 5 minutes after the administration. Each test compound was orally administered 45 minutes before the administration of capsaicin. Evaluation of the test compounds was carried out by calculating each inhibition rate of the test compound administration group when the paw-licking behavior expressing time of the vehicle administration group was regarded as 100%.

As a result, the compounds as the active ingredients of the pharmaceutical preparations of the present invention showed a strong inhibitory action on pain behavior at the time of their oral administration. The inhibition rate after the oral administration of the compounds as the active ingredients of the pharmaceutical preparations of the present invention is exemplified in the following parentheses.

Example number (inhibition rate): 1 (45%), 17 (54%), 54 (34%), 73 (95%), 107 (53%), 179 (58%), 238 (51%), 261 (56%), 282 (64%), 288 (44%), 321 (67%), 334 (58%), 335 (49%), 347 (57%)

Based on the above results, it was shown that the compounds as the active ingredients of the pharmaceutical preparations of the present invention has a good inhibitory action on pain behavior based on the action to inhibit activation of VR1 receptor.

4. Spinal Nerve Ligation Model Test

Inhibitory action on pain behavior of the compounds as the active ingredients of the pharmaceutical preparations of the present invention was evaluated in accordance with the method described in a reference [Pain, 50: 355-363 (1992)]. Under pentobarbital anesthesia, the lumbar skin and muscle of a rat (SD, male, 5 to 6 weeks of age) were incised and the lumber nerve was exposed by removing the transverse process of lumbar vertebra L 6. The L 5 and L 6 spinal nerves were ligated with a silk thread and then the wound was sutured. The treatment was applied to the left side.

The drug effect evaluation was carried out after 7 to 15 days of the operation. Pain threshold for mechanical stimulus was examined by the von Frey hair (VFH) test. Hair's minimum strength (unit: gram) which shows avoidance reaction when a planta is stimulated was logarithm-converted and used as the pain threshold for mechanical stimulus.

Individuals having lowered pain threshold were selected in advance by the VFH test on the day before the drug effect evaluation and divided into groups in such a manner that difference in the average threshold value between respective groups becomes small.

The test compounds were orally administered 60 minutes before the drug effect evaluation. Evaluation of the test compounds was carried out by calculating each improving rate of test compound administration group when threshold value of the operation side leg in the vehicle administration group was regarded as 0%, and threshold value of the non-operation side leg in this group as 100%.

As a result, it was confirmed that the compounds as the active ingredients of the pharmaceutical preparations of the present invention shows a strong suppressing action on pain behavior also in this test. For example, the compound of Example 107 and the compound of Example 347 completely restored the threshold value of the operation side leg to the threshold value range of the non-operation side leg after the oral administration.

As the result of Test Examples 1 and 2, it was revealed that the compounds as the active ingredients of the pharmaceutical preparations of the present invention have good inhibitory action on VR1 receptor activation. In addition, based on the result of Test Examples 3 and 4, it was revealed that the compounds as the active ingredients of the pharmaceutical preparations of the present invention have a notable pain suppressing action. Accordingly, the compounds as the active ingredients of the pharmaceutical preparations of the present invention are useful as agents for treating or preventing diseases in which VR1 receptor is involved, namely neuropathic pains (e.g., postherpetic neuralgia, diabetic neuropathy and the like), nociceptive pains (e.g., articular pain, postoperative pain, back pain and the like), headaches (e.g., migraine, cluster headache and the like), cancer pain, fibromyalgia, or bladder function disorders (e.g., overactive bladder, urinary incontinence, neurogenic bladder, nocturia, painful bladder syndrome, interstitial cystitis, chronic non-bacterial prostatitis and the like), or bladder dysfunction accompanied by prostatic hypertrophy. In addition, these are also useful as agents for treating or preventing itch, toothache, asthma, chronic obstructive pulmonary disease, cough, inflammatory bowel disease and irritable bowel syndrome.

The pharmaceutical preparation which comprises the compound (I) or a salt thereof as the active ingredient is prepared using carriers, fillers and other additive agents generally used in preparing pharmaceutical preparations.

The administration may be either oral administration by tablets, pills, capsules, granules, powders, solutions and the like or parenteral administration by injections for intravenous injection, intramuscular injection and the like, suppositories, transdermal preparations, transnasal preparations, inhalations and the like. The dose is optionally decided in response to the individual cases by taking symptoms, age, sex and the like of the objects to be administered into consideration, but in the case of oral administration, it is approximately from 0.001 mg/kg to 100 mg/kg per day per adult, and this is administered once or by dividing into 2 to 4 times. Also, when intravenously administered depending on the symptoms, it is administered from once to twice or more a day within the range of generally from 0.0001 mg/kg to 1 mg/kg per once per adult. In addition, in the case of inhalation, it is administered from once to twice or more a day within the range of generally from 0.0001 mg/kg to 1 mg/kg per once per adult.

As the solid composition for oral administration by the present invention, tablets, powders, granules and the like are used. In such a solid composition, one or more active substances are mixed with at least one inert filler such as lactose, mannitol, glucose, hydroxypropylcellulose, microcrystalline cellulose, starch, polyvinyl pyrrolidone, aluminum magnesium silicate or the like. In accordance with the usual way, the composition may contain inert additives such as lubricants (e.g., magnesium stearate and the like), disintegrators (e.g., carboxymethylstarch sodium and the like) and solubilizing agents. As occasion demands, the tablets or pills may be coated with a sugar coating or a gastric or enteric coating agent.

As the liquid composition for oral administration, pharmaceutically acceptable emulsions, solutions, suspensions, syrups, elixirs and the like are included, and generally used inert diluents such as purified water, ethanol and the like can be used. In addition to the inert diluents, this composition may contain auxiliary agents such as solubilizing agents, moistening agents, suspending agents and the like, sweeteners, correctives, aromatics and antiseptics.

As the injections for parenteral administration, sterile aqueous or non-aqueous solutions, suspensions and emulsions are included. As the aqueous solvent, for example, distilled water for injection and physiological saline are included. Examples of the non-aqueous solvent include propylene glycol, polyethylene glycol, plant oil (e.g., olive oil or the like), ethanol or the like alcohols, polysorbate 80 (name in Pharmacopeia) and the like. Such a composition may further contain tonicity agents, antiseptics, moistening agents, emulsifying agents, dispersing agents, stabilizing agents and solubilizing agents. These are sterilized by, for example, filtration through a bacteria retaining filter, formulation of bactericides or irradiation. In addition, these can also be used by producing sterile solid compositions and dissolving or suspending them in sterile water or a sterile solvent for injection prior to use.

Transmucosal preparations such as inhalations, transnasal preparations and the like are used in the form of solid, liquid or semisolid, and can be produced in accordance with the conventionally known methods. For example, excipients such as lactose, starch and the like and also pH adjusting agents, antiseptics, surfactants, lubricants, stabilizers, thickeners and the like may be optionally added. An appropriate device for inhalation or blowing can be used for the administration. For example, a compound can be administered as such or as a powder of formulated mixture, or as a solution or suspension in combination with a medically acceptable carrier, by using a conventionally known device such as a measured administration inhalation device or the like or a sprayer. The dry powder inhaler or the like may be for single or multiple administration use, and a dry powder or powder-containing capsule can be used. Alternatively, it may be in the form of a pressurized aerosol spray or the like which uses an appropriate propellant such as chlorofluoroalkane, hydrofluoroalkane, carbon dioxide or the like suitable gas.

In preparing suppositories, a low melting point wax such as a fatty acid glyceride mixture or cocoa butter is melted, and the active ingredient is added thereto and uniformly dispersed by stirring. Thereafter, this is injected into an appropriate a mold and cooled to effect solidification. The preparations in the form of liquid include a solution, a suspension, a storage enema and an emulsion such as water or propylene glycol aqueous solution.

INDUSTRIAL APPLICABILITY

Since the compounds as the active ingredients of the pharmaceutical preparations of the present invention have a strong action to inhibit activation of capsaicin receptor VR1 and good pharmacological actions based on this, the pharmaceutical compositions of the present invention are useful as agents for treating or preventing diseases in which VR1 is involved, such as diseases in which VR1 is involved, particularly nociceptive pain, neuropathic pain, cancer pain, headache, bladder function disorder, and the like.

The invention claimed is:

1. A 2-aminobenzamide derivative or a pharmaceutically acceptable salt thereof, selected from the group consisting of 4-chloro-N-(1-methyl-2-oxo-1,2,3,4-tetrahydroquinolin-7-yl)-2-{[(1S,2S)-2-pyrrolidin-1-ylcyclohexyl]amino}benzamide, 2-(cyclohexylamino)-N-(2-methyl-3-oxo-3,4-dihydro-2H-1,4-benzoxazin-6-yl)-4-(trifluoromethyl)benzamide, 4-chloro-N-[(2R)-2-methyl-3-oxo-3,4-dihydro-2H-1,4-benzoxazin-6-yl]-2-{[(1R,2S)-2-pyrrolidin-1-ylcyclohexyl]amino}benzamide, N-[2-oxo-4-(trifluoromethyl)-2,3-dihydro-1H-indol-6-yl]-2-{[(1S,2S)-2-pyrrolidin-1-ylcyclohexyl]amino}-4-(trifluoromethyl)benzamide, N-(1-methyl-2-oxo-1,2,3,4-tetrahydroquinolin-7-yl)-2-(pyridin-4-ylamino)-4-(trifluoromethyl)benzamide, N-(3,3-dimethyl-2-oxo-2,3-dihydro-1H-indol-6-yl)-2-{[(1S,2S)-2-pyrrolidin-1-ylcyclohexyl]amino}-4-(trifluoromethyl)benzamide, N-(3,3-dimethyl-2-oxo-2,3-dihydro-1H-indol-6-yl)-2-{[(1R,2R)-2-pyrrolidin-1-ylcyclohexyl]amino}-4-(trifluoromethyl)benzamide, 2-{[(1R,2R)-2-(dimethylamino)cyclohexyl]amino}-N-[(2R)-2-methyl-3-oxo-3,4-dihydro-2H-1,4-benzoxazin-6-yl]-4-(trifluoromethyl)benzamide, 2-{[(1S,2S)-2-(dimethylamino)cyclohexyl]amino}-N-(3,3-dimethyl-2-oxo-2,3-dihydro-1H-indol-6-yl)-4-(trifluoromethyl)benzamide, N-(3,3-dimethyl-2-oxo-2,3-dihydro-1H-indol-6-yl)-2-[(1-isobutylpiperidin-4-yl)amino]-4-(trifluoromethyl)benzamide, N-(3,3-dimethyl-2-oxo-2,3-dihydro-1H-indol-6-yl)-2-{[(3S)-1-pentylpyrrolidin-3-yl]amino}-4-(trifluoromethyl)benzamide, N-(2-oxo-1,2-dihydroquinolin-7-yl)-2-{[(1R,2R)-2-pyrrolidin-1-ylcyclohexyl]amino}-4-(trifluoromethyl)benzamide, 2-[(1-butylpiperidin-4-yl)amino]-N-(3,3-dimethyl-2-oxo-2,3-dihydro-1H-indol-6-yl)-4-(trifluoromethyl)benzamide, N-(3,3-dimethyl-2-oxo-2,3-dihydro-1H-indol-6-yl)-2-{[(1S,2R)-2-pyrrolidin-1-ylcyclohexyl]amino}-4-(trifluoromethyl)benzamide, 2-{[(1S,2R)-2-pyrrolidin-1-ylcyclohexyl]amino}-N-quinolin-7-yl-4-(trifluoromethyl)benzamide, 2-{[(1S,2S)-2-pyrrolidin-1-ylcyclohexyl]amino}-N-quinolin-7-yl-4-(trifluoromethyl)benzamide, and N-[2-oxo-4-(trifluoromethyl)-2,3-dihydro-1H-indol-6-yl]-2-{[(1S,2R)-2-pyrrolidin-1-ylcyclohexyl]amino}-6-(trifluoromethyl)nicotinamide.

2. A pharmaceutical composition, comprising the derivative described in claim 1 or a pharmaceutically acceptable salt thereof and a pharmaceutically acceptable carrier.

3. The derivative described in claim 1, wherein said derivative is N-(3,3-dimethyl-2-oxo-2,3-dihydro-1H-indol-6-yl)-2-{[(1S,2S)-2-pyrrolidin-1-ylcyclohexyl]amino}-4-(trifluoromethyl)benzamide, or a pharmaceutically acceptable salt thereof.

4. A pharmaceutical composition, comprising the derivative described in claim 3 or a pharmaceutically acceptable salt thereof and a pharmaceutically acceptable carrier.

* * * * *